United States Patent
Burright et al.

(10) Patent No.: US 8,173,614 B2
(45) Date of Patent: *May 8, 2012

(54) THERAPEUTING COMPOSITIONS COMPRISING AN RNAI AGENT AND A NEUROTROPHIC FACTOR AND METHODS OF USE THEREOF

(75) Inventors: Eric Neal Burright, Eagan, MN (US); William F. Kaemmerer, Edina, MN (US); Deepak Ramesh Thakker, Blaine, MN (US); Jennifer Heisel, Princeton, MN (US)

(73) Assignee: Medtronic, Inc., Minneapolis, MN (US)

( * ) Notice: Subject to any disclaimer, the term of this patent is extended or adjusted under 35 U.S.C. 154(b) by 41 days.

This patent is subject to a terminal disclaimer.

(21) Appl. No.: 12/580,973

(22) Filed: Oct. 16, 2009

(65) Prior Publication Data

US 2010/0113351 A1    May 6, 2010

Related U.S. Application Data

(63) Continuation-in-part of application No. 12/522,153, filed as application No. PCT/US2008/050089 on Jan. 3, 2008.

(60) Provisional application No. 60/878,371, filed on Jan. 3, 2007.

(51) Int. Cl.
  *C12N 15/11* (2006.01)
  *A61K 31/70* (2006.01)
  *A61K 48/00* (2006.01)
  *C07H 21/02* (2006.01)
  *C07H 21/04* (2006.01)

(52) U.S. Cl. .................. 514/44; 536/24.1; 536/24.5

(58) Field of Classification Search ............... 536/23.1, 536/24.3, 24.33, 24.5

See application file for complete search history.

(56) References Cited

U.S. PATENT DOCUMENTS

| | | |
|---|---|---|
| 2004/0220132 A1 | 11/2004 | Kaemmerer |
| 2006/0210538 A1 | 9/2006 | Kaplitt et al. |
| 2010/0113351 A1 | 5/2010 | Burright et al. |
| 2010/0132060 A1* | 5/2010 | Burright ............ 800/18 |

OTHER PUBLICATIONS

Zuccato et al. Science, 2001 vol. 293:493-498.*
Geraerts et al., "Concise Review; Therapeutic Strategies for Parkinson Disease Based on the Modulation of Adult Neurogenesis", Stem Cells, Nov. 2, 2006; vol. 25, No. 2; pp. 263-270.

* cited by examiner

*Primary Examiner* — Terra Cotta Gibbs
(74) *Attorney, Agent, or Firm* — Fox Rothschild LLP

(57) ABSTRACT

The invention provides novel combination therapies for treating Huntington's disease which comprise a) BDNF or suitable fragments thereof and b) agents capable of causing inhibition of a gene responsible for the neurodegenerative disease. The invention provides nucleic acid sequences, methods, and systems suitable for applications of these combination therapies.

19 Claims, 5 Drawing Sheets

SEQUENCE LISTING

```
<160> NUMBER OF SEQ ID NOS: 71

<210> SEQ ID NO 1
<211> LENGTH: 19
<212> TYPE: DNA
<213> ORGANISM: Artificial
<220> FEATURE:
<223> OTHER INFORMATION: Artificial RNAi Sequence

<400> SEQUENCE: 1
tgacagcagt gttgataaa                                                    19

<210> SEQ ID NO 2
<211> LENGTH: 19
<212> TYPE: DNA
<213> ORGANISM: Artificial
<220> FEATURE:
<223> OTHER INFORMATION: Artificial RNAi Sequence

<400> SEQUENCE: 2
aagaacgagt gctcaataa                                                    19

<210> SEQ ID NO 3
<211> LENGTH: 19
<212> TYPE: DNA
<213> ORGANISM: Artificial
<220> FEATURE:
<223> OTHER INFORMATION: Artificial RNAi Sequence

<400> SEQUENCE: 3
tttatgaact gacgttaca                                                    19

<210> SEQ ID NO 4
<211> LENGTH: 19
<212> TYPE: DNA
<213> ORGANISM: Artificial
<220> FEATURE:
<223> OTHER INFORMATION: Artificial RNAi Sequence

<400> SEQUENCE: 4
```

| | |
|---|---|
| ggagtattgt ggaacttat | 19 |

<210> SEQ ID NO 5
<211> LENGTH: 19
<212> TYPE: DNA
<213> ORGANISM: Artificial
<220> FEATURE:
<223> OTHER INFORMATION: Artificial RNAi Sequence

<400> SEQUENCE: 5

| | |
|---|---|
| gagtattgtg gaacttata | 19 |

<210> SEQ ID NO 6
<211> LENGTH: 19
<212> TYPE: DNA
<213> ORGANISM: Artificial
<220> FEATURE:
<223> OTHER INFORMATION: Artificial RNAi Sequence

<400> SEQUENCE: 6

| | |
|---|---|
| agaccgtgtg aatcattgt | 19 |

<210> SEQ ID NO 7
<211> LENGTH: 19
<212> TYPE: DNA
<213> ORGANISM: Artificial
<220> FEATURE:
<223> OTHER INFORMATION: Artificial RNAi Sequence

<400> SEQUENCE: 7

| | |
|---|---|
| ggttacagct cgagctcta | 19 |

<210> SEQ ID NO 8
<211> LENGTH: 19
<212> TYPE: DNA
<213> ORGANISM: Artificial
<220> FEATURE:
<223> OTHER INFORMATION: Artificial RNAi Sequence

<400> SEQUENCE: 8

| | |
|---|---|
| ggttttgtta aaggccttc | 19 |

<210> SEQ ID NO 9
<211> LENGTH: 27
<212> TYPE: DNA
<213> ORGANISM: Artificial
<220> FEATURE:
<223> OTHER INFORMATION: Artificial RNAi Sequence

<400> SEQUENCE: 9

| | |
|---|---|
| tgacagcagt gttgataaat ttgtgtt | 27 |

<210> SEQ ID NO 10
<211> LENGTH: 27
<212> TYPE: DNA
<213> ORGANISM: Artificial
<220> FEATURE:
<223> OTHER INFORMATION: Artificial RNAi Sequence

<400> SEQUENCE: 10

| | |
|---|---|
| aagaacgagt gctcaataat gttgtca | 27 |

<210> SEQ ID NO 11
<211> LENGTH: 27
<212> TYPE: DNA
<213> ORGANISM: Artificial
<220> FEATURE:

-continued

<223> OTHER INFORMATION: Artificial RNAi Sequence

<400> SEQUENCE: 11
tttatgaact gacgttacat catacac                                           27

<210> SEQ ID NO 12
<211> LENGTH: 27
<212> TYPE: DNA
<213> ORGANISM: Artificial
<220> FEATURE:
<223> OTHER INFORMATION: Artificial RNAi Sequence

<400> SEQUENCE: 12
ggagtattgt ggaacttata gctggag                                           27

<210> SEQ ID NO 13
<211> LENGTH: 27
<212> TYPE: DNA
<213> ORGANISM: Artificial
<220> FEATURE:
<223> OTHER INFORMATION: Artificial RNAi Sequence

<400> SEQUENCE: 13
gagtattgtg gaacttatag ctggagg                                           27

<210> SEQ ID NO 14
<211> LENGTH: 27
<212> TYPE: DNA
<213> ORGANISM: Artificial
<220> FEATURE:
<223> OTHER INFORMATION: Artificial RNAi Sequence

<400> SEQUENCE: 14
agaccgtgtg aatcattgtc tgacaat                                           27

<210> SEQ ID NO 15
<211> LENGTH: 27
<212> TYPE: DNA
<213> ORGANISM: Artificial
<220> FEATURE:
<223> OTHER INFORMATION: Artificial RNAi Sequence

<400> SEQUENCE: 15
ggttttgtta aaggccttca tagcgaa                                           27

<210> SEQ ID NO 16
<211> LENGTH: 13481
<212> TYPE: DNA
<213> ORGANISM: Homo sapiens

<400> SEQUENCE: 16
gctgccggga cgggtccaag atggacggcc gctcaggttc tgcttttacc tgcggcccag       60
agccccattc attgccccgg tgctgagcgg cgccgcgagt cggcccgagg cctccgggga      120
ctgccgtgcc gggcgggaga ccgccatggc gaccctggaa aagctgatga aggccttcga      180
gtccctcaag tccttccagc agcagcagca gcagcagcag cagcagcagc agcagcagca      240
gcagcagcag cagcagcagc aacagccgcc accgccgccg ccgccgccgc cgcctcctca      300
gcttcctcag ccgccgccgc aggcacagcc gctgctgcct cagccgcagc cgccccgcc      360 gccgccccg ccgccacccg gccggctgt ggctgaggag ccgctgcacc gaccaaagaa       420
agaactttca gctaccaaga agaccgtgt gaatcattgt ctgacaatat gtgaaaacat      480
agtggcacag tctgtcagaa attctccaga atttcagaaa cttctgggca tcgctatgga      540

-continued

```
acttttttctg ctgtgcagtg atgacgcaga gtcagatgtc aggatggtgg ctgacgaatg      600
cctcaacaaa gttatcaaag cttttgatgga ttctaatctt ccaaggttac agctcgagct      660
ctataaggaa attaaaaaga atggtgcccc tcggagtttg cgtgctgccc tgtggaggtt      720
tgctgagctg gctcacctgg ttcggcctca gaaatgcagg ccttacctgg tgaaccttct      780
gccgtgcctg actcgaacaa gcaagagacc cgaagaatca gtccaggaga ccttggctgc      840
agctgttccc aaaattatgg cttcttttgg caattttgca aatgacaatg aaattaaggt      900
tttgttaaag ccttcatag cgaacctgaa gtcaagctcc cccaccattc ggcggacagc       960
ggctggatca gcagtgagca tctgccagca ctcaagaagg acacaatatt tctatagttg     1020
gctactaaat gtgctcttag gcttactcgt tcctgtcgag gatgaacact ccactctgct     1080
gattcttggc gtgctgctca ccctgaggta tttggtgccc ttgctgcagc agcaggtcaa     1140
ggacacaagc ctgaaaggca gcttcggagt gacaaggaaa gaaatggaag tctctccttc     1200
tgcagagcag cttgtccagg tttatgaact gacgttacat catacacagc accaagacca     1260
caatgttgtg accggagccc tggagctgtt gcagcagctc ttcagaacgc tccacccga     1320 gcttctgcaa accctgaccg cagtcggggg cattgggcag ctcaccgctg ctaaggagga     1380
gtctggtggc cgaagccgta gtgggagtat tgtggaactt atagctggag ggggttcctc     1440
atgcagccct gtccttttcaa gaaaacaaaa aggcaaagtg ctcttaggag aagaagaagc     1500
cttggaggat gactctgaat cgagatcgga tgtcagcagc tctgccttaa cagcctcagt     1560
gaaggatgag atcagtggag agctggctgc ttcttcaggg gtttccactc cagggtcagc     1620
aggtcatgac atcatcacag aacagccacg gtcacagcac acactgcagg cggactcagt     1680
ggatctggcc agctgtgact tgacaagctc tgccactgat ggggatgagg aggatatctt     1740
gagccacagc tccagccagg tcagcgccgt cccatctgac cctgccatgg acctgaatga     1800
tgggacccag gcctcgtcgc ccatcagcga cagctcccag accaccccg aagggcctga      1860 ttcagctgtt accccttcag acagttctga aattgtgtta gacggtaccg acaaccagta     1920
tttgggcctg cagattggac agccccagga tgaagatgag gaagccacag gtattcttcc     1980
tgatgaagcc tcggaggcct tcaggaactc ttccatggcc cttcaacagg cacatttatt     2040
gaaaaacatg agtcactgca ggcagccttc tgacagcagt gttgataaat ttgtgttgag     2100
agatgaagct actgaaccgg gtgatcaaga aaacaagcct tgccgcatca aggtgacat      2160 tggacagtcc actgatgatg actctgcacc tcttgtccat tgtgtccgcc ttttatctgc     2220
ttcgtttttg ctaacagggg gaaaaaatgt gctggttccg gacagggatg tgagggtcag     2280
cgtgaaggcc ctggccctca gctgtgtggg agcagctgtg gccctccacc cggaatcttt     2340
cttcagcaaa ctctataaag ttcctcttga caccacggaa tacctgagg acagtatgt      2400 ctcagacatc ttgaactaca tcgatcatgg agacccacag gttcgaggag ccactgccat     2460
tctctgtggg accctcatct gctccatcct cagcaggtcc cgcttccacg tgggagattg     2520
gatgggcacc attagaaccc tcacaggaaa tacattttct ttggcggatt gcattccttt     2580
gctgcggaaa acactgaagg atgagtcttc tgttacttgc aagttagctt gtacagctgt     2640
gaggaactgt gtcatgagtc tctgcagcag cagctacagt gagttaggac tgcagctgat     2700
catcgatgtg ctgactctga ggaacagttc ctattggctg gtgaggacag agcttctgga     2760
aacccttgca gagattgact tcaggctggt gagcttttg gaggcaaaag cagaaaactt      2820
acacagaggg gctcatcatt atacagggct tttaaaactg caagaacgag tgctcaataa     2880
tgttgtcatc catttgcttg gagatgaaga ccccagggtg cgacatgttg ccgcagcatc     2940
```

```
actaattagg cttgtcccaa agctgtttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taacctttca agagttattg cagcagtttc    3180
tcatgaacta atcacatcaa ccaccagagc actcacattt ggatgctgtg aagctttgtg    3240
tcttctttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca aaccccccctt ctctaagtcc catccgacga aaggggaagg agaaagaacc    3720
aggagaacaa gcatctgtac cgttgagtcc caagaaaggc agtgaggcca gtgcagcttc    3780
tagacaatct gatacctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960
cttggatgtt cttttctcaga tactagagct ggccacactg caggacattg gaagtgtgt    4020 tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aaccccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac ctcttgttat    4440
aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga aacagtttga atacattgaa gtgggccagt tcagggaatc    4620
agaggcaatc attccaaaca tcttttttctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata agctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggccccct tcctccctcc gtccggtaga    5100
catgctttta cggagtatgt tcgtcactcc aaacacaatg gcgtccgtga gcactgttca    5160
actgtggata tcgggaattc tggccatttt gagggttctg atttcccagt caactgaaga    5220
tattgttctt tctcgtattc aggagctctc cttctctccg tatttaatct cctgtacagt    5280
aattaatagg ttaagagatg gggacagtac ttcaacgcta gaagaacaca gtgaagggaa    5340
```

```
acaaataaag aatttgccag aagaaacatt ttcaaggttt ctattacaac tggttggtat      5400
tcttttagaa gacattgtta caaaacagct gaaggtggaa atgagtgagc agcaacatac      5460
tttctattgc caggaactag gcacactgct aatgtgtctg atccacatct tcaagtctgg      5520
aatgttccgg agaatcacag cagctgccac taggctgttc cgcagtgatg gctgtggcgg      5580
cagtttctac accctggaca gcttgaactt gcgggctcgt tccatgatca ccacccaccc      5640
ggccctggtg ctgctctggt gtcagatact gctgcttgtc aaccacaccg actaccgctg      5700
gtgggcagaa gtgcagcaga ccccgaaaag acacagtctg tccagcacaa agttacttag      5760
tccccagatg tctggagaag aggaggattc tgacttggca gccaaacttg gaatgtgcaa      5820
tagagaaata gtacgaagag gggctctcat tctcttctgt gattatgtct gtcagaacct      5880
ccatgactcc gagcacttaa cgtggctcat tgtaaatcac attcaagatc tgatcagcct      5940
ttcccacgag cctccagtac aggacttcat cagtgccgtt catcggaact ctgctgccag      6000
cggcctgttc atccaggcaa ttcagtctcg ttgtgaaaac cttcaactc caaccatgct       6060
gaagaaaact cttcagtgct ggagggggat ccatctcagc cagtcgggag ctgtgctcac      6120
gctgtatgtg gacaggcttc tgtgcacccc tttccgtgtg ctggctcgca tggtcgacat      6180
ccttgcttgt cgccgggtag aaatgcttct ggctgcaaat ttacagagca gcatggccca      6240
gttgccaatg aagaactca acagaatcca ggaatacctt cagagcagcg gctcgctca       6300
gagacaccaa aggctctatt ccctgctgga caggtttcgt ctctccacca tgcaagactc      6360
acttagtccc tctcctccag tctcttccca cccgctggac ggggatgggc acgtgtcact      6420
ggaaacagtg agtccggaca aagactggta cgttcatctt gtcaaatccc agtgttggac      6480
caggtcagat tctgcactgc tggaaggtgc agagctggtg aatcggattc tgctgaaga      6540
tatgaatgcc ttcatgatga actcggagtt caacctaagc ctgctagctc catgcttaag      6600
cctaggatg agtgaaattt ctggtggcca aagagtgcc ctttttgaag cagcccgtga       6660
ggtgactctg gcccgtgtga gcggcaccgt gcagcagctc cctgctgtcc atcatgtctt      6720
ccagcccgag ctgcctgcag agccggcggc ctactggagc aagttgaatg atctgtttgg      6780
ggatgctgca ctgtatcagt ccctgcccac tctggcccgg gccctggcac agtacctggt      6840
ggtggtctcc aaactgccca gtcatttgca ccttcctcct gagaaagaga aggacattgt      6900
gaaattcgtg gtggcaaccc ttgaggcct gtcctggcat ttgatccatg agcagatccc      6960
gctgagtctg gatctccagg cagggctgga ctgctgctgc ctggccctgc agctgcctgg      7020
cctctggagc gtggtctcct ccacagagtt tgtgacccac gcctgctccc tcatctactg      7080
tgtgcacttc atcctggagg ccgttgcagt gcagcctgga gagcagcttc ttagtccaga      7140
aagaaggaca aataccccaa aagccatcag cgaggaggag gaggaagtag atccaaacac      7200
acagaatcct aagtatatca ctgcagcctg tgagatggtg gcagaaatgg tggagtctct      7260
gcagtcggtt ttggccttgg gtcataaaag gaatagcggc gtgccggcgt ttctcacgcc      7320
attgctaagg aacatcatca tcagcctggc ccgcctgccc cttgtcaaca gctacacacg      7380
tgtgcccca ctggtgtgga gcttggatg gtcacccaaa ccgggagggg attttggcac       7440
agcattccct gagatccccg tggagttcct ccaggaaaag gaagtcttta aggagttcat      7500
ctaccgcatc aacacactag gctggaccag tcgtactcag tttgaagaaa cttgggccac      7560
cctccttggt gtcctggtga cgcagcccct cgtgatggag caggaggaga gcccaccaga      7620
agaagacaca gagaggaccc agatcaacgt cctggccgtg caggccatca cctcactggt      7680
gctcagtgca atgactgtgc ctgtggccgg caacccagct gtaagctgct tggagcagca      7740
```

-continued

```
gccccggaac aagcctctga aagctctcga caccaggttt gggaggaagc tgagcattat    7800
cagagggatt gtggagcaag agattcaagc aatggtttca aagagagaga atattgccac    7860
ccatcattta tatcaggcat gggatcctgt cccttctctg tctccggcta ctacaggtgc    7920
cctcatcagc cacgagaagc tgctgctaca gatcaacccc gagcgggagc tggggagcat    7980
gagctacaaa ctcggccagg tgtccataca ctccgtgtgg ctggggaaca gcatcacacc    8040
cctgagggag gaggaatggg acgaggaaga ggaggaggag gccgacgccc ctgcaccttc    8100
gtcaccaccc acgtctccag tcaactccag gaaacaccgg gctggagttg acatccactc    8160
ctgttcgcag tttttgcttg agttgtacag ccgctggatc ctgccgtcca gctcagccag    8220
gaggaccccg gccatcctga tcagtgaggt ggtcagatcc cttctagtgg tctcagactt    8280
gttcaccgag cgcaaccagt ttgagctgat gtatgtgacg ctgacagaac tgcgaagggt    8340
gcacccttca gaagacgaga tcctcgctca gtacctggtg cctgccacct gcaaggcagc    8400
tgccgtcctt gggatggaca aggccgtggc ggagcctgtc agccgcctgc tggagagcac    8460
gctcaggagc agccacctgc ccagcagggt tggagccctg cacggcgtcc tctatgtgct    8520
ggagtgcgac ctgctggacg acactgccaa gcagctcatc ccggtcatca gcgactatct    8580
cctctccaac ctgaaaggga tcgcccactg cgtgaacatt cacagccagc agcacgtact    8640
ggtcatgtgt gccactgcgt tttacctcat tgagaactat cctctggacg tagggccgga    8700
attttcagca tcaataatac agatgtgtgg ggtgatgctg tctggaagtg aggagtccac    8760
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc    9000
agtgattgtt gctatggagc gggtatctgt tcttttgat aggatcagga aaggcttcc    9060
ttgtgaagcc agagtggtgg ccaggatcct gccccagttt ctagacgact tcttcccacc    9120
ccaggacatc atgaacaaag tcatcggaga gtttctgtcc aaccagcagc atacccccca    9180
gttcatggcc accgtggtgt ataaggtgtt tcagactctg cacagcaccg gcagtcgtc    9240
catggtccgg gactgggtca tgctgtccct ctccaacttc acgcagaggg ccccggtcgc    9300
catgccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat gggcttccgc acatgccgcg ggcggccagg caacgtgcgt    9720
gtctctgcca tgtggcagaa gtgctctttg tggcagtggc caggcaggga gtgtctgcag    9780
tcctggtggg gctgagcctg aggccttcca gaaagcagga gcagctgtgc tgcacccat    9840
gtgggtgacc aggtcctttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg    10020
ggtgtgcatg ccacgcccg tgtctggatg cacagatgcc atggcctgtg ctgggccagt    10080
ggctgggggt gctagacacc cggcaccatt ctcccttctc tctttcttc tcaggattta    10140
```

```
aaatttaatt atatcagtaa agagattaat tttaacgtaa ctcttctat gcccgtgtaa    10200 agtatgtgaa tcgcaaggcc tgtgctgcat gcgacagcgt ccggggtggt ggacagggcc    10260
cccggccacg ctccctctcc tgtagccact ggcatagccc tcctgagcac ccgctgacat    10320
ttccgttgta catgttcctg tttatgcatt cacaaggtga ctgggatgta gagaggcgtt    10380
agtgggcagg tggccacagc aggactgagg acaggccccc attatcctag gggtgcgctc    10440
acctgcagcc cctcctcctc gggcacagac gactgtcgtt ctccacccac cagtcaggga    10500
cagcagcctc cctgtcactc agctgagaag gccagccctc cctggctgtg agcagcctcc    10560
actgtgtcca gagacatggg cctcccactc ctgttccttg ctagccctgg ggtggcgtct    10620
gcctaggagc tggctggcag gtgttgggac ctgctgctcc atggatgcat gccctaagag    10680
tgtcactgag ctgtgttttg tctgagcctc tctcggtcaa cagcaaagct tggtgtcttg    10740
gcactgttag tgacagagcc cagcatccct tctgcccccg ttccagctga catcttgcac    10800 ggtgaccct tttagtcagg agagtgcaga tctgtgctca tcggagactg ccccacggcc    10860
ctgtcagagc cgccactcct atccccaggc caggtccctg gaccagcctc ctgtttgcag    10920
gcccagagga gccaagtcat taaaatggaa gtggattctg gatggccggg ctgctgctga    10980
tgtaggagct ggatttggga gctctgcttg ccgactggct gtgagacgag gcagggctc    11040 tgcttcctca gccctagagg cgagccaggc aaggttggcg actgtcatgt ggcttggttt    11100
ggtcatgccc gtcgatgttt tgggtattga atgtggtaag tggaggaaat gttggaactc    11160
tgtgcaggtg ctgccttgag acccccaagc ttccacctgt ccctctccta tgtggcagct    11220
ggggagcagc tgagatgtgg acttgtatgc tgcccacata cgtgagggg agctgaaagg    11280 gagcccctcc tctgagcagc ctctgccagg cctgtatgag cttttcca ccagctccca    11340 acagaggcct cccccagcca ggaccactc gtcctcgtgg cggggcagca ggagcggtag    11400
aaaggggtcc gatgtttgag gaggccctta agggaagcta ctgaattata acacgtaaga    11460
aaatcaccat tccgtattgg ttgggggctc ctgtttctca tcctagcttt ttcctggaaa    11520
gcccgctaga aggtttggga acgagggaa agttctcaga actgttggct gctccccacc    11580
cgcctcccgc ctcccccgca ggttatgtca gcagctctga gacagcagta tcacaggcca    11640
gatgttgttc ctggctagat gtttacattt gtaagaaata acactgtgaa tgtaaaacag    11700
agccattccc ttggaatgca tatcgctggg ctcaacatag agtttgtctt cctcttgttt    11760
acgacgtgat ctaaaccagt ccttagcaag gggctcagaa caccccgctc tggcagtagg    11820
tgtcccccac cccaaagac ctgcctgtgt gctccggaga tgaatatgag ctcattagta    11880
aaaatgactt cacccacgca tatacataaa gtatccatgc atgtgcatat agacacatct    11940 ataatttac acacacacct ctcaagacgg agatgcatgg cctctaagag tgcccgtgtc    12000
ggttcttcct ggaagttgac tttccttaga cccgccaggt caagttagcc gcgtgacgga    12060
catccaggcg tgggacgtgg tcagggcagg gctcattcat tgcccactag gatcccactg    12120
gcgaagatgg tctccatatc agctctctgc agaagggagg aagactttat catgttccta    12180
aaaatcgtgt gcaagcaccc atcgtattat ccaaattttg ttgcaaatgt gattaatttg    12240
gttgtcaagt tttggggggtg ggctgtgggg agattgcttt tgttttcctg ctggtaatat    12300
cgggaaagat tttaatgaaa ccagggtaga attgttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaaccccct ccagacaccc agaatgtagc atctgagaag    12540
```

```
gccctgtgcc ctaaaggaca cccctcgccc ccatcttcat ggaggggtc atttcagagc      12600 cctcggagcc aatgaacagc tcctcctctt ggagctgaga tgagcccac gtggagctcg      12660 ggacggatag tagacagcaa taactcggtg tgtggccgcc tggcaggtgg aacttcctcc      12720
cgttgcgggg tggagtgagg ttagttctgt gtgtctggtg ggtggagtca ggcttctctt      12780
gctacctgtg agcatccttc ccagcagaca tcctcatcgg gctttgtccc tcccccgctt      12840
cctccctctg cggggaggac ccgggaccac agctgctggc cagggtagac ttggagctgt      12900
cctccagagg ggtcacgtgt aggagtgaga agaaggaaga tcttgagagc tgctgaggga      12960
ccttggagag ctcaggatgg ctcagacgag gacactcgct tgccgggcct gggcctcctg      13020
ggaaggaggg agctgctcag aatgccgcat gacaactgaa ggcaacctgg aaggttcagg      13080
ggccgctctt cccccatgtg cctgtcacgc tctggtgcag tcaaaggaac gccttcccct      13140
cagttgtttc taagagcaga gtctcccgct gcaatctggg tggtaactgc cagccttgga      13200
ggatcgtggc caacgtggac ctgcctacg agggtgggct ctgacccaag tggggcctcc      13260
ttgtccaggt ctcactgctt tgcaccgtgg tcagagggac tgtcagctga gcttgagctc      13320
ccctggagcc agcagggctg tgatgggcga gtcccggagc cccacccaga cctgaatgct      13380
tctgagagca aagggaagga ctgacgagag atgtatattt aattttttaa ctgctgcaaa      13440
cattgtacat ccaaattaaa ggaaaaaaat ggaaaccatc a                          13481

<210> SEQ ID NO 17
<211> LENGTH: 5850
<212> TYPE: DNA
<213> ORGANISM: Homo sapiens

<400> SEQUENCE: 17
acaagtcttt ccgcctcccc agcccgcccg ggagctgcga gccgcgagct ggattatggt        60
ggcctgagca gccaacgcag ccgcaggagc ccggagccct tgcccctgcc cgcgccgccg       120
cccgccgggg ggaccaggga agccgccacc ggcccgccat gcccgcccct cccagccccg       180 ccggagccc gcgcccgctg ccaggctgg ccgccgccgt gccgatgtag cgggctccgg        240
atcccagcct ctcccctgct cccgtgctct gcggatctcc cctgaccgct tccacagcc        300 cggacccggg ggctggccca gggccctgca ggccctggcg tcctgatgcc cccaagctcc       360
ctctcctgag aagccaccag caccacccag acttgggggc aggcgccagg gacggacgtg       420
ggccagtgcg agcccagagg gcccgaaggc cggggcccac catggcccaa gccctgccct       480
ggctcctgct gtggatgggc gcgggagtgc tgcctgccca cggcacccag cacggcatcc       540
ggctgcccct gcgcagcggc ctgggggcg cccccctggg gctgcggctg cccgggaga        600 ccgacgaaga gcccgaggag cccggccgga ggggcagctt tgtggagatg gtggacaacc       660
tgaggggcaa gtcggggcag ggctactacg tggagatgac cgtgggcagc ccccgcaga       720 cgctcaacat cctggtggat acaggcagca gtaactttgc agtgggtgct gccccccacc       780
ccttcctgca tcgctactac cagaggcagc tgtccagcac ataccgggac ctccggaagg       840
gtgtgtatgt gcctacacc cagggcaagt gggaaggga gctgggcacc gacctggtaa        900
gcatccccca tggccccaac gtcactgtgc gtgccaacat tgctgccatc actgaatcag       960
acaagttctt catcaacggc tccaactggg aaggcatcct ggggctggcc tatgctgaga      1020
ttgccaggcc tgacgactcc ctggagcctt tctttgactc tctggtaaag cagacccacg      1080
ttcccaacct cttctccctg cagctttgtg gtgctggctt cccctcaac cagtctgaag      1140 tgctggcctc tgtcggaggg agcatgatca ttggaggtat cgaccactcg ctgtacacag      1200
```

```
gcagtctctg gtatacaccc atccggcggg agtggtatta tgaggtgatc attgtgcggg    1260
tggagatcaa tggacaggat ctgaaaatgg actgcaagga gtacaactat gacaagagca    1320
ttgtggacag tggcaccacc aaccttcgtt tgcccaagaa agtgtttgaa gctgcagtca    1380
aatccatcaa ggcagcctcc tccacggaga agttccctga tggttctgg ctaggagagc     1440 agctggtgtg ctggcaagca ggcaccaccc cttggaacat tttcccagtc atctcactct    1500
acctaatggg tgaggttacc aaccagtcct tccgcatcac catccttccg cagcaatacc    1560
tgcggccagt ggaagatgtg ccacgtccc aagacgactg ttacaagttt gccatctcac     1620
agtcatccac gggcactgtt atgggagctg ttatcatgga gggcttctac gttgtctttg    1680
atcgggcccg aaaacgaatt ggctttgctg tcagcgcttg ccatgtgcac gatgagttca    1740
ggacggcagc ggtggaaggc ccttttgtca ccttggacat ggaagactgt ggctacaaca    1800
ttccacagac agatgagtca accctcatga ccatagccta tgtcatggct gccatctgcg    1860
ccctcttcat gctgccactc tgcctcatgg tgtgtcagtg gcgctgcctc cgctgcctgc    1920
gccagcagca tgatgacttt gctgatgaca tctccctgct gaagtgagga ggcccatggg    1980
cagaagatag agattcccct ggaccacacc tccgtggttc actttggtca caagtaggag    2040
acacagatgg cacctgtggc cagagcacct caggaccctc cccacccacc aaatgcctct    2100
gccttgatga gaaggaaaa ggctggcaag gtgggttcca gggactgtac ctgtaggaaa      2160
cagaaaagag aagaaagaag cactctgctg gcgggaatac tcttggtcac ctcaaattta    2220
agtcgggaaa ttctgctgct tgaaacttca gccctgaacc tttgtccacc attcctttaa    2280
attctccaac ccaaagtatt cttcttttct tagtttcaga agtactggca tcacacgcag    2340
gttaccttgg cgtgtgtccc tgtggtaccc tggcagagaa gagaccaagc ttgtttccct    2400
gctggccaaa gtcagtagga gaggatgcac agtttgctat ttgctttaga gacagggact    2460
gtataaacaa gcctaacatt ggtgcaaaga ttgcctcttg aattaaaaaa aaaaactaga    2520
ttgactattt atacaaatgg gggcggctgg aaagaggaga aggagaggga gtacaaagac    2580
agggaatagt gggatcaaag ctaggaaagg cagaaacaca accactcacc agtcctagtt    2640
ttagacctca tctccaagat agcatcccat ctcagaagat gggtgttgtt ttcaatgttt    2700
tcttttctgt ggttgcagcc tgaccaaaag tgagatggga agggcttatc tagccaaaga    2760
gctctttttt agctctctta aatgaagtgc ccactaagaa gttccactta acacatgaat    2820
ttctgccata ttaatttcat tgtctctatc tgaaccaccc tttattctac atatgatagg    2880
cagcactgaa atatcctaac cccctaagct ccaggtgccc tgtgggagag caactggact    2940
atagcagggc tgggctctgt cttcctggtc ataggctcac tctttccccc aaatcttcct    3000
ctggagcttt gcagccaagg tgctaaaagg aataggtagg agacctcttc tatctaatcc    3060
ttaaaagcat aatgttgaac attcattcaa cagctgatgc cctataaccc ctgcctggat    3120
ttcttcctat taggctataa gaagtagcaa gatctttaca taattcagag tggtttcatt    3180
gccttcctac cctctctaat ggcccctcca tttatttgac taaagcatca cacagtggca    3240
ctagcattat accaagagta tgagaaatac agtgctttat ggctctaaca ttactgcctt    3300
cagtatcaag gctgcctgga gaaaggatgg cagcctcagg gcttccttat gtcctccacc    3360
acaagagctc cttgatgaag gtcatctttt tcccctatcc tgttcttccc ctcccgctc     3420 ctaatggtac gtgggtaccc aggctggttc ttgggctagg tagtggggac caagttcatt    3480
acctccctat cagttctagc atagtaaact acggtaccag tgttagtggg aagagctggg    3540
ttttcctagt atacccactg catcctactc ctacctggtc aacccgctgc ttccaggtat    3600
```

```
gggacctgct aagtgtggaa ttacctgata agggagaggg aaatacaagg agggcctctg    3660
gtgttcctgg cctcagccag ctgcccacaa gccataaacc aataaaacaa gaatactgag    3720
tcagtttttt atctgggttc tcttcattcc cactgcactt ggtgctgctt tggctgactg    3780
ggaacacccc ataactacag agtctgacag gaagactgga gactgtccac ttctagctcg    3840
gaacttactg tgtaaataaa cttcagaac tgctaccatg aagtgaaaat gccacatttt    3900
gctttataat ttctacccat gttgggaaaa actggcttt tcccagccct ttccagggca     3960
taaaactcaa cccttcgat agcaagtccc atcagcctat tatttttta aagaaaactt      4020
gcacttgttt ttcttttttac agttacttcc ttcctgcccc aaaattataa actctaagtg   4080
taaaaaaaag tcttaacaac agcttcttgc ttgtaaaaat atgtattata catctgtatt    4140
tttaaattct gctcctgaaa aatgactgtc ccattctcca ctcactgcat ttggggcctt    4200
tcccattggt ctgcatgtct tttatcattg caggccagtg gacagaggga aagggagaa     4260
caggggtcgc caacacttgt gttgctttct gactgatcct gaacaagaaa gagtaacact    4320
gaggcgctcg ctcccatgca caactctcca aaacacttat cctcctgcaa gagtgggctt    4380
tccagggtct ttactgggaa gcagttaagc cccctcctca ccccttcctt ttttctttct    4440
ttactccttt ggcttcaaag gattttggaa aagaaacaat atgctttaca ctcattttca    4500
atttctaaat ttgcagggga tactgaaaaa tacggcaggt ggcctaaggc tgctgtaaag    4560
ttgaggggag aggaaatctt aagattacaa gataaaaaac gaatcccta aacaaaaaga     4620
acaatagaac tggtcttcca ttttgccacc tttcctgttc atgacagcta ctaacctgga   4680
gacagtaaca tttcattaac caaagaaagt gggtcacctg acctctgaag agctgagtac    4740
tcaggccact ccaatcaccc tacaagatgc caaggaggtc ccaggaagtc cagctcctta    4800
aactgacgct agtcaataaa cctgggcaag tgaggcaaga gaaatgagga agaatccatc    4860
tgtgaggtga caggcaagga tgaaagacaa agaaggaaaa gagtatcaaa ggcagaaagg    4920
agatcattta gttgggtctg aaaggaaaag tctttgctat ccgacatgta ctgctagtac    4980
ctgtaagcat tttaggtccc agaatggaaa aaaaaatcag ctattggtaa tataataatg    5040
tccttttccct ggagtcagtt tttttaaaaa gttaactctt agtttttact tgtttaattc   5100
taaaagagaa gggagctgag gccattccct gtaggagtaa agataaaagg ataggaaaag    5160
attcaaagct ctaatagagt cacagctttc ccaggtataa aacctaaaat taagaagtac    5220
aataagcaga ggtggaaaat gatctagttc ctgatagcta cccacagagc aagtgattta    5280
taaatttgaa atccaaacta ctttcttaat atcactttgg tctccatttt tcccaggaca    5340
ggaaatatgt cccccccctaa ctttcttgct tcaaaaatta aaatccagca tcccaagatc   5400
attctacaag taattttgca cagacatctc ctcaccccag tgcctgtctg gagctcaccc    5460
aaggtcacca aacaacttgg ttgtgaacca actgccttaa ccttctgggg gagggggatt    5520
agctagacta ggagaccaga agtgaatggg aaagggtgag gacttcacaa tgttggcctg    5580
tcagagcttg attagaagcc aagacagtgg cagcaaagga agacttggcc caggaaaaac    5640
ctgtgggttt tgctaatttc tgtccagaaa ataggggtgga cagaagcttg tggggtacat   5700
ggaggaattg ggacctggtt atgttgttat tctcggactg tgaattttgg tgatgtaaaa    5760
cagaatattc tgtaaaccta atgtctgtat aaataatgag cgttaacaca gtaaaatatt    5820
caataagaag tcaaaaaaaa aaaaaaaaaa                                      5850
```

<210> SEQ ID NO 18
<211> LENGTH: 5775
<212> TYPE: DNA

<213> ORGANISM: Homo sapiens

<400> SEQUENCE: 18

```
acaagtcttt ccgcctcccc agcccgcccg ggagctgcga gccgcgagct ggattatggt      60
ggcctgagca gccaacgcag ccgcaggagc ccggagccct tgcccctgcc cgcgccgccg     120
cccgccgggg ggaccaggga agccgccacc ggcccgccat gcccgcccct cccagccccg     180
ccgggagccc cgcgcccgctg cccaggctgg ccgccgccgt gccgatgtag cgggctccgg    240
atcccagcct ctcccctgct cccgtgctct gcggatctcc cctgaccgct ctccacagcc     300
cggaccgggg ggctggccca gggccctgca ggccctggcg tcctgatgcc cccaagctcc     360
ctctcctgag aagccaccag caccacccag acttgggggc aggcgccagg gacggacgtg     420
ggccagtgcg agcccagagg gcccgaaggc cggggcccac catggcccaa gccctgccct     480
ggctcctgct gtggatgggc gcgggagtgc tgcctgccca cggcacccag cacggcatcc     540
ggctgcccct gcgcagcggc ctgggggggcg cccccctggg gctgcggctg ccccgggaga    600
ccgacgaaga gcccgaggag cccggccgga ggggcagctt tgtggagatg gtggacaacc     660
tgaggggcaa gtcggggcag ggctactacg tggagatgac cgtgggcagc cccccgcaga    720
cgctcaacat cctggtggat acaggcagca gtaactttgc agtgggtgct gccccccacc    780
ccttcctgca tcgctactac cagaggcagc tgtccagcac ataccgggac tccggaagg     840
gtgtgtatgt gccctacacc cagggcaagt gggaaggggga gctgggcacc gacctggtaa     900
gcatccccca tggccccaac gtcactgtgc gtgccaacat tgctgccatc actgaatcag     960
acaagttctt catcaacggc tccaactggg aaggcatcct ggggctggcc tatgctgaga    1020
ttgccaggct ttgtggtgct ggcttccccc tcaaccagtc tgaagtgctg gcctctgtcg    1080
gagggagcat gatcattgga ggtatcgacc actcgctgta cacaggcagt ctctggtata    1140
cacccatccg gcgggagtgg tattatgagg tgatcattgt gcgggtggag atcaatggac    1200
aggatctgaa aatggactgc aaggagtaca actatgacaa gagcattgtg gacagtggca    1260
ccaccaacct tcgtttgccc aagaaagtgt ttgaagctgc agtcaaatcc atcaaggcag    1320
cctcctccac ggagaagttc cctgatggtt tctggctagg agagcagctg gtgtgctggc    1380
aagcaggcac cacccccttgg aacatttttcc cagtcatctc actctaccta atgggtgagg    1440
ttaccaacca gtccttccgc atcaccatcc ttccgcagca ataccctgcgg ccagtggaag    1500
atgtggccac gtcccaagac gactgttaca gtttgccat ctcacagtca tccacgggca    1560
ctgttatggg agctgttatc atggagggct tctacgttgt cttttgatcgg gcccgaaaac    1620
gaattggctt tgctgtcagc gcttgccatg tgcacgatga gttcaggacg gcagcggtgg    1680
aaggccctttt tgtcaccttg gacatggaag actgtggcta caacattcca cagacagatg    1740
agtcaaccct catgaccata gcctatgtca tggctgccat ctgcgccctc ttcatgctgc    1800
cactctgcct catggtgtgt cagtggcgct gcctccgctg cctgcgccag cagcatgatg    1860
actttgctga tgacatctcc ctgctgaagt gaggaggccc atgggcagaa gatagagatt    1920
cccctggacc acacctccgt ggttcacttt ggtcacaagt aggagacaca gatggcacct    1980
gtggccagag cacctcagga ccctccccac ccaccaaatg cctctgcctt gatggagaag    2040
gaaaaggctg gcaaggtggg ttccaggggac tgtacctgta ggaaacagaa aagagaagaa    2100
agaagcactc tgctggcggg aatactcttg gtcacctcaa atttaagtcg ggaaattctg    2160
ctgcttgaaa cttcagcccct gaaccttttgt ccaccattcc tttaaattct ccaacccaaa    2220
gtattcttct tttcttagtt tcagaagtac tggcatcaca cgcaggttac cttggcgtgt    2280
```

```
gtccctgtgg taccctggca gagaagagac caagcttgtt tccctgctgg ccaaagtcag   2340
taggagagga tgcacagttt gctatttgct ttagagacag ggactgtata aacaagccta   2400
acattggtgc aaagattgcc tcttgaatta aaaaaaaaaa ctagattgac tatttataca   2460
aatgggggcg gctggaaaga ggagaaggag agggagtaca aagacaggga atagtgggat   2520
caaagctagg aaaggcagaa acacaaccac tcaccagtcc tagttttaga cctcatctcc   2580
aagatagcat cccatctcag aagatgggtg ttgttttcaa tgttttcttt tctgtggttg   2640
cagcctgacc aaaagtgaga tgggaagggc ttatctagcc aaagagctct ttttagctc    2700 tcttaaatga agtgcccact aagaagttcc acttaacaca tgaatttctg ccatattaat   2760
ttcattgtct ctatctgaac cacccttat tctacatatg ataggcagca ctgaaatatc    2820
ctaaccccct aagctccagg tgccctgtgg gagagcaact ggactatagc agggctgggc   2880
tctgtcttcc tggtcatagg ctcactcttt cccccaaatc ttcctctgga gctttgcagc   2940
caaggtgcta aaaggaatag gtaggagacc tcttctatct aatccttaaa agcataatgt   3000
tgaacattca ttcaacagct gatgccctat aacccctgcc tggatttctt cctattaggc   3060
tataagaagt agcaagatct ttacataatt cagagtggtt tcattgcctt cctaccctct   3120
ctaatggccc ctccatttat ttgactaaag catcacacag tggcactagc attataccaa   3180
gagtatgaga aatacagtgc tttatggctc taacattact gccttcagta tcaaggctgc   3240
ctggagaaag gatggcagcc tcagggcttc cttatgtcct ccaccacaag agctccttga   3300
tgaaggtcat ctttttcccc tatcctgttc ttccccctcc cgctcctaat ggtacgtggg   3360
tacccaggct ggttcttggg ctaggtagtg gggaccaagt tcattacctc cctatcagtt   3420
ctagcatagt aaactacggt accagtgtta gtgggaagag ctgggttttc ctagtatacc   3480
cactgcatcc tactcctacc tggtcaaccc gctgcttcca ggtatgggac tgctaagtg    3540 tggaattacc tgataaggga gagggaaata caaggagggc ctctggtgtt cctggcctca   3600
gccagctgcc cacaagccat aaaccaataa aacaagaata ctgagtcagt ttttatctg    3660 ggttctcttc attcccactg cacttggtgc tgctttggct gactgggaac accccataac   3720
tacagagtct gacaggaaga ctggagactg tccacttcta gctcggaact tactgtgtaa   3780
ataaactttc agaactgcta ccatgaagtg aaaatgccac attttgcttt ataatttcta   3840
cccatgttgg gaaaaactgg ctttttccca gccctttcca gggcataaaa ctcaaccccct  3900 tcgatagcaa gtcccatcag cctattattt ttttaaagaa aacttgcact tgttttcttt   3960
tttacagtta cttccttcct gccccaaaat tataaactct aagtgtaaaa aaaagtctta   4020
acaacagctt cttgcttgta aaaatatgta ttatacatct gtattttaa attctgctcc    4080 tgaaaaatga ctgtcccatt ctccactcac tgcatttggg gcctttccca ttggtctgca   4140
tgtcttttat cattgcaggc cagtggacag agggagaagg gagaacaggg gtcgccaaca   4200
cttgtgttgc tttctgactg atcctgaaca agaaagagta acactgaggc gctcgctccc   4260
atgcacaact ctccaaaaca cttatcctcc tgcaagagtg ggctttccag ggtctttact   4320
gggaagcagt taagccccct cctcacccct tcctttttc tttctttact cctttggctt    4380
caaaggattt tggaaaagaa acaatatgct ttacactcat tttcaatttc taaatttgca   4440
ggggatactg aaaaatacgg caggtggcct aaggctgctg taaagttgag gggagaggaa   4500
atcttaagat tacaagataa aaaacgaatc ccctaaacaa aagaacaat agaactggtc     4560 ttccattttg ccacctttcc tgttcatgac agctactaac ctggagacag taacatttca   4620
ttaaccaaag aaagtgggtc acctgacctc tgaagagctg agtactcagg ccactccaat   4680
```

| | | | | |
|---|---|---|---|---|
| caccctacaa | gatgccaagg | aggtcccagg | aagtccagct | ccttaaactg acgctagtca | 4740 |
| ataaacctgg | gcaagtgagg | caagagaaat | gaggaagaat | ccatctgtga ggtgacaggc | 4800 |
| aaggatgaaa | gacaaagaag | gaaaagagta | tcaaaggcag | aaaggagatc atttagttgg | 4860 |
| gtctgaaagg | aaaagtcttt | gctatccgac | atgtactgct | agtacctgta agcattttag | 4920 |
| gtcccagaat | ggaaaaaaaa | atcagctatt | ggtaatataa | taatgtcctt tccctggagt | 4980 |
| cagttttttt | aaaagttaa | ctcttagttt | ttacttgttt | aattctaaaa gagaaggag | 5040 |
| ctgaggccat | tccctgtagg | agtaaagata | aaggatagg | aaaagattca aagctctaat | 5100 |
| agagtcacag | ctttcccagg | tataaaacct | aaaattaaga | agtacaataa gcagaggtgg | 5160 |
| aaaatgatct | agttcctgat | agctacccac | agagcaagtg | atttataaat ttgaaatcca | 5220 |
| aactactttc | ttaatatcac | tttggtctcc | attttttccca | ggacaggaaa tatgtccccc | 5280 |
| cctaactttc | ttgcttcaaa | aattaaaatc | cagcatccca | agatcattct acaagtaatt | 5340 |
| ttgcacagac | atctcctcac | cccagtgcct | gtctggagct | cacccaaggt caccaaacaa | 5400 |
| cttggttgtg | aaccaactgc | cttaaccttc | tggggaggg | ggattagcta gactaggaga | 5460 |
| ccagaagtga | atgggaaagg | gtgaggactt | cacaatgttg | gcctgtcaga gcttgattag | 5520 |
| aagccaagac | agtggcagca | aaggaagact | tggcccagga | aaaacctgtg ggttgtgcta | 5580 |
| atttctgtcc | agaaaatagg | gtggacagaa | gcttgtgggg | tacatggagg aattgggacc | 5640 |
| tggttatgtt | gttattctcg | gactgtgaat | tttggtgatg | taaaacagaa tattctgtaa | 5700 |
| acctaatgtc | tgtataaata | atgagcgtta | acacagtaaa | atattcaata agaagtcaaa | 5760 |
| aaaaaaaaaa | aaaaa | | | | 5775 |

<210> SEQ ID NO 19
<211> LENGTH: 5718
<212> TYPE: DNA
<213> ORGANISM: Homo sapiens

<400> SEQUENCE: 19

| | | | | |
|---|---|---|---|---|
| acaagtcttt | ccgcctcccc | agcccgcccg | ggagctgcga | gccgcgagct ggattatggt | 60 |
| ggcctgagca | gccaacgcag | ccgcaggagc | ccggagcccc | tgcccctgcc cgcgccgccg | 120 |
| cccgccgggg | ggaccaggga | agccgccacc | ggcccgccat | gcccgcccct cccagccccg | 180 |
| ccgggagccc | gcgcccgctg | cccaggctgg | ccgccgccgt | gccgatgtag cgggctccgg | 240 |
| atcccagcct | ctcccctgct | cccgtgctct | gcggatctcc | cctgaccgct ctccacagcc | 300 |
| cggacccggg | ggctggccca | gggccctgca | ggccctggcg | tcctgatgcc ccaagctcc | 360 |
| ctctcctgag | aagccaccag | caccacccag | acttgggggc | aggcgccagg gacggacgtg | 420 |
| ggccagtgcg | agcccagagg | gcccgaaggc | cggggcccac | catggcccaa gccctgccct | 480 |
| ggctcctgct | gtggatgggc | gcgggagtgc | tgcctgccca | cggcacccag cacggcatcc | 540 |
| ggctgccccct | gcgcagcggc | ctgggggcg | ccccctggg | gctgcggctg cccgggaga | 600 |
| ccgacgaaga | gcccgaggag | cccggccgga | ggggcagctt | tgtggagatg gtggacaacc | 660 |
| tgaggggcaa | gtcggggcag | ggctactacg | tggagatgac | cgtgggcagc cccccgcaga | 720 |
| cgctcaacat | cctggtggat | acaggcagca | gtaactttgc | agtgggtgct gccccccacc | 780 |
| ccttcctgca | tcgctactac | cagaggcagc | tgtccagcac | ataccgggac tccggaagg | 840 |
| gtgtgtatgt | gccctacacc | cagggcaagt | gggaagggga | gctgggcacc gacctgcctg | 900 |
| acgactccct | ggagcttttc | tttgactctc | tggtaaagca | gacccacgtt cccaacctct | 960 |
| tctccctgca | gctttgtggt | gctggcttcc | ccctcaacca | gtctgaagtg ctggcctctg | 1020 |

```
tcggagggag catgatcatt ggaggtatcg accactcgct gtacacaggc agtctctggt    1080
atacacccat ccggcgggag tggtattatg aggtgatcat tgtgcgggtg agatcaatg     1140 gacaggatct gaaaatggac tgcaaggagt acaactatga caagagcatt gtggacagtg    1200
gcaccaccaa ccttcgtttg cccaagaaag tgtttgaagc tgcagtcaaa tccatcaagg    1260
cagcctcctc cacggagaag ttccctgatg gtttctggct aggagagcag ctggtgtgct    1320
ggcaagcagg caccacccct tggaacattt tcccagtcat ctcactctac ctaatgggtg    1380
aggttaccaa ccagtccttc cgcatcacca tccttccgca gcaatacctg cggccagtgg    1440
aagatgtggc cacgtcccaa gacgactgtt acaagtttgc catctcacag tcatccacgg    1500
gcactgttat gggagctgtt atcatggagg gcttctacgt tgtctttgat cgggcccgaa    1560
aacgaattgg ctttgctgtc agcgcttgcc atgtgcacga tgagttcagg acggcagcgg    1620
tggaaggccc ttttgtcacc ttggacatgg aagactgtgg ctacaacatt ccacagacag    1680
atgagtcaac cctcatgacc atagcctatg tcatggctgc catctgcgcc ctcttcatgc    1740
tgccactctg cctcatggtg tgtcagtggc gctgcctccg ctgcctgcgc cagcagcatg    1800
atgactttgc tgatgacatc tccctgctga agtgaggagg cccatgggca aagatagag    1860 attcccctgg accacacctc cgtggttcac tttggtcaca gtaggagac acagatggca    1920 cctgtggcca gagcacctca ggaccctccc cacccaccaa atgcctctgc cttgatggag    1980
aaggaaaagg ctggcaaggt gggttccagg gactgtacct gtaggaaaca gaaagagaa     2040 gaaagaagca ctctgctggc gggaatactc ttggtcacct caaatttaag tcgggaaatt    2100
ctgctgcttg aaacttcagc cctgaacctt tgtccaccat tcctttaaat tctccaaccc    2160
aaagtattct tcttttctta gtttcagaag tactggcatc acacgcaggt taccttggcg    2220
tgtgtccctg tggtaccctg gcagagaaga gaccaagctt gtttccctgc tggccaaagt    2280
cagtaggaga ggatgcacag tttgctattt gctttagaga cagggactgt ataaacaagc    2340
ctaacattgg tgcaaagatt gcctcttgaa ttaaaaaaaa aaactagatt gactatttat    2400
acaaatgggg gcggctggaa agaggagaag gagagggagt acaaagacag ggaatagtgg    2460
gatcaaagct aggaaaggca gaaacacaac cactcaccag tcctagtttt agacctcatc    2520
tccaagatag catcccatct cagaagatgg gtgttgtttt caatgttttc ttttctgtgg    2580
ttgcagcctg accaaaagtg agatgggaag ggcttatcta gccaaagagc tcttttttag    2640
ctctcttaaa tgaagtgccc actaagaagt tccacttaac acatgaattt ctgccatatt    2700
aatttcattg tctctatctg aaccacccett tattctacat atgataggca gcactgaaat    2760
atcctaaccc cctaagctcc aggtgccctg tgggagagca actggactat agcagggctg    2820
ggctctgtct tcctggtcat aggctcactc tttcccccaa atcttcctct ggagctttgc    2880
agccaaggtg ctaaaaggaa taggtaggag acctcttcta tctaatcctt aaaagcataa    2940
tgttgaacat tcattcaaca gctgatgccc tataacccct gcctggattt cttcctatta    3000
ggctataaga agtagcaaga tctttacata attcagagtg gtttcattgc cttcctaccc    3060
tctctaatgg cccctccatt tatttgacta aagcatcaca cagtggcact agcattatac    3120
caagagtatg agaaatacag tgctttatgg ctctaacatt actgccttca gtatcaaggc    3180
tgcctggaga aaggatggca gcctcagggc ttccttatgt cctccaccac aagagctcct    3240
tgatgaaggt catcttttc ccctatcctg ttcttcccct cccgctcct aatggtacgt      3300 gggtacccag gctggttctt gggctaggta gtggggacca agttcattac ctccctatca    3360
gttctagcat agtaaactac ggtaccagtg ttagtgggaa gagctgggtt ttcctagtat    3420
```

```
acccactgca tcctactcct acctggtcaa cccgctgctt ccaggtatgg gacctgctaa    3480
gtgtggaatt acctgataag ggagagggaa atacaaggag ggcctctggt gttcctggcc    3540
tcagccagct gcccacaagc cataaaccaa taaaacaaga atactgagtc agtttttat    3600 ctgggttctc ttcattccca ctgcacttgg tgctgctttg gctgactggg aacaccccat    3660
aactacagag tctgacagga agactggaga ctgtccactt ctagctcgga acttactgtg    3720
taaataaact ttcagaactg ctaccatgaa gtgaaaatgc cacattttgc tttataattt    3780
ctacccatgt tgggaaaaac tggcttttt ccagcccttt ccagggcata aaactcaacc    3840
ccttcgatag caagtcccat cagcctatta ttttttaaa gaaaacttgc acttgttttt    3900 cttttacag ttacttcctt cctgccccaa aattataaac tctaagtgta aaaaaaagtc    3960
ttaacaacag cttcttgctt gtaaaaatat gtattataca tctgtatttt taaattctgc    4020
tcctgaaaaa tgactgtccc attctccact cactgcattt ggggcctttc ccattggtct    4080
gcatgtcttt tatcattgca ggccagtgga cagagggaga agggagaaca ggggtcgcca    4140
acacttgtgt tgctttctga ctgatcctga acaagaaaga gtaacactga ggcgctcgct    4200
cccatgcaca actctccaaa acacttatcc tcctgcaaga gtgggctttc cagggtcttt    4260
actgggaagc agttaagccc cctcctcacc ccttccttt ttctttcttt actcctttgg    4320
cttcaaagga ttttggaaaa gaaacaatat gctttacact cattttcaat ttctaaattt    4380 gcagggata ctgaaaaata cggcaggtgg cctaaggctg ctgtaaagtt gaggggagag    4440
gaaatcttaa gattcaaga taaaaaacga atccccctaaa caaaaagaac aatagaactg    4500
gtcttccatt ttgccacctt tcctgttcat gacagctact aacctggaga cagtaacatt    4560
tcattaacca aagaaagtgg gtcacctgac ctctgaagag ctgagtactc aggccactcc    4620
aatcacccta caagatgcca aggaggtccc aggaagtcca gctccttaaa ctgacgctag    4680
tcaataaacc tgggcaagtg aggcaagaga aatgaggaag aatccatctg tgaggtgaca    4740
ggcaaggatg aaagacaaag aaggaaaaga gtatcaaagg cagaaaggag atcatttagt    4800
tgggtctgaa aggaaaagtc tttgctatcc gacatgtact gctagtacct gtaagcattt    4860
taggtcccag aatggaaaaa aaaatcagct attggtaata taataatgtc cttttccctgg   4920 agtcagtttt tttaaaaagt taactcttag ttttttacttg tttaattcta aaagagaagg    4980
gagctgaggc cattccctgt aggagtaaag ataaaaggat aggaaaagat tcaaagctct    5040
aatagagtca cagctttccc aggtataaaa cctaaaatta agaagtacaa taagcagagg    5100
tggaaaatga tctagttcct gatagctacc cacagagcaa gtgatttata aatttgaaat    5160
ccaaactact ttcttaatat cactttggtc tccatttttc ccaggacagg aaatatgtcc    5220
ccccctaact ttcttgcttc aaaaattaaa atccagcatc ccaagatcat tctacaagta    5280
attttgcaca gacatctcct caccccagtg cctgtctgga gctcacccaa ggtcaccaaa    5340
caacttggtt gtgaaccaac tgccttaacc ttctggggga gggggattag ctagactagg    5400
agaccagaag tgaatgggaa agggtgagga cttcacaatg ttggcctgtc agagcttgat    5460
tagaagccaa gacagtggca gcaaggaag acttggccca ggaaaaacct gtgggttgtg    5520
ctaatttctg tccagaaaat agggtggaca gaagcttgtg gggtacatgg aggaattggg    5580
acctggttat gttgttattc tcggactgtg aattttggtg atgtaaaaca gaatattctg    5640
taaacctaat gtctgtataa ataatgagcg ttaacacagt aaaatattca ataagaagtc    5700 aaaaaaaaa aaaaaaaa                                                   5718
```

<210> SEQ ID NO 20

<211> LENGTH: 5643
<212> TYPE: DNA
<213> ORGANISM: Homo sapiens

<400> SEQUENCE: 20

```
acaagtcttt ccgcctcccc agcccgcccg ggagctgcga gccgcgagct ggattatggt      60
ggcctgagca gccaacgcag ccgcaggagc ccggagccct tgcccctgcc cgcgccgccg     120
cccgccgggg ggaccaggga agccgccacc ggcccgccat gcccgcccct ccagccccg     180
ccgggagccc gcgcccgctg cccaggctgg ccgccgccgt gccgatgtag cgggctccgg     240
atcccagcct ctcccctgct cccgtgctct gcggatctcc cctgaccgct ctccacagcc     300
cggacccggg ggctggccca gggccctgca ggccctggcg tcctgatgcc cccaagctcc     360
ctctcctgag aagccaccag caccacccag acttggggc aggcgccagg acgacgtg      420
ggccagtgcg agcccagagg gcccgaaggc cggggcccac catggcccaa gccctgccct     480
ggctcctgct gtggatgggc gcgggagtgc tgcctgccca cggcacccag cacggcatcc     540
ggctgcccct gcgcagcggc ctgggggggcg ccccctggg gctgcggctg ccccgggaga     600
ccgacgaaga gcccgaggag cccggccgga ggggcagctt tgtggagatg gtggacaacc     660
tgagggcaa gtcgggggcag ggctactacg tggagatgac cgtgggcagc cccccgcaga    720
cgctcaacat cctggtggat acaggcagca gtaactttgc agtgggtgct gccccccacc     780
ccttcctgca tcgctactac cagaggcagc tgtccagcac ataccgggac tccggaagg      840
gtgtgtatgt gccctacacc cagggcaagt gggaaggggaa gctgggcacc gacctgcttt     900
gtggtgctgg cttccccctc aaccagtctg aagtgctggc ctctgtcgga gggagcatga    960
tcattggagg tatcgaccac tcgctgtaca caggcagtct ctggtataca cccatccggc   1020
gggagtggta ttatgaggtg atcattgtgc gggtggagat caatggacag gatctgaaaa   1080
tggactgcaa ggagtacaac tatgacaaga gcattgtgga cagtggcacc accaaccttc   1140
gtttgcccaa gaaagtgttt gaagctgcag tcaaatccat caaggcagcc tcctccacgg   1200
agaagttccc tgatggtttc tggctaggag agcagctggt gtgctggcaa gcaggcacca   1260
ccccttggaa cattttccca gtcatctcac tctacctaat gggtgaggtt accaaccagt   1320
ccttccgcat caccatcctt ccgcagcaat acctgcggcc agtggaagat gtggccacgt   1380
cccaagacga ctgttacaag tttgccatct cacagtcatc cacgggcact gttatgggag   1440
ctgttatcat ggaggctcttc tacgttgtct ttgatcgggc ccgaaaacga attggctttg   1500
ctgtcagcgc ttgccatgtg cacgatgagt tcaggacggc agcggtggaa ggccctttg    1560
tcaccttgga catggaagac tgtggctaca cattccaca gacagatgag tcaaccctca   1620
tgaccatagc ctatgtcatg gctgccatct gcgccctctt catgctgcca ctctgcctca   1680
tggtgtgtca gtggcgctgc ctccgctgcc tgcgccagca gcatgatgac tttgctgatg   1740
acatctccct gctgaagtga ggaggcccat gggcagaaga tagagattcc cctgaccac    1800
acctccgtgg ttcactttgg tcacaagtag agacacaga tggcacctgt ggccagagca   1860
cctcaggacc ctccccaccc accaaatgcc tctgccttga tggagaagga aaaggctggc   1920
aaggtgggtt ccagggactg tacctgtagg aaacagaaaa gagaagaaag aagcactctg   1980
ctggcgggaa tactcttggt cacctcaaat ttaagtcggg aaattctgct gcttgaaact   2040
tcagccctga acctttgtcc accattcctt taaattctcc aacccaaagt attcttcttt   2100
tcttagtttc agaagtactg gcatcacacg caggttacct tggcgtgtgt ccctgtggta   2160
ccctggcaga gaagagacca agcttgtttc cctgctggcc aaagtcagta ggagaggatg   2220
```

```
cacagtttgc tatttgcttt agagacaggg actgtataaa caagcctaac attggtgcaa    2280
agattgcctc ttgaattaaa aaaaaaaact agattgacta tttatacaaa tgggggcggc    2340
tggaaagagg agaaggagag ggagtacaaa gacagggaat agtgggatca aagctaggaa    2400
aggcagaaac acaaccactc accagtccta gttttagacc tcatctccaa gatagcatcc    2460
catctcagaa gatgggtgtt gttttcaatg ttttctttc tgtggttgca gcctgaccaa    2520
aagtgagatg ggaagggctt atctagccaa agagctcttt tttagctctc ttaaatgaag    2580
tgcccactaa gaagttccac ttaacacatg aatttctgcc atattaattt cattgtctct    2640
atctgaacca ccctttattc tacatatgat aggcagcact gaaatatcct aaccccctaa    2700
gctccaggtg ccctgtggga gagcaactgg actatagcag ggctgggctc tgtcttcctg    2760
gtcataggct cactctttcc cccaaatctt cctctggagc tttgcagcca aggtgctaaa    2820
aggaataggt aggagacctc ttctatctaa tccttaaaag cataatgttg aacattcatt    2880
caacagctga tgccctataa cccctgcctg gatttcttcc tattaggcta taagaagtag    2940
caagatcttt acataattca gagtggtttc attgccttcc taccctctct aatggcccct    3000
ccatttattt gactaaagca tcacacagtg gcactagcat tataccaaga gtatgagaaa    3060
tacagtgctt tatggctcta acattactgc cttcagtatc aaggctgcct ggagaaagga    3120
tggcagcctc agggcttcct tatgtcctcc accacaagag ctccttgatg aaggtcatct    3180 ttttcccta tcctgttctt cccctcccg ctcctaatgg tacgtgggta cccaggctgg    3240
ttcttgggct aggtagtggg gaccaagttc attacctccc tatcagttct agcatagtaa    3300
actacggtac cagtgttagt gggaagagct gggttttcct agtatacca ctgcatccta    3360 ctcctacctg gtcaacccgc tgcttccagg tatgggacct gctaagtgtg gaattacctg    3420
ataagggaga gggaaataca aggagggcct ctggtgttcc tggcctcagc cagctgccca    3480
caagccataa accataaaaa caagaatact gagtcagttt tttatctggg ttctcttcat    3540
tcccactgca cttggtgctg ctttggctga ctgggaacac cccataacta cagagtctga    3600
caggaagact ggagactgtc cacttctagc tcggaactta ctgtgtaaat aaactttcag    3660
aactgctacc atgaagtgaa aatgccacat tttgctttat aatttctacc catgttggga    3720
aaaactggct ttttcccagc cctttccagg gcataaaact caaccccttc gatagcaagt    3780
cccatcagcc tattattttt ttaaagaaaa cttgcacttg ttttcttttt tacagttact    3840
tccttcctgc cccaaaatta taaactctaa gtgtaaaaaa aagtcttaac aacagcttct    3900
tgcttgtaaa aatatgtatt atacatctgt atttttaaat tctgctcctg aaaaatgact    3960
gtcccattct ccactcactg catttggggc ctttcccatt ggtctgcatg tcttttatca    4020
ttgcaggcca gtgacagag ggagaaggga aacaggggt cgccaacact tgtgttgctt    4080
tctgactgat cctgaacaag aaagagtaac actgaggcgc tcgctcccat gcacaactct    4140
ccaaaacact tatcctcctg caagagtggg ctttccaggg tctttactgg gaagcagtta    4200 agcccctcc tcacccttc ctttttctt tctttactcc tttggcttca aaggattttg    4260
gaaaagaaac aatatgcttt acactcattt tcaatttcta aatttgcagg ggatactgaa    4320
aaatacggca ggtggcctaa ggctgctgta aagttgaggg gagaggaaat cttaagatta    4380
caagataaaa aacgaatccc ctaaacaaaa agaacaatag aactggtctt ccattttgcc    4440
acctttcctg ttcatgacag ctactaacct ggagacagta acatttcatt aaccaaagaa    4500
agtgggtcac ctgacctctg aagagctgag tactcaggcc actccaatca ccctacaaga    4560
tgccaaggag gtcccaggaa gtccagctcc ttaaactgac gctagtcaat aaacctgggc    4620
```

| | |
|---|---|
| aagtgaggca agagaaatga ggaagaatcc atctgtgagg tgacaggcaa ggatgaaaga | 4680 |
| caaagaagga aaagagtatc aaaggcagaa aggagatcat ttagttgggt ctgaaaggaa | 4740 |
| aagtctttgc tatccgacat gtactgctag tacctgtaag cattttaggt cccagaatgg | 4800 |
| aaaaaaaaat cagctattgg taatataata atgtcctttc cctggagtca gttttttaa | 4860 |
| aaagttaact cttagttttt acttgtttaa ttctaaaaga aagggagct gaggccattc | 4920 |
| cctgtaggag taaagataaa aggataggaa aagattcaaa gctctaatag agtcacagct | 4980 |
| ttcccaggta taaaacctaa aattaagaag tacaataagc agaggtggaa aatgatctag | 5040 |
| ttcctgatag ctacccacag agcaagtgat ttataaattt gaaatccaaa ctactttctt | 5100 |
| aatatcactt tggtctccat ttttcccagg acaggaaata tgtccccccc taactttctt | 5160 |
| gcttcaaaaa ttaaaatcca gcatcccaag atcattctac aagtaatttt gcacagacat | 5220 |
| ctcctcaccc cagtgcctgt ctggagctca cccaaggtca ccaaacaact tggttgtgaa | 5280 |
| ccaactgcct taaccttctg ggggagggg attagctaga ctaggagacc agaagtgaat | 5340 |
| gggaagggt gaggacttca caatgttggc ctgtcagagc ttgattagaa gccaagacag | 5400 |
| tggcagcaaa ggaagacttg gcccaggaaa aacctgtggg ttgtgctaat ttctgtccag | 5460 |
| aaaatagggt ggacagaagc ttgtgggta catggaggaa ttgggacctg gttatgttgt | 5520 |
| tattctcgga ctgtgaattt tggtgatgta aaacagaata ttctgtaaac ctaatgtctg | 5580 |
| tataataat gagcgttaac acagtaaaat attcaataag aagtcaaaaa aaaaaaaaaa | 5640 |
| aaa | 5643 |

<210> SEQ ID NO 21
<211> LENGTH: 1543
<212> TYPE: DNA
<213> ORGANISM: Homo sapiens

<400> SEQUENCE: 21

| | |
|---|---|
| ggagtggcca ttcgacgaca gtgtggtgta aaggaattca ttagccatgg atgtattcat | 60 |
| gaaaggactt tcaaaggcca aggagggagt tgtggctgct gctgagaaaa ccaaacaggg | 120 |
| tgtggcagaa gcagcaggaa agacaaaaga gggtgttctc tatgtaggct ccaaaaccaa | 180 |
| ggagggagtg gtgcatggtg tggcaacagt ggctgagaag accaaagagc aagtgacaaa | 240 |
| tgttggagga gcagtggtga cgggtgtgac agcagtagcc cagaagacag tggagggagc | 300 |
| agggagcatt gcagcagcca ctggctttgt caaaaaggac cagttgggca agaatgaaga | 360 |
| aggagcccca caggaaggaa ttctggaaga tatgcctgtg gatcctgaca atgaggctta | 420 |
| tgaaatgcct tctgaggaag ggtatcaaga ctacgaacct gaagcctaag aaatatcttt | 480 |
| gctcccagtt tcttgagatc tgctgacaga tgttccatcc tgtacaagtg ctcagttcca | 540 |
| atgtgcccag tcatgacatt tctcaaagtt tttacagtgt atctcgaagt cttccatcag | 600 |
| cagtgattga agtatctgta cctgcccccca ctcagcattt cggtgcttcc ctttcactga | 660 |
| agtgaataca tggtagcagg gtctttgtgt gctgtggatt ttgtggcttc aatctacgat | 720 |
| gttaaaacaa attaaaaaca cctaagtgac taccacttat ttctaaatcc tcactatttt | 780 |
| tttgttgctg ttgttcagaa gttgttagtg atttgctatc atatattata agatttttag | 840 |
| gtgtctttta atgatactgt ctaagaataa tgacgtattg tgaaatttgt taatatatat | 900 |
| aatacttaaa aatatgtgag catgaaacta tgcacctata aatactaaat atgaaatttt | 960 |
| accattttgc gatgtgttt attcacttgt gtttgtatat aaatggtgag aattaaaata | 1020 |
| aaacgttatc tcattgcaaa aatatttat ttttatccca tctcacttta ataataaaaa | 1080 |

| | |
|---|---|
| tcatgcttat aagcaacatg aattaagaac tgacacaaag gacaaaaata taaagttatt | 1140 |
| aatagccatt tgaagaagga ggaattttag aagaggtaga gaaaatgaa cattaaccct | 1200 |
| acactcggaa ttccctgaag caacactgcc agaagtgtgt tttggtatgc actggttcct | 1260 |
| taagtggctg tgattaatta ttgaaagtgg ggtgttgaag accccaacta ctattgtaga | 1320 |
| gtggtctatt tctcccttca atcctgtcaa tgtttgcttt atgtattttg gggaactgtt | 1380 |
| gtttgatgtg tatgtgttta taattgttat acattttta ttgagccttt tattaacata | 1440 |
| tattgttatt tttgtctcga ataattttt tagttaaaat ctattttgtc tgatattggt | 1500 |
| gtgaatgctg tacctttctg acaataaata atattcgacc atg | 1543 |

<210> SEQ ID NO 22
<211> LENGTH: 1096
<212> TYPE: DNA
<213> ORGANISM: Homo sapiens

<400> SEQUENCE: 22

| | |
|---|---|
| gaattcatta gccatggatg tattcatgaa aggactttca aaggccaagg agggagttgt | 60 |
| ggctgctgct gagaaaacca acagggtgt ggcagaagca gcaggaaaga caaaagaggg | 120 |
| tgttctctat gtaggctcca aaaccaagga gggagtggtg catggtgtgg caacagtggc | 180 |
| tgagaagacc aaaagcaag tgacaaatgt tggaggagca gtggtgacgg tgtgacagc | 240 |
| agtagcccag aagacagtgg agggagcagg gagcattgca gcagccactg ctttgtcaa | 300 |
| aaaggaccag ttgggcaagg aagggtatca agactacgaa cctgaagcct aagaaatatc | 360 |
| tttgctccca gtttcttgag atctgctgac agatgttcca tcctgtacaa gtgctcagtt | 420 |
| ccaatgtgcc cagtcatgac atttctcaaa gttttacag tgtatctcga agtcttccat | 480 |
| cagcagtgat tgaagtatct gtacctgccc ccactcagca tttcggtgct tcccttcac | 540 |
| tgaagtgaat acatggtagc agggtctttg tgtgctgtgg attttgtggc ttcaatctac | 600 |
| gatgttaaaa caaattaaaa acacctaagt gactaccact tatttctaaa tcctcactat | 660 |
| tttttttgttg ctgttgttca gaagttgtta gtgatttgct atcatatatt ataagatttt | 720 |
| taggtgtctt ttaatgatac tgtctaagaa taatgacgta ttgtgaaatt tgttaatata | 780 |
| tataatactt aaaaatatgt gagcatgaaa ctatgcacct ataaatacta aatatgaaat | 840 |
| tttaccattt tgcgatgtgt tttattcact tgtgtttgta tataaatggt gagaattaaa | 900 |
| ataaaacgtt atctcattgc aaaaatattt tatttttatc ccatctcact ttaataataa | 960 |
| aaatcatgct tataagcaac atgaattaag aactgacaca aaggacaaaa atataaagtt | 1020 |
| attaatagcc atttgaagaa ggaggaattt tagaagaggt agagaaaatg gaacattaac | 1080 |
| cctacactcg gaattc | 1096 |

<210> SEQ ID NO 23
<211> LENGTH: 981
<212> TYPE: DNA
<213> ORGANISM: Homo sapiens

<400> SEQUENCE: 23

| | |
|---|---|
| gtttggggcc agagtgggcg aggcgcggag gtctggccta taaagtagtc gcggagacgg | 60 |
| ggtgctggtt tgcgtcgtag tctcctgcag cgtctgggt ttccgttgca gtcctcggaa | 120 |
| ccaggacctc ggcgtggcct agcgagttat ggcgacgaag gccgtgtgcg tgctgaaggg | 180 |
| cgacggccca gtgcagggca tcatcaattt cgagcagaag gaaagtaatg gaccagtgaa | 240 |
| ggtgtgggga agcattaaag gactgactga aggcctgcat ggattccatg ttcatgagtt | 300 |

```
tggagataat acagcaggct gtaccagtgc aggtcctcac tttaatcctc tatccagaaa      360
acacggtggg ccaaaggatg aagagaggca tgttggagac ttgggcaatg tgactgctga      420
caaagatggt gtggccgatg tgtctattga agattctgtg atctcactct caggagacca      480
ttgcatcatt ggccgcacac tggtggtcca tgaaaaagca gatgacttgg gcaaaggtgg      540
aaatgaagaa agtacaaaga caggaaacgc tggaagtcgt ttggcttgtg gtgtaattgg      600
gatcgcccaa taaacattcc cttggatgta gtctgaggcc ccttaactca tctgttatcc      660
tgctagctgt agaaatgtat cctgataaac attaaacact gtaatcttaa aagtgtaatt      720
gtgtgacttt ttcagagttg ctttaaagta cctgtagtga gaaactgatt tatgatcact      780
tggaagattt gtatagtttt ataaaactca gttaaaatgt ctgtttcaat gacctgtatt      840
ttgccagact taaatcacag atgggtatta aacttgtcag aatttctttg tcattcaagc      900
ctgtgaataa aaaccctgta tggcacttat tatgaggcta ttaaaagaat ccaaattcaa      960
actaaaaaaa aaaaaaaaa a                                                 981

<210> SEQ ID NO 24
<211> LENGTH: 4247
<212> TYPE: DNA
<213> ORGANISM: Homo sapiens

<400> SEQUENCE: 24
gttccccaac tgctgtttta ttgtgctatt catgcctaga catcacatag ctagaaaggc       60
ccatcagacc cctcaggcca ctgctgttcc tgtcacacat tcctgcaaag gaccatgttg      120
ctaacttgaa aaaattact attaattaca cttgcagttg ttgcttagta acatttatga      180
ttttgtgttt ctcgtgacag catgagcaga gatcattaaa aattaaactt acaaagctgc      240
taaagtggga agaaggagaa cttgaagcca caattttgc acttgcttag aagccatcta      300
atctcaggtt tatatgctag atcttggggg aaacactgca tgtctctggt ttatattaaa      360
ccacatacag cacactactg acactgattt gtgtctggtg cagctggagt ttatcaccaa      420
gacataaaaa aaccttgacc ctgcagaatg gcctggaatt acaatcagat gggccacatg      480
gcatcccggt gaaagaaagc cctaaccagt ttttctgtctt gtttctgctt tctccctaca      540
gttccaccag gtgagaagag tgatgaccat cctttccttt actatggtta tttcatactt      600
tggttgcatg aaggctgccc ccatgaaaga agcaaacatc cgaggacaag gtggcttggc      660
ctacccaggt gtgcggaccc atgggactct ggagagcgtg aatgggccca aggcaggttc      720
aagaggcttg acatcattgg ctgacacttt cgaacacgtg atagaagagc tgttggatga      780
ggaccagaaa gttcggccca tgaagaaaa caataaggac gcagacttgt acacgtccag      840
ggtgatgctc agtagtcaag tgcctttgga gcctcctctt ctctttctgc tggaggaata      900
caaaaattac ctagatgctg caaacatgtc catgagggtc cggcgccact ctgaccctgc      960
ccgccgaggg gagctgagcg tgtgtgacag tattagtgag tgggtaacgg cggcagacaa     1020
aaagactgca gtggacatgt cgggcgggac ggtcacagtc cttgaaaagg tccctgtatc     1080
aaaaggccaa ctgaagcaat acttctacga gaccaagtgc aatcccatgg gttacacaaa     1140
agaaggctgc aggggcatag acaaaaggca ttggaactcc cagtgccgaa ctacccagtc     1200
gtacgtgcgg gcccttacca tggatagcaa aagagaatt ggctggcgat tcataaggat     1260
agacacttct tgtgtatgta cattgaccat taaaggggga agatagtgga tttatgttgt     1320
atagattaga ttatattgag acaaaaatta tctatttgta tatatacata cagggtaaa     1380 ttattcagtt aagaaaaaaa taattttatg aactgcatgt ataaatgaag tttatacagt     1440
```

```
acagtggttc tacaatctat ttattggaca tgtccatgac cagaagggaa acagtcattt    1500
gcgcacaact taaaaagtct gcattacatt ccttgataat gttgtggttt gttgccgttg    1560
ccaagaactg aaaacataaa aagttaaaaa aaataataaa ttgcatgctg ctttaattgt    1620
gaattgataa taaactgtcc tctttcagaa aacagaaaaa aaacacacac acacacaaca    1680
aaaatttgaa ccaaaacatt ccgtttacat tttagacagt aagtatcttc gttcttgtta    1740
gtactatatc tgtttttactg cttttaactt ctgatagcgt tggaattaaa acaatgtcaa    1800
ggtgctgttg tcattgcttt actggcttag gggatggggg atgggggta tattttttgtt    1860 tgttttgtgt tttttttttcg tttgtttgtt ttgttttttta gttcccacag ggagtagaga    1920
tggggaaaga attcctacaa tatatattct ggctgataaa agatacattt gtatgttgtg    1980
aagatgtttg caatatcgat cagatgacta gaaagtgaat aaaaattaag gcaactgaac    2040
aaaaaaatgc tcacactcca catcccgtga tgcacctccc aggccccgct cattctttgg    2100
gcgttggtca gagtaagctg cttttgacgg aaggacctat gtttgctcag aacacattct    2160
ttccccccct cccctctgg tctcctcttt gttttgtttt aaggaagaaa aatcagttgc    2220
gcgttctgaa atattttacc actgctgtga acaagtgaac acattgtgtc acatcatgac    2280
actcgtataa gcatggagaa cagtgatttt ttttttagaac agaaacaac aaaaaataac    2340 cccaaaatga agattatttt ttatgaggag tgaacatttg ggtaaatcat ggctaagctt    2400
aaaaaaaact catggtgagg cttaacaatg tcttgtaagc aaaaggtaga gccctgtatc    2460
aacccagaaa cacctagatc agaacaggaa tccacattgc cagtgacatg agactgaaca    2520
gccaaatgga ggctatgtgg agttggcatt gcatttaccg gcagtgcggg aggaatttct    2580
gagtggccat cccaaggtct aggtggaggt ggggcatggt atttgagaca ttccaaaacg    2640
aaggcctctg aaggaccctt cagaggtggc tctggaatga catgtgtcaa gctgcttgga    2700
cctcgtgctt taagtgccta cattatctaa ctgtgctcaa gaggttctcg actggaggac    2760
cacactcaag ccgacttatg cccaccatcc cacctctgga taattttgca taaaattgga    2820
ttagcctgga gcaggttggg agccaaatgt ggcatttgtg atcatgagat tgatgcaatg    2880
agatagaaga tgtttgctac ctgaaacactt attgctttga aactagactt gaggaaacca    2940
gggtttatct tttgagaact tttggtaagg gaaagggaa caggaaaaga accccaaac    3000 tcaggccgaa tgatcaaggg gacccatagg aaatcttgtc cagagacaag acttcgggaa    3060
ggtgtctgga cattcagaac accaagactt gaaggtgcct tgctcaatgg aagaggccag    3120
gacagagctg acaaaatttt gctccccagt gaaggccaca gcaaccttct gcccatcctg    3180
tctgttcatg gagagggtcc ctgcctcacc tctgccattt tgggttagga aagtcaagt    3240 tgggagcctg aaatagtggt tcttggaaaa atggatcccc agtgaaaact agagctctaa    3300
gcccattcag cccatttcac acctgaaaat gttagtgatc accacttgga ccagcatcct    3360
taagtatcag aaagccccaa gcaattgctg catcttagta gggtgaggga taagcaaaag    3420
aggatgttca ccataaccca ggaatgaaga taccatcagc aaagaatttc aatttgttca    3480
gtctttcatt tagagctagt cttttcacagt accatctgaa tacctctttg aaagaaggaa    3540
gactttacgt agtgtagatt tgttttgtgt tgtttgaaaa tattatcttt gtaattatttt    3600 ttaatatgta aggaatgctt ggaatatctg ctatatgtca actttatgca gcttcctttt    3660
gagggacaaa tttaaaacaa acaacccccc atcacaaact taaggattg caagggccag    3720 atctgttaag tggtttcata ggagacacat ccagcaattg tgtggtcagt ggctcttttta    3780 cccaataaga tacatcacag tcacatgctt gatggtttat gttgacctaa gatttatttt    3840
```

-continued

| | |
|---|---|
| gttaaaatct ctctctgttg tgttcgttct tgttctgttt tgttttgttt tttaaagtct | 3900 |
| tgctgtggtc tctttgtggc agaagtgttt catgcatggc agcaggcctg ttgctttttt | 3960 |
| atggcgattc ccattgaaaa tgtaagtaaa tgtctgtggc cttgttctct ctatggtaaa | 4020 |
| gatattattc accatgtaaa acaaaaaaca atatttattg tattttagta tatttatata | 4080 |
| attatgttat tgaaaaaaat tggcattaaa acttaaccgc atcagaacct attgtaaata | 4140 |
| caagttctat ttaagtgtac taattaacat ataatatatg ttttaaatat agaattttta | 4200 |
| atgtttttaa atatattttc aaagtacata aaaaaaaaaa aaaaaaa | 4247 |

<210> SEQ ID NO 25
<211> LENGTH: 4084
<212> TYPE: DNA
<213> ORGANISM: Homo sapiens

<400> SEQUENCE: 25

| | |
|---|---|
| gtgtgtaatc cgggcgatag gagtccattc agcaccttgg acagagccaa cggatttgtc | 60 |
| cgaggtggcg gtaccccag gtagtcttct tggccccgct gtaaagccaa ccctgtgtcg | 120 |
| cccttaaaaa gcgtcttttc tgaggttcgg ctcacactga gatcggggct ggagagagag | 180 |
| tcagattttg gagcggagcg tttggaaagc gagccccagt ttggtcccct cattgagctc | 240 |
| gctgaagttg gcttcctagc ggtgtaggct ggaatagact cttggcaagc tccgggttgg | 300 |
| tatactgggt taactttggg aaatgcaagt gtttatctcc aggatctagc caccggggtg | 360 |
| gtgtaagccg caaagaagtt ccaccaggtg agaagagtga tgaccatcct tttccttact | 420 |
| atggttattt catactttgg ttgcatgaag gctgccccca tgaaagaagc aaacatccga | 480 |
| ggacaaggtg gcttggccta cccaggtgtg cggacccatg ggactctgga gagcgtgaat | 540 |
| gggcccaagg caggttcaag aggcttgaca tcattggctg acactttcga acacgtgata | 600 |
| gaagagctgt tggatgagga ccagaaagtt cggcccaatg aagaaaacaa taaggacgca | 660 |
| gacttgtaca cgtccagggt gatgctcagt agtcaagtgc ctttggagcc tcctcttctc | 720 |
| tttctgctgg aggaatacaa aaattaccta gatgctgcaa acatgtccat gagggtccgg | 780 |
| cgccactctg accctgcccg ccgaggggag ctgagcgtgt gtgacagtat tagtgagtgg | 840 |
| gtaacggcgg cagacaaaaa gactgcagtg gacatgtcgg gcgggacggt cacagtcctt | 900 |
| gaaaaggtcc ctgtatcaaa aggccaactg aagcaatact tctacgagac caagtgcaat | 960 |
| cccatgggtt acacaaaaga aggctgcagg ggcatagaca aaaggcattg gaactcccag | 1020 |
| tgccgaacta cccagtcgta cgtgcgggcc cttaccatgg atagcaaaaa gagaattggc | 1080 |
| tggcgattca taaggataga cacttcttgt gtatgtacat tgaccattaa aaggggaaga | 1140 |
| tagtggattt atgttgtata gattagatta tattgagaca aaaattatct atttgtatat | 1200 |
| atacataaca gggtaaatta ttcagttaag aaaaaaataa ttttatgaac tgcatgtata | 1260 |
| aatgaagttt atacagtaca gtggttctac aatctatttta ttggacatgt ccatgaccag | 1320 |
| aagggaaaca gtcatttgcg cacaacttaa aaagtctgca ttacattcct tgataatgtt | 1380 |
| gtggtttgtt gccgttgcca agaactgaaa acataaaaag ttaaaaaaaa taataaattg | 1440 |
| catgctgctt taattgtgaa ttgataataa actgtcctct ttcagaaaac agaaaaaaaa | 1500 |
| cacacacaca cacaacaaaa atttgaacca aaacattccg tttacatttt agacagtaag | 1560 |
| tatcttcgtt cttgttagta ctatatctgt tttactgctt ttaacttctg atagcgttgg | 1620 |
| aattaaaaca atgtcaaggt gctgttgtca ttgcttact ggcttagggg atggggdatg | 1680 |
| gggggtatat ttttgtttgt tttgtgtttt ttttcgtttt gtttgtttg tttttttagtt | 1740 |

```
cccacaggga gtagagatgg ggaaagaatt cctacaatat atattctggc tgataaaaga    1800
tacatttgta tgttgtgaag atgtttgcaa tatcgatcag atgactagaa agtgaataaa    1860
aattaaggca actgaacaaa aaaatgctca cactccacat cccgtgatgc acctcccagg    1920
ccccgctcat tctttgggcg ttggtcagag taagctgctt tgacggaag gacctatgtt    1980 tgctcagaac acattctttc cccccctccc cctctggtct cctctttgtt ttgttttaag    2040
gaagaaaaat cagttgcgcg ttctgaaata ttttaccact gctgtgaaca agtgaacaca    2100
ttgtgtcaca tcatgacact cgtataagca tggagaacag tgattttttt ttagaacaga    2160
aaacaacaaa aaataacccc aaaatgaaga ttatttttta tgaggagtga acatttgggt    2220
aaatcatggc taagcttaaa aaaaactcat ggtgaggctt aacaatgtct tgtaagcaaa    2280
aggtagagcc ctgtatcaac ccagaaacac ctagatcaga acaggaatcc acattgccag    2340
tgacatgaga ctgaacagcc aaatggaggc tatgtggagt tggcattgca tttaccggca    2400
gtgcgggagg aatttctgag tggccatccc aaggtctagg tggaggtggg gcatggtatt    2460
tgagacattc caaaacgaag gcctctgaag gacccttcag aggtggctct ggaatgacat    2520
gtgtcaagct gcttggacct cgtgctttaa gtgcctacat tatctaactg tgctcaagag    2580
gttctcgact ggaggaccac actcaagccg acttatgccc accatcccac ctctggataa    2640
ttttgcataa aattggatta gcctggagca ggttgggagc caaatgtggc atttgtgatc    2700
atgagattga tgcaatgaga tagaagatgt ttgctacctg aacacttatt gctttgaaac    2760
tagacttgag gaaccagggg tttatctttt gagaacttt ggtaagggaa aagggaacag    2820
gaaaagaaac cccaaactca ggccgaatga tcaaggggac ccataggaaa tcttgtccag    2880
agacaagact tcgggaaggt gtctggacat tcagaacacc aagacttgaa ggtgccttgc    2940
tcaatggaag aggccaggac agagctgaca aaattttgct ccccagtgaa ggccacagca    3000
accttctgcc catcctgtct gttcatggag agggtccctg cctcacctct gccatttttgg    3060 gttaggagaa gtcaagttgg gagcctgaaa tagtggttct tggaaaaatg gatccccagt    3120
gaaaactaga gctctaagcc cattcagccc atttcacacc tgaaaatgtt agtgatcacc    3180
acttggacca gcatccttaa gtatcagaaa gccccaagca attgctgcat cttagtaggg    3240
tgagggataa gcaaaagagg atgttcacca taacccagga atgaagatac catcagcaaa    3300
gaatttcaat ttgttcagtc tttcatttag agctagtctt tcacagtacc atctgaatac    3360
ctctttgaaa gaaggaagac tttacgtagt gtagatttgt tttgtgttgt tgaaaatat    3420 tatctttgta attattttta atatgtaagg aatgcttgga atatctgcta tatgtcaact    3480
ttatgcagct tcctttttgag ggacaaattt aaaacaaaca ccccccatc acaaacttaa    3540 aggattgcaa gggccagatc tgttaagtgg tttcatagga gacacatcca gcaattgtgt    3600
ggtcagtggc tcttttaccc aataagatac atcacagtca catgcttgat ggtttatgtt    3660
gacctaagat ttatttttgtt aaaatctctc tctgttgtgt tcgttcttgt tctgttttgt    3720
tttgtttttt aaagtcttgc tgtggtctct ttgtggcaga agtgtttcat gcatggcagc    3780
aggcctgttg ctttttttatg gcgattccca ttgaaaatgt aagtaaatgt ctgtggcctt    3840
gttctctcta tggtaaagat attattcacc atgtaaaaca aaaacaata tttattgtat    3900 tttagtatat ttatataatt atgttattga aaaaaattgg cattaaaact taaccgcatc    3960
agaacctatt gtaaatacaa gttctatttta agtgtactaa ttaacatata atatatgttt    4020
taaatataga atttttaatg tttttaaata tattttcaaa gtacataaaa aaaaaaaaaa    4080
aaaa                                                                  4084
```

<210> SEQ ID NO 26
<211> LENGTH: 4044
<212> TYPE: DNA
<213> ORGANISM: Homo sapiens

<400> SEQUENCE: 26

| | | | | | |
|---|---|---|---|---|---|
| ggcaatcatt | ggtaacctcg | ctcattcatt | agaatcacgt | aagaactcaa | aaggaaacgt | 60 |
| gtctctcgga | gtgagggcgt | ttgcgtaaat | ctataggttt | ttcgacatcg | atgccagttg | 120 |
| ctttgtcttc | tgtagtcgcc | aaggtggttg | agagtttaag | cttgcggata | ttgcaaaggg | 180 |
| ttattagatt | cataagtcac | accaagtggt | gggcgatcca | ctgagcaaag | ccgaacttct | 240 |
| cacatgatga | cttcaaacaa | gacacattac | cttccagcat | ctgttgggga | gacgagattt | 300 |
| taagacactt | gagtctccag | gacagcaaag | gcacaatgtt | ccaccaggtg | agaagagtga | 360 |
| tgaccatcct | tttccttact | atggttattt | catactttgg | ttgcatgaag | gctgccccca | 420 |
| tgaaagaagc | aaacatccga | ggacaaggtg | gcttggccta | cccaggtgtg | cggacccatg | 480 |
| ggactctgga | gagcgtgaat | gggcccaagg | caggttcaag | aggcttgaca | tcattggctg | 540 |
| acactttcga | cacgtgata | aagagctgt | tggatgagga | ccagaaagtt | cggcccaatg | 600 |
| aagaaaacaa | taaggacgca | gacttgtaca | cgtccaggt | gatgctcagt | agtcaagtgc | 660 |
| ctttggagcc | tcctcttctc | tttctgctgg | aggaatacaa | aaattaccta | gatgctgcaa | 720 |
| acatgtccat | gagggtccgg | cgccactctg | accctgcccg | ccgaggggag | ctgagcgtgt | 780 |
| gtgacagtat | tagtgagtgg | gtaacggcgg | cagacaaaaa | gactgcagtg | gacatgtcgg | 840 |
| gcgggacggt | cacagtcctt | gaaaaggtcc | ctgtatcaaa | aggccaactg | aagcaatact | 900 |
| tctacgagac | caagtgcaat | cccatgggtt | acacaaaaga | aggctgcagg | ggcatagaca | 960 |
| aaaggcattg | gaactcccag | tgccgaacta | cccagtcgta | cgtgcgggcc | cttaccatgg | 1020 |
| atagcaaaaa | gagaattggc | tggcgattca | taaggataga | cacttcttgt | gtatgtacat | 1080 |
| tgaccattaa | aaggggaaga | tagtggattt | atgttgtata | gattagatta | tattgagaca | 1140 |
| aaaattatct | atttgtatat | atacataaca | gggtaaatta | ttcagttaag | aaaaaaataa | 1200 |
| ttttatgaac | tgcatgtata | aatgaagttt | atacagtaca | gtggttctac | aatctatta | 1260 |
| ttggacatgt | ccatgaccag | aagggaaaca | gtcatttgcg | cacaacttaa | aaagtctgca | 1320 |
| ttacattcct | tgataatgtt | gtggtttgtt | gccgttgcca | agaactgaaa | acataaaaag | 1380 |
| ttaaaaaaaa | taataaattg | catgctgctt | taattgtgaa | ttgataataa | actgtcctct | 1440 |
| tcagaaaac | agaaaaaaaa | cacacacaca | cacaacaaaa | atttgaacca | aaacattccg | 1500 |
| tttacattt | agacagtaag | tatcttcgtt | cttgttagta | ctatatctgt | tttactgctt | 1560 |
| ttaacttctg | atagcgttgg | aattaaaaca | atgtcaaggt | gctgttgtca | ttgctttact | 1620 |
| ggcttagggg | atgggggatg | gggggtatat | ttttgtttgt | tttgtgtttt | ttttcgttt | 1680 |
| gtttgttttg | ttttttagtt | cccacaggga | gtagagatgg | ggaaagaatt | cctacaatat | 1740 |
| atattctggc | tgataaaaga | tacatttgta | tgttgtgaag | atgtttgcaa | tatcgatcag | 1800 |
| atgactagaa | agtgaataaa | aattaaggca | actgaacaaa | aaaatgctca | cactccacat | 1860 |
| cccgtgatgc | acctcccagg | ccccgctcat | tctttgggcg | ttggtcagag | taagctgctt | 1920 |
| ttgacggaag | gacctatgtt | tgctcagaac | acattctttc | ccccctccc | cctctggtct | 1980 |
| cctcttgtt | ttgtttaag | gaagaaaaat | cagttgcgcg | ttctgaaata | ttttaccact | 2040 |
| gctgtgaaca | agtgaacaca | ttgtgtcaca | tcatgacact | cgtataagca | tggagaacag | 2100 |
| tgatttttt | ttagaacaga | aacaacaaa | aataaccc | aaaatgaaga | ttatttttta | 2160 |

| | | | | | |
|---|---|---|---|---|---|
| tgaggagtga | acatttgggt | aaatcatggc | taagcttaaa | aaaaactcat | ggtgaggctt | 2220 |
| aacaatgtct | tgtaagcaaa | aggtagagcc | ctgtatcaac | ccagaaacac | ctagatcaga | 2280 |
| acaggaatcc | acattgccag | tgacatgaga | ctgaacagcc | aaatggaggc | tatgtggagt | 2340 |
| tggcattgca | tttaccggca | gtgcgggagg | aatttctgag | tggccatccc | aaggtctagg | 2400 |
| tggaggtggg | gcatggtatt | tgagacattc | caaaacgaag | gcctctgaag | gaccccttcag | 2460 |
| aggtggctct | ggaatgacat | gtgtcaagct | gcttggacct | cgtgctttaa | gtgcctacat | 2520 |
| tatctaactg | tgctcaagag | gttctcgact | ggaggaccac | actcaagccg | acttatgccc | 2580 |
| accatcccac | ctctggataa | ttttgcataa | aattggatta | gcctggagca | ggttgggagc | 2640 |
| caaatgtggc | atttgtgatc | atgagattga | tgcaatgaga | tagaagatgt | tgctacctg | 2700 |
| aacacttatt | gctttgaaac | tagacttgag | gaaaccaggg | tttatctttt | gagaactttt | 2760 |
| ggtaagggaa | aagggaacag | gaaaagaaac | cccaaactca | ggccgaatga | tcaaggggac | 2820 |
| ccataggaaa | tcttgtccag | agacaagact | tcgggaaggt | gtctggacat | tcagaacacc | 2880 |
| aagacttgaa | ggtgccttgc | tcaatggaag | aggccaggac | agagctgaca | aaattttgct | 2940 |
| ccccagtgaa | ggccacagca | accttctgcc | catcctgtct | gttcatggag | agggtccctg | 3000 |
| cctcacctct | gccatttttgg | gttaggagaa | gtcaagttgg | gagcctgaaa | tagtggttct | 3060 |
| tggaaaaatg | gatccccagt | gaaaactaga | gctctaagcc | cattcagccc | atttcacacc | 3120 |
| tgaaaatgtt | agtgatcacc | acttggacca | gcatccttaa | gtatcagaaa | gccccaagca | 3180 |
| attgctgcat | cttagtaggg | tgagggataa | gcaaagagg | atgttcacca | taacccagga | 3240 |
| atgaagatac | catcagcaaa | gaatttcaat | ttgttcagtc | tttcatttag | agctagtctt | 3300 |
| tcacagtacc | atctgaatac | ctcttttgaaa | gaaggaagac | tttacgtagt | gtagatttgt | 3360 |
| tttgtgttgt | ttgaaaatat | tatctttgta | attattttta | atatgtaagg | aatgcttgga | 3420 |
| atatctgcta | tatgtcaact | ttatgcagct | tcctttttgag | ggacaaattt | aaaacaaaca | 3480 |
| acccccatc | acaaacttaa | aggattgcaa | gggccagatc | tgttaagtgg | tttcatagga | 3540 |
| gacacatcca | gcaattgtgt | ggtcagtggc | tcttttaccc | aataagatac | atcacagtca | 3600 |
| catgcttgat | ggtttatgtt | gacctaagat | ttattttgtt | aaaatctctc | tctgttgtgt | 3660 |
| tcgttcttgt | tctgttttgt | tttgtttttt | aaagtcttgc | tgtggtctct | ttgtggcaga | 3720 |
| agtgtttcat | gcatggcagc | aggcctgttg | cttttttatg | gcgattccca | ttgaaaatgt | 3780 |
| aagtaaatgt | ctgtggcctt | gttctctcta | tggtaaagat | attattcacc | atgtaaaaca | 3840 |
| aaaaacaata | tttattgtat | tttagtatat | ttatataatt | atgttattga | aaaaaattgg | 3900 |
| cattaaaact | taaccgcatc | agaacctatt | gtaaatacaa | gttctatta | agtgtactaa | 3960 |
| ttaacatata | atatatgttt | taaatataga | atttttaatg | ttttttaaata | tattttcaaa | 4020 |
| gtacataaaa | aaaaaaaaaa | aaaa | | | | 4044 |

```
<210> SEQ ID NO 27
<211> LENGTH: 3972
<212> TYPE: DNA
<213> ORGANISM: Homo sapiens

<400> SEQUENCE: 27
```

| | | | | | |
|---|---|---|---|---|---|
| gctgccgccg | ccgcgcccgg | gcgcacccgc | ccgctcgctg | tcccgcgcac | cccgtagcgc | 60 |
| ctcgggctcc | cgggccggac | agaggagcca | gcccggtgcg | ccctccacc | tcctgctcgg | 120 |
| ggggctttaa | tgagacaccc | accgctgctg | tggggccggc | ggggagcagc | accgcgacgg | 180 |
| ggaccggggc | tgggcgctgg | agccagaatc | ggaaccacga | tgtgactccg | ccgccgggga | 240 |

```
cccgtgaggt tgtgtggac cccgagttcc accaggtgag aagagtgatg accatccttt      300
tccttactat ggttatttca tactttggtt gcatgaaggc tgcccccatg aaagaagcaa      360
acatccgagg acaaggtggc ttggcctacc caggtgtgcg gacccatggg actctggaga      420
gcgtgaatgg gcccaaggca ggttcaagag gcttgacatc attggctgac actttcgaac      480
acgtgataga agagctgttg gatgaggacc agaaagttcg gcccaatgaa gaaaacaata      540
aggacgcaga cttgtacacg tccagggtga tgctcagtag tcaagtgcct ttggagcctc      600
ctcttctctt tctgctggag gaatacaaaa attacctaga tgctgcaaac atgtccatga      660
gggtccggcg ccactctgac cctgcccgcc gaggggagct gagcgtgtgt gacagtatta      720
gtgagtgggt aacggcggca gacaaaaaga ctgcagtgga catgtcgggc gggacggtca      780
cagtccttga aaaggtccct gtatcaaaag gccaactgaa gcaatacttc tacgagacca      840
agtgcaatcc catgggttac acaaaagaag gctgcagggg catagacaaa aggcattgga      900
actcccagtg ccgaactacc cagtcgtacg tgcgggccct taccatggat agcaaaaaga      960
gaattggctg gcgattcata aggatagaca cttcttgtgt atgtacattg accattaaaa     1020
ggggaagata tgtggattta tgttgtataga ttagattata ttgagacaaa aattatctat     1080
ttgtatatat acataacagg gtaaattatt cagttaagaa aaaataatt ttatgaactg      1140 catgtataaa tgaagtttat acagtacagt ggttctacaa tctatttatt ggacatgtcc     1200
atgaccagaa gggaaacagt catttgcgca caacttaaaa agtctgcatt acattccttg     1260
ataatgttgt ggtttgttgc cgttgccaag aactgaaaac ataaaagtt aaaaaaaata     1320 ataaattgca tgctgcttta attgtgaatt gataataaac tgtcctcttt cagaaaacag     1380
aaaaaaaaca cacacacaca caacaaaaat ttgaaccaaa acattccgtt tacatttttag     1440 acagtaagta tcttcgttct tgttagtact atatctgttt tactgctttt aacttctgat     1500
agcgttggaa ttaaaacaat gtcaaggtgc tgttgtcatt gctttactgg cttaggggat     1560
gggggatggg gggtatattt tgtttgttt tgtgtttttt tttcgtttgt ttgttttgtt     1620
ttttagttcc cacagggagt agagatgggg aaagaattcc tacaatatat attctggctg     1680
ataaaagata catttgtatg ttgtgaagat gtttgcaata tcgatcagat gactagaaag     1740
tgaataaaaa ttaaggcaac tgaacaaaaa aatgctcaca ctccacatcc cgtgatgcac     1800
ctcccaggcc ccgctcattc tttgggcgtt ggtcagagta agctgctttt gacggaagga     1860
cctatgtttg ctcagaacac attctttccc cccctccccc tctggtctcc tctttgttt     1920 gttttaagga agaaaaatca gttgcgcgtt ctgaaatatt ttaccactgc tgtgaacaag     1980
tgaacacatt gtgtcacatc atgacactcg tataagcatg gagaacagtg attttttttt     2040
agaacagaaa acaacaaaaa ataacccaa atgaagatt ttttttatg aggagtgaac     2100 atttgggtaa atcatggcta agcttaaaaa aaactcatgg tgaggcttaa caatgtcttg     2160
taagcaaaag gtagagcct gtatcaaccc agaaacacct agatcagaac aggaatccac     2220
attgccagtg acatgagact gaacagccaa atggaggcta tgtggagttg gcattgcatt     2280
taccggcagt gcgggaggaa tttctgagtg gccatcccaa ggtctaggtg gaggtggggc     2340
atggtatttg agacattcca aaacgaaggc ctctgaagga cccttcagag gtggctctgg     2400
aatgacatgt gtcaagctgc ttggacctcg tgctttaagt gcctacatta tctaactgtg     2460
ctcaagaggt tctcgactgg aggaccacac tcaagccgac ttatgcccac catcccacct     2520
ctggataatt ttgcataaaa ttggattagc ctggagcagg ttgggagcca aatgtggcat     2580
ttgtgatcat gagattgatg caatgagata gaagatgttt gctacctgaa cacttattgc     2640
```

```
tttgaaacta gacttgagga aaccagggtt tatcttttga gaacttttgg taagggaaaa    2700
gggaacagga aaagaaaccc caaactcagg ccgaatgatc aaggggaccc ataggaaatc    2760
ttgtccagag acaagacttc gggaaggtgt ctggacattc agaacaccaa gacttgaagg    2820
tgccttgctc aatggaagag gccaggacag agctgacaaa attttgctcc ccagtgaagg    2880
ccacagcaac cttctgccca tcctgtctgt tcatggagag ggtccctgcc tcacctctgc    2940
cattttgggt taggagaagt caagttggga gcctgaaata gtggttcttg gaaaaatgga    3000
tccccagtga aaactagagc tctaagccca ttcagcccat ttcacacctg aaaatgttag    3060
tgatcaccac ttggaccagc atccttaagt atcagaaagc cccaagcaat tgctgcatct    3120
tagtagggtg agggataagc aaaagaggat gttcaccata acccaggaat gaagatacca    3180
tcagcaaaga atttcaattt gttcagtctt tcatttagag ctagtctttc acagtaccat    3240
ctgaatacct ctttgaaaga aggaagactt tacgtagtgt agatttgttt tgtgttgttt    3300
gaaaatatta tctttgtaat tattttaat atgtaaggaa tgcttggaat atctgctata    3360
tgtcaacttt atgcagcttc cttttgaggg acaaatttaa aacaaacaac cccccatcac    3420
aaacttaaag gattgcaagg gccagatctg ttaagtggtt tcataggaga cacatccagc    3480
aattgtgtgg tcagtggctc ttttacccaa taagatacat cacagtcaca tgcttgatgg    3540
tttatgttga cctaagattt attttgttaa aatctctctc tgttgtgttc gttcttgttc    3600
tgttttgttt tgttttttaa agtcttgctg tggtctcttt gtggcagaag tgtttcatgc    3660
atggcagcag gcctgttgct ttttatggc gattcccatt gaaaatgtaa gtaaatgtct    3720
gtggccttgt tctctctatg gtaaagatat tattcaccat gtaaaacaaa aacaatatt    3780
tattgtattt tagtatattt atataattat gttattgaaa aaaattggca ttaaaactta    3840
accgcatcag aacctattgt aaatacaagt tctatttaag tgtactaatt aacatataat    3900
atatgtttta aatatagaat ttttaatgtt tttaaatata ttttcaaagt acataaaaaa    3960
aaaaaaaaaa aa    3972
```

<210> SEQ ID NO 28
<211> LENGTH: 4016
<212> TYPE: DNA
<213> ORGANISM: Homo sapiens

<400> SEQUENCE: 28

```
ggctgctctc gctgccgctc ccccccggcga actagcatga aatctccctg cctctgccga     60
gatcaaatgg agcttctcgc tgatggggtg cgagtattac ctccgccatg caatttccac    120
tatcaataat ttaacttctt tgctgcagaa cagaaggagt acataccggg caccaaagac    180
tcgcgccccc tccccctttt aattaagcga agggaacgtg aaaaaataat agagtgtggg    240
agttttgggg ccgaagtctt tcccggagca gctgccttga tggttacttt gacaagtagt    300
gactgaaaag ttccaccagg tgagaagagt gatgaccatc cttttcctta ctatggttat    360
ttcatacttt ggttgcatga aggctgcccc catgaaagaa gcaaacatcc gaggacaagg    420
tggcttggcc tacccaggtg tgcggaccca tgggactctg gagagcgtga atgggcccaa    480
ggcaggttca agaggcttga catcattggc tgacactttc gaacacgtga tagaagagct    540
gttggatgag gaccagaaag ttcggcccaa tgaagaaaac aataaggacg cagacttgta    600
cacgtccagg gtgatgctca gtagtcaagt gcctttggag cctcctcttc tctttctgct    660
ggaggaatac aaaaattacc tagatgctgc aaacatgtcc atgagggtcc ggcgccactc    720
tgaccctgcc cgccgagggg agctgagcgt gtgtgacagt attagtgagt gggtaacggc    780
```

```
ggcagacaaa aagactgcag tggacatgtc gggcgggacg gtcacagtcc ttgaaaaggt      840
ccctgtatca aaaggccaac tgaagcaata cttctacgag accaagtgca atcccatggg      900
ttacacaaaa gaaggctgca ggggcataga caaaaggcat tggaactccc agtgccgaac      960
tacccagtcg tacgtgcggg cccttaccat ggatagcaaa aagagaattg gctggcgatt     1020
cataaggata gacacttctt gtgtatgtac attgaccatt aaaaggggaa gatagtggat     1080
ttatgttgta tagattagat tatattgaga caaaaattat ctatttgtat atatacataa     1140
cagggtaaat tattcagtta agaaaaaaat aattttatga actgcatgta taaatgaagt     1200
ttatacagta cagtggttct acaatctatt tattggacat gtccatgacc agaagggaaa     1260
cagtcatttg cgcacaactt aaaaagtctg cattacattc cttgataatg ttgtggtttg     1320
ttgccgttgc caagaactga aaacataaaa agttaaaaaa aataataaat tgcatgctgc     1380
tttaattgtg aattgataat aaactgtcct ctttcagaaa acagaaaaaa aacacacaca     1440
cacacaacaa aaatttgaac caaaacattc cgtttacatt ttagacagta agtatcttcg     1500
ttcttgttag tactatatct gttttactgc ttttaacttc tgatagcgtt ggaattaaaa     1560
caatgtcaag gtgctgttgt cattgcttta ctggcttagg ggatggggga tgggggtat      1620 attttttgttt gttttgtgtt tttttttcgt ttgtttgttt tgtttttag ttcccacagg     1680 gagtagagat ggggaaagaa ttcctacaat atatattctg gctgataaaa gatacatttg     1740
tatgttgtga agatgtttgc aatatcgatc agatgactag aaagtgaata aaaattaagg     1800
caactgaaca aaaaaatgct cacactccac atcccgtgat gcacctccca ggccccgctc     1860
attctttggg cgttggtcag agtaagctgc ttttgacgga aggacctatg tttgctcaga     1920
acacattctt tccccccctc ccctctggt ctcctctttg ttttgttta aggaagaaaa      1980 atcagttgcg cgttctgaaa tattttacca ctgctgtgaa caagtgaaca cattgtgtca     2040
catcatgaca ctcgtataag catggagaac agtgatttt ttttagaaca gaaaacaaca      2100
aaaaataacc ccaaaatgaa gattatttt tatgaggagt gaacatttgg gtaaatcatg      2160
gctaagctta aaaaaaactc atggtgaggc ttaacaatgt cttgtaagca aaaggtagag     2220
ccctgtatca acccagaaac acctagatca gaacaggaat ccacattgcc agtgacatga     2280
gactgaacag ccaaatggag gctatgtgga gttggcattg catttaccgg cagtgcggga     2340
ggaatttctg agtggccatc ccaaggtcta ggtggaggtg gggcatggta tttgagacat     2400
tccaaaacga aggcctctga aggacccttc agaggtggct ctggaatgac atgtgtcaag     2460
ctgcttggac ctcgtgcttt aagtgcctac attatctaac tgtgctcaag aggttctcga     2520
ctggaggacc acactcaagc cgacttatgc ccaccatccc acctctggat aattttgcat     2580
aaaattggat tagcctggag caggttggga gccaaatgtg gcatttgtga tcatgagatt     2640
gatgcaatga gatagaagat gtttgctacc tgaacactta ttgctttgaa actagacttg     2700
aggaaaccag ggtttatctt ttgagaactt ttggtaaggg aaaagggaac aggaaaagaa     2760
accccaaact caggccgaat gatcaagggg acccatagga aatcttgtcc agagacaaga     2820
cttcgggaag gtgtctggac attcagaaca ccaagacttg aaggtgcctt gctcaatgga     2880
agaggccagg acagagctga caaaattttg ctccccagtg aaggccacag caaccttctg     2940
cccatcctgt ctgttcatgg agagggtccc tgcctcacct ctgccatttt gggttaggag     3000
aagtcaagtt gggagcctga atagtggtt cttggaaaaa tggatcccca gtgaaaacta      3060
gagctctaag cccattcagc ccatttcaca cctgaaaatg ttagtgatca ccacttggac     3120
cagcatcctt aagtatcaga aagccccaag caattgctgc atcttagtag ggtgagggat     3180
```

| | | | | |
|---|---|---|---|---|
| aagcaaaaga | ggatgttcac | cataacccag | gaatgaagat | accatcagca | aagaatttca | 3240 |
| atttgttcag | tctttcattt | agagctagtc | tttcacagta | ccatctgaat | acctctttga | 3300 |
| aagaaggaag | actttacgta | gtgtagattt | gttttgtgtt | gtttgaaaat | attatctttg | 3360 |
| taattatttt | taatatgtaa | ggaatgcttg | gaatatctgc | tatatgtcaa | ctttatgcag | 3420 |
| cttccttttg | agggacaaat | ttaaaacaaa | caaccccca | tcacaaactt | aaaggattgc | 3480 |
| aagggccaga | tctgttaagt | ggtttcatag | agacacatc | cagcaattgt | gtggtcagtg | 3540 |
| gctcttttac | ccaataagat | acatcacagt | cacatgcttg | atggtttatg | ttgacctaag | 3600 |
| atttattttg | ttaaaatctc | tctctgttgt | gttcgttctt | gttctgtttt | gttttgtttt | 3660 |
| ttaaagtctt | gctgtggtct | ctttgtggca | gaagtgtttc | atgcatggca | gcaggcctgt | 3720 |
| tgcttttta | tggcgattcc | cattgaaaat | gtaagtaaat | gtctgtggcc | ttgttctctc | 3780 |
| tatggtaaag | atattattca | ccatgtaaaa | caaaaacaa | tatttattgt | attttagtat | 3840 |
| atttatataa | ttatgttatt | gaaaaaaatt | ggcattaaaa | cttaaccgca | tcagaaccta | 3900 |
| ttgtaaatac | aagttctatt | taagtgtact | aattaacata | taatatatgt | tttaaatata | 3960 |
| gaattttaa | tgttttaaa | tatattttca | aagtacataa | aaaaaaaaa | aaaaaa | 4016 |

<210> SEQ ID NO 29
<211> LENGTH: 3958
<212> TYPE: DNA
<213> ORGANISM: Homo sapiens

<400> SEQUENCE: 29

| | | | | |
|---|---|---|---|---|
| agtggactta | caagtccgaa | gccaatgtag | cttggaaaac | ttgggaggcg | gaattcctac | 60 |
| cgctgggaac | tgaaagggtc | tgcgacactc | tcgggcaggc | cgaacccaca | tctctaccca | 120 |
| tcctgcgccc | ctcttctgaa | gcgccctcca | gggaagttaa | gagttttgac | tttcggggag | 180 |
| tggttgggat | gtacgtgggg | gattcttgac | tcgggttagt | ctctggggat | gcagagccgg | 240 |
| gaagaggaat | ggttccacca | ggtgagaaga | gtgatgacca | tcctttttcct | tactatggtt | 300 |
| atttcatact | ttggttgcat | gaaggctgcc | cccatgaaag | aagcaaacat | ccgaggacaa | 360 |
| ggtggcttgg | cctacccagg | tgtgcggacc | catgggactc | tggagagcgt | gaatgggccc | 420 |
| aaggcaggtt | caagaggctt | gacatcattg | gctgacactt | tcgaacacgt | gatagaagag | 480 |
| ctgttggatg | aggaccagaa | agttcggccc | aatgaagaaa | acaataagga | cgcagacttg | 540 |
| tacacgtcca | gggtgatgct | cagtagtcaa | gtgcctttgg | agcctcctct | tctctttctg | 600 |
| ctggaggaat | acaaaaatta | cctagatgct | gcaaacatgt | ccatgagggt | ccggcgccac | 660 |
| tctgaccctg | cccgccgagg | ggagctgagc | gtgtgtgaca | gtattagtga | gtgggtaacg | 720 |
| gcggcagaca | aaaagactgc | agtggacatg | tcgggcggga | cggtcacagt | ccttgaaaag | 780 |
| gtccctgtat | caaaaggcca | actgaagcaa | tacttctacg | agaccaagtg | caatcccatg | 840 |
| ggttacacaa | agaaggctg | caggggcata | gacaaaaggc | attggaactc | ccagtgccga | 900 |
| actacccagt | cgtacgtgcg | ggcccttacc | atggatagca | aaagagaat | tggctggcga | 960 |
| ttcataagga | tagacacttc | ttgtgtatgt | acattgacca | ttaaaagggg | aagatagtgg | 1020 |
| atttatgttg | tatagattag | attatattga | gacaaaaatt | atctatttgt | atatatacat | 1080 |
| aacagggtaa | attattcagt | taagaaaaaa | ataattttat | gaactgcatg | tataaatgaa | 1140 |
| gtttatacag | tacagtggtt | ctacaatcta | tttattggac | atgtccatga | ccagaaggga | 1200 |
| aacagtcatt | tgcgcacaac | ttaaaaagtc | tgcattacat | tccttgataa | tgttgtggtt | 1260 |
| tgttgccgtt | gccaagaact | gaaaacataa | aaagttaaaa | aaataataa | attgcatgct | 1320 |

```
gctttaattg tgaattgata ataaactgtc ctctttcaga aaacagaaaa aaaacacaca    1380
cacacacaac aaaaatttga accaaaacat tccgtttaca ttttagacag taagtatctt    1440
cgttcttgtt agtactatat ctgttttact gcttttaact tctgatagcg ttggaattaa    1500
aacaatgtca aggtgctgtt gtcattgctt tactggctta ggggatgggg gatgggggt    1560 atattttgt ttgttttgtg ttttttttc gtttgtttgt tttgtttttt agttcccaca    1620
gggagtagag atggggaaag aattcctaca atatatattc tggctgataa agatacatt    1680 tgtatgttgt gaagatgttt gcaatatcga tcagatgact agaaagtgaa taaaaattaa    1740
ggcaactgaa caaaaaaatg ctcacactcc acatcccgtg atgcacctcc caggccccgc    1800
tcattctttg ggcgttggtc agagtaagct gcttttgacg gaaggaccta tgtttgctca    1860
gaacacattc tttccccccc tcccctctg tctcctctt tgttttgttt taaggaagaa    1920
aaatcagttg cgcgttctga aatattttac cactgctgtg aacaagtgaa cacattgtgt    1980
cacatcatga cactcgtata agcatggaga acagtgattt tttttagaa cagaaaacaa    2040 caaaaataa ccccaaaatg aagattattt tttatgagga gtgaacattt gggtaaatca    2100
tggctaagct taaaaaaaac tcatggtgag gcttaacaat gtcttgtaag caaaaggtag    2160
agccctgtat caacccagaa acacctagat cagaacagga atccacattg ccagtgacat    2220
gagactgaac agccaaatgg aggctatgtg gagttggcat tgcatttacc ggcagtgcgg    2280
gaggaatttc tgagtggcca tcccaaggtc taggtggagg tggggcatgg tatttgagac    2340
attccaaaac gaaggcctct gaaggaccct tcagaggtgg ctctggaatg acatgtgtca    2400
agctgcttgg acctcgtgct ttaagtgcct acattatcta actgtgctca agaggttctc    2460
gactggagga ccacactcaa gccgacttat gcccaccatc ccacctctgg ataattttgc    2520
ataaaattgg attagcctgg agcaggttgg gagccaaatg tggcatttgt gatcatgaga    2580
ttgatgcaat gagatagaag atgtttgcta cctgaacact tattgctttg aaactagact    2640
tgaggaaacc agggtttatc ttttgagaac ttttggtaag ggaaaaggga acaggaaaag    2700
aaaccccaaa ctcaggccga atgatcaagg ggacccatag gaaatcttgt ccagagacaa    2760
gacttcggga aggtgtctgg acattcagaa caccaagact tgaaggtgcc ttgctcaatg    2820
gaagaggcca ggacagagct gacaaaattt tgctccccag tgaaggccac agcaaccttc    2880
tgcccatcct gtctgttcat ggagagggtc cctgcctcac ctctgccatt tgggttaggg    2940
agaagtcaag ttgggagcct gaaatagtgg ttcttggaaa aatggatccc cagtgaaaac    3000
tagagctcta agcccattca gcccatttca cacctgaaaa tgttagtgat caccacttgg    3060
accagcatcc ttaagtatca gaaagcccca agcaattgct gcatcttagt agggtgaggg    3120
ataagcaaaa gaggatgttc accataaccc aggaatgaag ataccatcag caagaatttt    3180
caatttgttc agtctttcat ttagagctag tctttcacag taccatctga atacctcttt    3240
gaaagaagga agactttacg tagtgtagat ttgttttgtg ttgtttgaaa atattatctt    3300
tgtaattatt tttaatatgt aaggaatgct tggaatatct gctatatgtc aactttatgc    3360
agcttccttt tgagggacaa atttaaaaca aacaaccccc catcacaaac ttaaaggatt    3420
gcaagggcca gatctgttaa gtggtttcat aggagacaca tccagcaatt gtgtggtcag    3480
tggctctttt acccaataag atacatcaca gtcacatgct tgatggttta tgttgaccta    3540
agatttattt tgttaaaatc tctctctgtt gtgttcgttc ttgttctgtt ttgttttgtt    3600
ttttaaagtc ttgctgtggt ctcctttgtgg cagaagtgtt tcatgcatgg cagcaggcct    3660
gttgcttttt tatggcgatt cccattgaaa atgtaagtaa atgtctgtgg ccttgttctc    3720
```

-continued

| | |
|---|---|
| tctatggtaa agatattatt caccatgtaa aacaaaaaac aatatttatt gtattttagt | 3780 |
| atatttatat aattatgtta ttgaaaaaaa ttggcattaa aacttaaccg catcagaacc | 3840 |
| tattgtaaat acaagttcta tttaagtgta ctaattaaca tataatatat gttttaaata | 3900 |
| tagaatttt aatgttttta aatatatttt caaagtacat aaaaaaaaaa aaaaaaaa | 3958 |

<210> SEQ ID NO 30
<211> LENGTH: 836
<212> TYPE: DNA
<213> ORGANISM: Homo sapiens

<400> SEQUENCE: 30

| | |
|---|---|
| ccgcctccag cgcgcccttg ctgccccgcg cgaccccagg attgcgaact cttgcccctg | 60 |
| acctgttggg cggggctccg cgctccagcc atcagcccgg atgggtctcc tggctgggac | 120 |
| ttggggcacc tggagttaat gtccaaccta gggtctgcgg agacccgatc cgaggtgccg | 180 |
| ccgccggacg ggactttaag atgaagttat gggatgtcgt ggctgtctgc ctggtgctgc | 240 |
| tccacaccgc gtccgccttc ccgctgcccg ccggtaagag gcctcccgag gcgcccgccg | 300 |
| aagaccgctc cctcggccgc cgccgcgcgc ccttcgcgct gagcagtgac tcaaatatgc | 360 |
| cagaggatta tcctgatcag ttcgatgatg tcatggattt tattcaagcc accattaaaa | 420 |
| gactgaaaag gtcaccagat aaacaaatgg cagtgcttcc tagaagagag cggaatcggc | 480 |
| aggctgcagc tgccaaccca gagaattcca gaggaaaagg tcggagaggc cagaggggca | 540 |
| aaaaccgggg ttgtgtctta actgcaatac atttaaatgt cactgacttg ggtctgggct | 600 |
| atgaaaccaa ggaggaactg attttaggt actgcagcgg ctcttgcgat gcagctgaga | 660 |
| caacgtacga caaaatattg aaaaacttat ccagaaatag aaggctggtg agtgacaaag | 720 |
| tagggcaggc atgttgcaga cccatcgcct ttgatgatga cctgtcgttt ttagatgata | 780 |
| acctggttta ccatattcta agaaagcatt ccgctaaaag gtgtggatgt atctga | 836 |

<210> SEQ ID NO 31
<211> LENGTH: 681
<212> TYPE: DNA
<213> ORGANISM: Homo sapiens

<400> SEQUENCE: 31

| | |
|---|---|
| catacgggcc aaaagtctcc aagtccctgc taacttcttg ctctcgcaac agaataccta | 60 |
| tttaggtggg aagaatgagg tgtgggcggc aggctgggtg ccgccgccgg acgggacttt | 120 |
| aagatgaagt tatgggatgt cgtggctgtc tgcctggtgc tgctccacac cgcgtccgcc | 180 |
| ttcccgctgc ccgccgcaaa tatgccagag gattatcctg atcagttcga tgatgtcatg | 240 |
| gattttattc aagccaccat taaaagactg aaaaggtcac cagataaaca aatggcagtg | 300 |
| cttcctagaa gagagcggaa tcggcaggct gcagctgcca acccagagaa ttccagagga | 360 |
| aaaggtcgga gaggccagag gggcaaaaac cggggttgtg tcttaactgc aatacattta | 420 |
| aatgtcactg acttgggtct gggctatgaa accaaggagg aactgatttt taggtactgc | 480 |
| agcggctctt gcgatgcagc tgagacaacg tacgacaaaa tattgaaaaa cttatccaga | 540 |
| aatagaaggc tggtgagtga caaagtaggg caggcatgtt gcagacccat cgcctttgat | 600 |
| gatgacctgt cgtttttaga tgataacctg gttaccata ttctaagaaa gcattccgct | 660 |
| aaaaggtgtg gatgtatctg a | 681 |

<210> SEQ ID NO 32
<211> LENGTH: 410
<212> TYPE: DNA

<213> ORGANISM: Homo sapiens

<400> SEQUENCE: 32

| | |
|---|---|
| atgaagttat gggatgtcgt ggctgtctgc ctggtgctgc tccacaccgc gtccgccttc | 60 |
| ccgctgccaa cccagagaat tccagaggaa aaggtcggag aggccagagg gcaaaaacc | 120 |
| ggggttgtgt cttaactgca atacatttaa atgtcactga cttgggtctg gctatgaaa | 180 |
| ccaaggagga actgattttt aggtactgca gcggctcttg cgatgcagct gagacaacgt | 240 |
| acgacaaaat attgaaaaac ttatccagaa atagaaggct ggtgagtgac aaagtagggc | 300 |
| aggcatgttg cagacccatc gcctttgatg atgacctgtc gttttagat gataacctgg | 360 |
| tttaccatat tctaagaaag cattccgcta aaaggtgtgg atgtatctga | 410 |

<210> SEQ ID NO 33
<211> LENGTH: 1052
<212> TYPE: DNA
<213> ORGANISM: Homo sapiens

<400> SEQUENCE: 33

| | |
|---|---|
| agagagcgct gggagccgga ggggagcgca gcgagttttg ccagtggtc gtgcagtcca | 60 |
| aggggctgga tggcatgctg gacccaagct cagctcagcg tccggaccca ataacagttt | 120 |
| taccaaggga gcagctttct atcctggcca cactgaggtg catagcgtaa tgtccatgtt | 180 |
| gttctacact ctgatcacag cttttctgat cggcatacag gcggaaccac actcagagag | 240 |
| caatgtccct gcaggacaca ccatccccca agcccactgg actaaacttc agcattccct | 300 |
| tgacactgcc cttcgcagag cccgcagcgc cccggcagcg gcgatagctg cacgcgtggc | 360 |
| ggggcagacc cgcaacatta ctgtggaccc caggctgttt aaaaagcggc gactccgttc | 420 |
| accccgtgtg ctgtttagca cccagcctcc ccgtgaagct gcagacactc aggatctgga | 480 |
| cttcgaggtc ggtggtgctg ccccccttcaa caggactcac aggagcaagc ggtcatcatc | 540 |
| ccatcccatc ttccacaggg gcgaattctc ggtgtgtgac agtgtcagcg tgtgggttgg | 600 |
| ggataagacc accgccacag acatcaaggg caaggaggtg atggtgttgg gagaggtgaa | 660 |
| cattaacaac agtgtattca aacagtactt ttttgagacc aagtgccggg acccaaatcc | 720 |
| cgttgacagc gggtgccggg gcattgactc aaagcactgg aactcatatt gtaccacgac | 780 |
| tcacaccttt gtcaaggcgc tgaccatgga tggcaagcag gctgcctggc ggtttatccg | 840 |
| gatagatacg gcctgtgtgt gtgtgctcag caggaaggct gtgagaagag cctgacctgc | 900 |
| cgacacgctc cctcccccctg cccttctac actctcctgg gccctccct acctcaacct | 960 |
| gtaaattatt ttaaattata aggactgcat ggtaatttat agtttataca gttttaaaga | 1020 |
| atcattattt attaaatttt tggaagcata aa | 1052 |

<210> SEQ ID NO 34
<211> LENGTH: 7260
<212> TYPE: DNA
<213> ORGANISM: Homo sapiens

<400> SEQUENCE: 34

| | |
|---|---|
| tcactgtcac tgctaaattc agagcagatt agagcctgcg caatggaata aagtcctcaa | 60 |
| aattgaaatg tgacattgct ctcaacatct cccatctctc tggatttcct tttgcttcat | 120 |
| tattcctgct aaccaattca ttttcagact ttgtacttca gaagcaatgg gaaaaatcag | 180 |
| cagtcttcca acccaattat ttaagtgctg cttttgtgat ttcttgaagg tgaagatgca | 240 |
| caccatgtcc tcctcgcatc tcttctacct ggcgctgtgc ctgctcacct tcaccagctc | 300 |

```
tgccacggct ggaccggaga cgctctgcgg ggctgagctg gtggatgctc ttcagttcgt      360
gtgtggagac aggggctttt atttcaacaa gcccacaggg tatggctcca gcagtcggag      420
ggcgcctcag acaggcatcg tggatgagtg ctgcttccgg agctgtgatc taaggaggct      480
ggagatgtat tgcgcacccc tcaagcctgc caagtcagct cgctctgtcc gtgcccagcg      540
ccacaccgac atgcccaaga cccagaagga agtacatttg aagaacgcaa gtagagggag      600
tgcaggaaac aagaactaca ggatgtagga agaccctcct gaggagtgaa gagtgacatg      660
ccaccgcagg atcctttgct ctgcacgagt tacctgttaa actttggaac acctaccaaa      720
aaataagttt gataacattt aaaagatggg cgtttccccc aatgaaatac acaagtaaac      780
attccaacat tgtctttagg agtgatttgc accttgcaaa aatggtcctg gagttggtag      840
attgctgttg atcttttatc aataatgttc tatagaaaag aaaaaaaaat atatatatat      900
atatatctta gtccctgcct ctcaagagcc acaaatgcat gggtgttgta tagatccagt      960
tgcactaaat tcctctctga atcttggctg ctggagccat tcattcagca accttgtcta     1020
agtggtttat gaattgtttc cttatttgca cttctttcta cacaactcgg gctgtttgtt     1080
ttacagtgtc tgataatctt gttagtctat acccaccacc tcccttcata accttttatat    1140 ttgccgaatt tggcctcctc aaaagcagca gcaagtcgtc aagaagcaca ccaattctaa     1200
cccacaagat tccatctgtg gcatttgtac caaatataag ttggatgcat tttattttag     1260
acacaaagct ttattttttcc acatcatgct tacaaaaaag aataatgcaa atagttgcaa     1320 cttttgaggcc aatcattttt aggcatatgt tttaaacata gaaagtttct tcaactcaaa    1380
agagttcctt caaatgatga gttaatgtgc aacctaatta gtaactttcc tcttttttatt   1440 ttttccatat agagcactat gtaaatttag catatcaatt atacaggata tatcaaacag     1500
tatgtaaaac tctgtttttt agtataatgg tgctattttg tagtttgtta tatgaaagag     1560
tctggccaaa acgtaatac gtgaaagcaa acaataggg gaagcctgga gccaaagatg       1620
acacaagggg aagggtactg aaaacaccat ccatttggga aagaaggcaa agtccccca     1680 gttatgcctt ccaagaggaa cttcagacac aaaagtccac tgatgcaaat tggactggcg     1740
agtccagaga ggaaactgtg gaatggaaaa agcagaaggc taggaatttt agcagtcctg     1800 gtttctttttt ctcatggaag aaatgaacat ctgccagctg tgtcatggac tcaccactgt   1860
gtgaccttgg gcaagtcact tcacctctct gtgcctcagt ttcctcatct gcaaaatggg    1920
ggcaatatgt catctaccta cctcaaaggg gtggtataag gtttaaaaag ataaagattc     1980 agatttttttt accctgggtt gctgtaaggg tgcaacatca gggcgcttga gttgctgaga   2040
tgcaaggaat tctataaata acccattcat agcatagcta gagattggtg aattgaatgc     2100
tcctgacatc tcagttcttg tcagtgaagc tatccaaata actggccaac tagttgttaa     2160
aagctaacag ctcaatctct taaaacactt ttcaaaatat gtgggaagca tttgattttc     2220
aatttgattt tgaattctgc atttggtttt atgaatacaa agataagtga aaagagagaa     2280
aggaaaagaa aaaggagaaa aacaaagaga tttctaccag tgaaggggga attaattact    2340
ctttgttagc actcactgac tcttctatgc agttactaca tatctagtaa aaccttgttt     2400
aatactataa ataatattct attcattttg aaaaacacaa tgattccttc ttttctaggc     2460
aatataagga aagtgatcca aaatttgaaa tattaaaata atatctaata aaaagtcaca    2520
aagttatctt cttttaacaaa ctttactctt attcttagct gtatatacat ttttttaaaa   2580
agtttgttaa aatatgcttg actagagttt cagttgaaag gcaaaaactt ccatcacaac     2640
aagaaatttc ccatgcctgc tcagaagggt agcccctagc tctctgtgaa tgtgttttat    2700
```

```
ccattcaact gaaaattggt atcaagaaag tccactggtt agtgtactag tccatcatag    2760
cctagaaaat gatccctatc tgcagatcaa gattttctca ttagaacaat gaattatcca    2820
gcattcagat ctttctagtc accttagaac ttttttggtta aaagtaccca ggcttgatta    2880
tttcatgcaa attctatatt ttacattctt ggaaagtcta tatgaaaaac aaaaataaca    2940
tcttcagttt ttctcccact gggtcacctc aaggatcaga ggccaggaaa aaaaaaaaag    3000
actccctgga tctctgaata tatgcaaaaa gaaggcccca tttagtggag ccagcaatcc    3060
tgttcagtca acaagtattt taactctcag tccaacatta tttgaattga gcacctcaag    3120
catgcttagc aatgttctaa tcactatgga cagatgtaaa agaaactata catcattttt    3180
gccctctgcc tgttttccag acatacaggt tctgtggaat aagatactgg actcctcttc    3240
ccaagatggc acttcttttt atttcttgtc cccagtgtgt acctttttaaa attattccct    3300 ctcaacaaaa ctttataggc agtcttctgc agacttaaca tgttttctgt catagttaga    3360
tgtgataatt ctaagagtgt ctatgactta tttccttcac ttaattctat ccacagtcaa    3420
aaatccccca aggaggaaag ctgaaagatg caactgccaa tattatcttt cttaactttt    3480
tccaacacat aatcctctcc aactggatta taaataaatt gaaataact cattataccca    3540 attcactatt ttatttttta atgaattaaa actagaaaac aaattgatgc aaaccctgga    3600
agtcagttga ttactatata ctacagcaga atgactcaga tttcatagaa aggagcaacc    3660
aaaatgtcac aaccaaaact ttacaagctt tgcttcagaa ttagattgct ttataattct    3720
tgaatgaggc aatttcaaga tatttgtaaa agaacagtaa acattggtaa gaatgagctt    3780
tcaactcata ggcttatttc caatttaatt gaccatactg gatacttagg tcaaatttct    3840
gttctctctt gcccaaataa tattaaagta ttatttgaac tttttaagat gaggcagttc    3900
ccctgaaaaa gttaatgcag ctctccatca gaatccactc ttctagggat atgaaaatct    3960
cttaacaccc accctacata cacagacaca cacacacaca cacacacaca cacacacaca    4020
cacacattca ccctaaggat ccaatggaat actgaaaaga aatcacttcc ttgaaaattt    4080
tattaaaaaa caaacaaaca aacaaaaagc ctgtccaccc ttgagaatcc ttcctctcct    4140
tggaacgtca atgtttgtgt agatgaaacc atctcatgct ctgtggctcc agggtttctg    4200
ttactatttt atgcacttgg gagaaggctt agaataaaag atgtagcaca ttttgctttc    4260
ccatttattg tttggccagc tatgccaatg tggtgctatt gtttctttaa gaaagtactt    4320
gactaaaaaa aaagaaaaa aagaaaaaaa agaaagcata gacatatttt tttaaagtat    4380
aaaaacaaca attctataga tagatggctt aataaaatag cattaggtct atctagccac    4440
caccaccttt caacttttta tcactcacaa gtagtgtact gttcaccaaa ttgtgaattt    4500
gggggtgcag gggcaggagt tggaaatttt taaagttag aaggctccat tgttttgttg    4560
gctctcaaac ttagcaaaat tagcaatata ttatccaatc ttctgaactt gatcaagagc    4620
atggagaata aacgcgggaa aaaagatctt ataggcaaat agaagaattt aaaagataag    4680
taagttcctt attgattttt gtgcactctg ctctaaaaca gatattcagc aagtggagaa    4740
aataagaaca aagagaaaaa atacatagat ttacctgcaa aaaatagctt ctgccaaatc    4800 cccttgggt attctttggc atttactggt ttatagaaga cattctccct tcacccagac    4860
atctcaaaga gcagtagctc tcatgaaaag caatcactga tctcatttgg gaaatgttgg    4920
aaagtatttc cttatgagat gggggttatc tactgataaa gaaagaattt atgagaaatt    4980
gttgaaagag atggctaaca atctgtgaag atttttttgtt tcttggtttt gttttttttt    5040
ttttttttac tttatacagt ctttatgaat ttcttaatgt tcaaaatgac ttggttcttt    5100
```

```
tcttcttttt tttatatcag aatgaggaat aataagttaa acccacatag actctttaaa    5160
actataggct agatagaaat gtatgtttga cttgttgaag ctataatcag actatttaaa    5220
atgttttgct attttaatc ttaaaagatt gtgctaattt attagagcag aacctgtttg    5280
gctctcctca gaagaaagaa tctttccatt caaatcacat ggctttccac caatattttc    5340
aaaagataaa tctgatttat gcaatggcat catttatttt aaaacagaag aattgtgaaa    5400
gtttatgccc ctcccttgca aagaccataa agtccagatc tggtaggggg gcaacaacaa    5460
aaggaaaatg ttgttgattc ttggttttgg attttgtttt gttttcaatg ctagtgttta    5520
atcctgtagt acatatttgc ttattgctat tttaatattt tataagacct tcctgttagg    5580
tattagaaag tgatacatag atatcttttt tgtgtaattt ctatttaaaa aagagagaag    5640
actgtcagaa gctttaagtg catatggtac aggataaaga tatcaattta ataaccaat    5700
tcctatctgg aacaatgctt tgtttttta aagaaacctc tcacagataa gacagaggcc    5760
caggggattt tgaagctgt ctttattctg cccccatccc aacccagccc ttattatttt    5820
agtatctgcc tcagaatttt atagagggct gaccaagctg aaactctaga attaaaggaa    5880
cctcactgaa aacatatatt tcacgtgttc cctctctttt ttttccttt tgtgagatgg    5940
ggtctcgcac tgtcccccag gctggagtgc agtggcatga tctcggctca ctgcaacctc    6000
cacctcctgg gtttaagcga ttctcctgcc tcagcctcct gagtagctgg gattacaggc    6060
acccaccact atgcccggct aatttttgg attttaata gagacggggt tttaccatgt    6120
tggccaggtt ggactcaaac tcctgacctt gtgatttgcc cgcctcagcc tcccaaattg    6180
ctgggattac aggcatgagc caccacaccc tgcccatgtg ttccctctta atgtatgatt    6240
acatggatct taaacatgat ccttctctcc tcattcttca actatctttg atggggtctt    6300
tcaagggaa aaaatccaa gcttttttaa agtaaaaaaa aaaaagaga ggacacaaaa    6360
ccaaatgtta ctgctcaact gaaatatgag ttaagatgga gacagagttt ctcctaataa    6420
ccggagctga attaccttc actttcaaaa acatgacctt ccacaatcct tagaatctgc    6480
ctttttttat attactgagg cctaaaagta aacattactc atttttatttt gcccaaaatg    6540
cactgatgta aagtaggaaa aataaaaaca gagctctaaa atcccttca agccaccat    6600
tgacccact caccaactca tagcaaagtc acttctgtta atcccttaat ctgatttgt    6660
ttggatattt atcttgtacc cgctgctaaa cacactgcag gagggactct gaaacctcaa    6720
gctgtctact tacatctttt atctgtgtct gtgtatcatg aaaatgtcta ttcaaaatat    6780
caaacctt caaatatcac gcagcttata ttcagtttac ataaaggccc caaataccat    6840
gtcagatctt tttggtaaaa gagttaatga actatgagaa ttgggattac atcatgtatt    6900
ttgcctcatg tatttttatc acacttatag gccaagtgtg ataaataaac ttacagacac    6960
tgaattaatt tcccctgcta ctttgaaacc agaaaataat gactggccat tcgttacatc    7020
tgtcttagtt gaaaagcata tttttttatta aattaattct gattgtattt gaaattatta    7080
ttcaattcac ttatggcaga ggaatatcaa tcctaatgac ttctaaaaat gtaactaatt    7140
gaatcattat cttacattta ctgttaata agcatatttt gaaatgtat ggctagagtg    7200
tcataataaa atggtatatc tttctttagt aattacaaaa aaaaaaaaaa aaaaaaaaa    7260
```

```
<210> SEQ ID NO 35
<211> LENGTH: 3665
<212> TYPE: DNA
<213> ORGANISM: Homo sapiens

<400> SEQUENCE: 35
```

```
ggcttggggc agccgggtag ctcggaggtc gtggcgctgg gggctagcac cagcgctctg    60
tcggaggcg  cagcggttag gtggaccggt cagcggactc accggccagg gcgctcggtg   120
ctggaatttg atattcattg atccgggttt tatccctctt cttttttctt aaacattttt   180
ttttaaaact gtattgtttc tcgttttaat ttattttgc  ttgccattcc ccacttgaat   240
cgggccgacg gcttggggag attgctctac ttccccaaat cactgtggat tttggaaacc   300
agcagaaaga ggaaagaggt agcaagagct ccagagagaa gtcgaggaag agagagacgg   360
ggtcagagag agcgcgcggg cgtgcgagca gcgaaagcga caggggcaaa gtgagtgacc   420
tgcttttggg ggtgaccgcc ggagcgcggc gtgagccctc cccccttggga tcccgcagct   480
gaccagtcgc gctgacggac agacagacag acaccgcccc cagccccagc taccacctcc   540
tccccggccg gcggcggaca gtggacgcgg cggcgagccg cgggcagggg ccggagcccg   600
cgcccggagg cggggtggag ggggtcgggg ctcgcggcgt cgcactgaaa cttttcgtcc   660
aacttctggg ctgttctcgc ttcggaggag ccgtggtccg cgcggggaa  gccgagccga   720
gcggagccgc gagaagtgct agctcgggcc gggaggagcc gcagccggag gagggggagg   780
aggaagaaga gaaggaagag gagaggggc  cgcagtggcg actcggcgct cggaagccgg   840
gctcatggac gggtgaggcg gcggtgtgcg cagacagtgc tccagccgcg cgcgctcccc   900
aggccctggc ccgggcctcg ggccggggag gaagagtagc tcgccgaggc gccgaggaga   960
gcgggccgcc ccacagcccg agccggagag ggagcgcgag ccgcgccggc cccggtcggg  1020
cctccgaaac catgaacttt ctgctgtctt gggtgcattg gagccttgcc ttgctgctct  1080
acctccacca tgccaagtgg tcccaggctg cacccatggc agaaggagga gggcagaatc  1140
atcacgaagt ggtgaagttc atggatgtct atcagcgcag ctactgccat ccaatcgaga  1200
ccctggtgga catcttccag gagtaccctg atgagatcga gtacatcttc aagccatcct  1260
gtgtgcccct gatgcgatgc ggggctgct  gcaatgacga gggcctggag tgtgtgccca  1320
ctgaggagtc caacatcacc atgcagatta tgcggatcaa acctcaccaa ggccagcaca  1380
taggagagat gagcttccta cagcacaaca atgtgaatg  cagaccaaag aaagatagag  1440
caagacaaga aaaaaaatca gttcgaggaa agggaagggg gcaaaaacga aagcgcaaga  1500
aatcccggta taagtcctgg agcgtgtacg ttggtgcccg ctgctgtcta atgccctgga  1560
gcctccctgg cccccatccc tgtgggcctt gctcagagcg gagaaagcat ttgtttgtac  1620
aagatccgca gacgtgtaaa tgttcctgca aaaacacaga ctcgcgttgc aaggcgaggc  1680
agcttgagtt aaacgaacgt acttgcagat gtgacaagcc gaggcggtga gccgggcagg  1740
aggaaggagc ctccctcagg gtttcgggaa ccagatctct caccaggaaa gactgataca  1800
gaacgatcga tacagaaacc acgctgccgc caccacacca tcaccatcga cagaacagtc  1860
cttaatccag aaacctgaaa tgaaggaaga ggagactctg cgcagagcac tttgggtccg  1920
gagggcgaga ctccggcgga agcattcccg ggcgggtgac ccagcacggt ccctcttgga  1980
attggattcg ccatttttatt tttcttgctg ctaaatcacc gagcccggaa gattagagag  2040
ttttatttct gggattcctg tagacacacc cacccacata catacattta tatatatata  2100
tattatatat ataaaaaat  aaatatctct attttatata tataaaatat atatattctt  2160
tttttaaatt aacagtgcta atgttattgg tgtcttcact ggatgtattt gactgctgtg  2220
gacttgagtt gggaggggaa tgttcccact cagatcctga cagggaagag gaggagatga  2280
gagactctgg catgatcttt ttttttgtccc acttggtggg gccagggtcc tctcccctgc  2340
ccaggaatgt gcaaggccag ggcatggggg caaatatgac ccagttttgg gaacaccgac  2400
```

```
aaacccagcc ctggcgctga gcctctctac cccaggtcag acggacagaa agacagatca  2460
caggtacagg gatgaggaca ccggctctga ccaggagttt ggggagcttc aggacattgc  2520
tgtgctttgg ggattccctc acatgctgc acgcgcatct cgcccccagg ggcactgcct  2580
ggaagattca ggagcctggg cggccttcgc ttactctcac ctgcttctga gttgcccagg  2640
agaccactgg cagatgtccc ggcgaagaga agagacacat tgttggaaga agcagcccat  2700
gacagctccc cttcctggga ctcgcccctca tcctcttcct gctcccccttc ctggggtgca  2760
gcctaaaagg acctatgtcc tcacaccatt gaaaccacta gttctgtccc cccaggagac  2820
ctggttgtgt gtgtgtgagt ggttgacctt cctccatccc ctggtccttc ccttcccttc  2880
ccgaggcaca gagagacagg gcaggatcca cgtgcccatt gtggaggcag agaaaagaga  2940
aagtgtttta tatacggtac ttatttaata tcccttttta attagaaatt aaaacagtta  3000
atttaattaa agagtagggt ttttttcag tattcttggt taatatttaa tttcaactat  3060
ttatgagatg tatcttttgc tctctcttgc tctcttattt gtaccggttt ttgtatataa  3120
aattcatgtt tccaatctct ctctccctga tcggtgacag tcactagctt atcttgaaca  3180
gatatttaat tttgctaaca ctcagctctg ccctccccga tcccctggct ccccagcaca  3240
cattcctttg aaataaggtt tcaatataca tctacatact atatatatat ttggcaactt  3300
gtatttgtgt gtatatatat atatatatgt ttatgtatat atgtgattct gataaaatag  3360
acattgctat tctgtttttt atatgtaaaa acaaaacaag aaaaaataga gaattctaca  3420
tactaaatct ctctcctttt ttaattttaa tatttgttat catttatta ttggtgctac  3480
tgtttatccg taataattgt ggggaaaaga tattaacatc acgtctttgt ctctagtgca  3540
gttttttcgag atattccgta gtacatattt attttttaaac aacgacaaag aaatacagat  3600
atatcttaaa aaaaaaaaag catttttgtat taaagaattt aattctgatc tcaaaaaaaa  3660
aaaaa                                                              3665

<210> SEQ ID NO 36
<211> LENGTH: 3614
<212> TYPE: DNA
<213> ORGANISM: Homo sapiens

<400> SEQUENCE: 36
ggcttggggc agccgggtag ctcggaggtc gtggcgctgg gggctagcac cagcgctctg    60
tcgggaggcg cagcggttag gtggaccggt cagcggactc accggccagg gcgctcggtg   120
ctggaatttg atattcattg atccgggttt tatccctctt cttttttctt aaacatttttt   180
ttttaaaact gtattgtttc tcgttttaat ttatttttgc ttgccattcc ccacttgaat   240
cgggccgacg gcttggggag attgctctac ttccccaaat cactgtggat tttggaaacc   300
agcagaaaga ggaaagaggt agcaagagct ccagagagaa gtcgaggaag agagagacgg   360
ggtcagagag agcgcgcggg cgtgcgagca gcgaaagcga caggggcaaa gtgagtgacc   420
tgcttttggg ggtgaccgcc ggagcgcggc gtgagccctc cccttggga tcccgcagct    480
gaccagtcgc gctgacggac agacagacag acaccgcccc cagccccagc taccacctcc   540
tccccggccg gcggcggaca gtggacgcgg cggcgagccg cgggcagggg ccggagcccg   600
cgcccggagg cggggtggag ggggtcgggg ctcgcggcgt cgcactgaaa cttttcgtcc   660
aacttctggg ctgttctcgc ttcggaggag ccgtggtccg cgcgggggaa gccgagccga   720
gcggagccgc gagaagtgct agctcggccc gggaggagcc gcagccggag gaggggggagg   780
aggaagaaga gaaggaagag gagaggggggc cgcagtggcg actcggcgct cggaagccgg   840
```

```
gctcatggac gggtgaggcg gcggtgtgcg cagacagtgc tccagccgcg cgcgctcccc    900
aggccctggc ccgggcctcg ggccgggag  gaagagtagc tcgccgaggc gccgaggaga    960
gcgggccgcc ccacagcccg agccggagag ggagcgcgag ccgcgccggc cccggtcggg   1020
cctccgaaac catgaacttt ctgctgtctt gggtgcattg gagccttgcc ttgctgctct   1080
acctccacca tgccaagtgg tcccaggctg cacccatggc agaaggagga gggcagaatc   1140
atcacgaagt ggtgaagttc atggatgtct atcagcgcag ctactgccat ccaatcgaga   1200
ccctggtgga catcttccag gagtaccctg atgagatcga gtacatcttc aagccatcct   1260
gtgtgcccct gatgcgatgc ggggctgct  gcaatgacga gggcctggag tgtgtgccca   1320
ctgaggagtc caacatcacc atgcagatta tgcggatcaa acctcaccaa ggccagcaca   1380
taggagagat gagcttccta cagcacaaca atgtgaatg  cagaccaaag aaagatagag   1440
caagacaaga aaaaaaatca gttcgaggaa agggaaaggg gcaaaacga  aagcgcaaga   1500
aatcccggta taagtcctgg agcgttccct gtgggccttg ctcagagcgg agaaagcatt   1560
tgtttgtaca agatccgcag acgtgtaaat gttcctgcaa aaacagagac tcgcgttgca   1620
aggcgaggca gcttgagtta acgaacgta  cttgcagatg tgacaagccg aggcggtgag   1680
ccgggcagga ggaaggagcc tccctcaggg tttcgggaac cagatctctc accaggaaag   1740
actgatacag aacgatcgat acagaaacca cgctgccgcc accacaccat caccatcgac   1800
agaacagtcc ttaatccaga aacctgaaat gaaggaagag gagactctgc gcagagcact   1860
ttgggtccgg agggcgagac tccggcgaa  gcattcccgg gcgggtgacc cagcacggtc   1920
cctcttggaa ttggattcgc cattttattt ttcttgctgc taaatcaccg agcccggaag   1980
attagagagt tttatttctg ggattcctgt agacacaccc acccacatac atacatttat   2040
atatatatat attatatata tataaaaata aatatctcta ttttatatat ataaaatata   2100
tatattcttt ttttaaatta acagtgctaa tgttattggt gtcttcactg gatgtatttg   2160
actgctgtgg acttgagttg ggaggggaat gttcccactc agatcctgac agggaagagg   2220
aggagatgag agactctggc atgatctttt ttttgtccca cttggtgggg ccagggtcct   2280
ctcccctgcc caggaatgtg caaggccagg gcatgggggc aaatatgacc cagttttggg   2340
aacaccgaca aacccagccc tggcgctgag cctctctacc ccaggtcaga cggacagaaa   2400
gacagatcac aggtacaggg atgaggacac cggctctgac caggagtttg gggagcttca   2460
ggacattgct gtgctttggg gattccctcc acatgctgca cgcgcatctc gcccccaggg   2520
gcactgcctg gaagattcag gagcctgggc ggccttcgct tactctcacc tgcttctgag   2580
ttgcccagga gaccactggc agatgtcccg gcgaagagaa gagacacatt gttggaagaa   2640
gcagcccatg acagctcccc ttcctgggac tcgccctcat cctcttcctg ctccccttcc   2700
tggggtgcag cctaaaagga cctatgtcct cacaccattg aaaccactag ttctgtcccc   2760
ccaggagacc tggttgtgtg tgtgtgagtg gttgacttc  ctccatcccc tggtccttcc   2820
cttcccttcc cgaggcacag agagacaggg caggatccac gtgcccattg tggaggcaga   2880
gaaaagagaa agtgttttat atacggtact tatttaatat ccctttttaa ttagaaatta   2940
aaacagttaa tttaattaaa gagtagggtt ttttttcagt attcttggtt aatatttaat   3000
ttcaactatt tatgagatgt atcttttgct ctctcttgct ctcttatttg taccggtttt   3060
tgtatataaa attcatgttt ccaatctctc tctccctgat cggtgacagt cactagctta   3120
tcttgaacag atatttaatt ttgctaacac tcagctctgc cctccccgat cccctggctc   3180
cccagcacac attcctttga aataaggttt caatatacat ctacatacta tatatatatt   3240
```

-continued

| | |
|---|---|
| tggcaacttg tatttgtgtg tatatatata tatatatgtt tatgtatata tgtgattctg | 3300 |
| ataaaataga cattgctatt ctgtttttta tatgtaaaaa caaaacaaga aaaaatagag | 3360 |
| aattctacat actaaatctc tctccttttt taattttaat atttgttatc atttatttat | 3420 |
| tggtgctact gtttatccgt aataattgtg gggaaaagat attaacatca cgtctttgtc | 3480 |
| tctagtgcag tttttcgaga tattccgtag tacatattta tttttaaaca acgacaaaga | 3540 |
| aatacagata tatcttaaaa aaaaaaaagc attttgtatt aaagaattta attctgatct | 3600 |
| caaaaaaaaa aaaa | 3614 |

<210> SEQ ID NO 37
<211> LENGTH: 3596
<212> TYPE: DNA
<213> ORGANISM: Homo sapiens

<400> SEQUENCE: 37

| | |
|---|---|
| ggcttggggc agccgggtag ctcggaggtc gtggcgctgg gggctagcac cagcgctctg | 60 |
| tcgggaggcg cagcggttag gtggaccggt cagcggactc accggccagg gcgctcggtg | 120 |
| ctggaatttg atattcattg atccgggttt tatccctctt cttttttctt aaacattttt | 180 |
| ttttaaaact gtattgtttc tcgttttaat ttattttgc ttgccattcc ccacttgaat | 240 |
| cgggccgacg gcttgggag attgctctac ttccccaaat cactgtggat tttggaaacc | 300 |
| agcagaaaga ggaaagaggt agcaagagct ccagagagaa gtcgaggaag agagagacgg | 360 |
| ggtcagagag agcgcgcggg cgtgcgagca gcgaaagcga caggggcaaa gtgagtgacc | 420 |
| tgcttttggg ggtgaccgcc ggagcgcggc gtgagccctc cccccttggga tcccgcagct | 480 |
| gaccagtcgc gctgacggac agacagacag acaccgcccc cagccccagc taccacctcc | 540 |
| tccccggccg gcggcggaca gtggacgcgg cggcgagccg cgggcagggg ccggagcccg | 600 |
| cgcccgagg cggggtggag ggggtcgggg ctcgcggcgt cgcactgaaa cttttcgtcc | 660 |
| aacttctggg ctgttctcgc ttcggaggag ccgtggtccg cgcgggggaa gccgagccga | 720 |
| gcggagccgc gagaagtgct agctcggggcc gggaggagcc gcagccgagg gaggggagg | 780 |
| aggaagaaga gaaggaagag gagaggggc cgcagtggcg actcggcgct cggaagccgg | 840 |
| gctcatggac gggtgaggcg gcggtgtgcg cagacagtgc tccagccgcg cgcgctcccc | 900 |
| aggccctggc ccgggcctcg ggccggggag gaagagtagc tcgccgaggc gccgaggaga | 960 |
| gcgggccgcc ccacagcccg agccggagag ggagcgcgag ccgcgccggc cccggtcggg | 1020 |
| cctccgaaac catgaacttt ctgctgtctt gggtgcattg gagccttgcc ttgctgctct | 1080 |
| acctccacca tgccaagtgg tcccaggctg cacccatggc agaaggagga gggcagaatc | 1140 |
| atcacgaagt ggtgaagttc atggatgtct atcagcgcag ctactgccat ccaatcgaga | 1200 |
| ccctggtgga catcttccag gagtaccctg atgagatcga gtacatcttc aagccatcct | 1260 |
| gtgtgcccct gatgcgatgc ggggggctgct gcaatgacga gggcctggag tgtgtgccca | 1320 |
| ctgaggagtc caacatcacc atgcagatta tgcggatcaa acctcaccaa ggccagcaca | 1380 |
| taggagagat gagcttccta cagcacaaca atgtgaatg cagaccaaag aaagatagag | 1440 |
| caagacaaga aaaaaaatca gttcgaggaa agggaaaggg gcaaaacga aagcgcaaga | 1500 |
| aatcccgtcc ctgtgggcct tgctcagagc ggagaaagca tttgtttgta caagatccgc | 1560 |
| agacgtgtaa atgttcctgc aaaaacacag actcgcgttg caaggcgagg cagcttgagt | 1620 |
| taaacgaacg tacttgcaga tgtgacaagc cgaggcggtg agccgggcag gaggaaggag | 1680 |
| cctccctcag ggtttcggga accagatctc tcaccaggaa agactgatac agaacgatcg | 1740 |

```
atacagaaac cacgctgccg ccaccacacc atcaccatcg acagaacagt ccttaatcca   1800
gaaacctgaa atgaaggaag aggagactct gcgcagagca ctttgggtcc ggagggcgag   1860
actccggcgg aagcattccc gggcgggtga cccagcacgg tccctcttgg aattggattc   1920
gccattttat ttttcttgct gctaaatcac cgagcccgga agattagaga gttttatttc   1980
tgggattcct gtagacacac ccacccacat acatacattt atatatatat atattatata   2040
tatataaaaa taaatatctc tattttatat atataaaata tatatattct tttttttaaat  2100 taacagtgct aatgttattg gtgtcttcac tggatgtatt tgactgctgt ggacttgagt   2160 tgggaggggga atgttcccac tcagatcctg acagggaaga ggaggagatg agagactctg  2220
gcatgatctt ttttttgtcc cacttggtgg ggccagggtc ctctcccctg cccaggaatg   2280
tgcaaggcca gggcatgggg gcaaatatga cccagttttg gaacaccga caaacccagc    2340 cctggcgctg agcctctcta ccccaggtca gacggacaga aagacagatc acaggtacag   2400
ggatgaggac accggctctg accaggagtt tggggagctt caggacattg ctgtgctttg   2460
gggattccct ccacatgctg cacgcgcatc tcgcccccag gggcactgcc tggaagattc   2520
aggagcctgg gcggccttcg cttactctca cctgcttctg agttgcccag agaccactg    2580 gcagatgtcc cggcgaagag aagagacaca ttgttggaag aagcagccca tgacagctcc   2640
ccttcctggg actcgccctc atcctcttcc tgctccccctt cctggggtgc agcctaaaag  2700
gacctatgtc ctcacaccat tgaaaccact agttctgtcc ccccaggaga cctggttgtg   2760
tgtgtgtgag tggttgacct tcctccatcc cctggtcctt cccttcccctt cccgaggcac  2820 agagagacag ggcaggatcc acgtgcccat tgtggaggca gagaaaagag aaagtgtttt   2880
atatacggta cttatttaat atccctttttt aattagaaat taaaacagtt aatttaatta  2940
aagagtaggg ttttttttca gtattcttgg ttaatattta atttcaacta tttatgagat   3000 gtatctttttg ctctctcttg ctctcttatt tgtaccggtt tttgtatata aaattcatgt   3060
ttccaatctc tctctccctg atcggtgaca gtcactagct tatcttgaac agatatttaa   3120
ttttgctaac actcagctct gccctccccg atccctggc tccccagcac acattccttt    3180
gaaataaggt ttcaatatac atctacatac tatatatata tttggcaact tgtatttgtg   3240
tgtatatata tatatatatg tttatgtata tatgtgattc tgataaaata gacattgcta   3300
ttctgttttt tatatgtaaa aacaaaacaa gaaaaaatag agaattctac atactaaatc    3360
tctctccttt tttaatttta atatttgtta tcatttattt attggtgcta ctgtttatcc   3420
gtaataattg tgggaaaag atattaacat cacgtctttg tctctagtgc agttttcga    3480 gatattccgt agtacatatt tatttttaaa caacgacaaa gaaatacaga tatatcttaa   3540
aaaaaaaaaa gcattttgta ttaaagaatt taattctgat ctcaaaaaaa aaaaaa       3596
```

<210> SEQ ID NO 38
<211> LENGTH: 3542
<212> TYPE: DNA
<213> ORGANISM: Homo sapiens

<400> SEQUENCE: 38

```
ggcttggggc agccgggtag ctcggaggtc gtggcgctgg gggctagcac cagcgctctg    60
tcgggaggcg cagcggttag gtggaccggt cagcggactc accggccagg gcgctcggtg   120
ctggaatttg atattcattg atccgggttt tatccctctt cttttttctt aaacattttt   180
ttttaaaact gtattgtttc tcgttttaat ttatttttgc ttgccattcc ccacttgaat   240
cgggccgacg gcttggggag attgctctac ttccccaaat cactgtggat tttggaaacc   300
```

```
agcagaaaga ggaaagaggt agcaagagct ccagagagaa gtcgaggaag agagagacgg      360
ggtcagagag agcgcgcggg cgtgcgagca gcgaaagcga caggggcaaa gtgagtgacc      420
tgcttttggg ggtgaccgcc ggagcgcggc gtgagccctc ccccttggga tcccgcagct      480
gaccagtcgc gctgacggac agacagacag acaccgcccc cagccccagc taccacctcc      540
tccccggccg gcggcggaca gtggacgcgg cggcgagccg cgggcagggg ccggagcccg      600
cgcccggagg cggggtggag ggggtcgggg ctcgcggcgt cgcactgaaa cttttcgtcc      660
aacttctggg ctgttctcgc ttcggaggag ccgtggtccg cgcggggggaa gccgagccga     720 gcggagccgc gagaagtgct agctcgggcc gggaggagcc gcagccgag gaggggggagg      780 aggaagaaga gaaggaagag gagagggggc gcagtggcg actcggcgct cggaagccgg      840
gctcatggac gggtgaggcg gcggtgtgcg cagacagtgc tccagccgcg cgcgctcccc      900
aggccctggc ccgggcctcg ggccggggag gaaagagtagc tcgccgaggc gccgaggaga     960
gcgggccgcc ccacagcccg agccggagag ggagcgcgag ccgcgccggc cccggtcggg    1020
cctccgaaac catgaacttt ctgctgtctt gggtgcattg gagccttgcc ttgctgctct    1080
acctccacca tgccaagtgg tcccaggctg cacccatggc agaaggagga gggcagaatc    1140
atcacgaagt ggtgaagttc atggatgtct atcagcgcag ctactgccat ccaatcgaga    1200
ccctggtgga catcttccag gagtaccctg atgagatcga gtacatcttc aagccatcct    1260
gtgtgcccct gatgcgatgc gggggctgct gcaatgacga gggcctggag tgtgtgccca    1320
ctgaggagtc caacatcacc atgcagatta tgcggatcaa acctcaccaa ggccagcaca    1380
taggagagat gagcttccta cagcacaaca aatgtgaatg cagaccaaag aaagatagag    1440
caagacaaga aaatccctgt gggccttgct cagagcggag aaagcatttg tttgtacaag    1500
atccgcagac gtgtaaatgt tcctgcaaaa acacagactc gcgttgcaag gcgaggcagc    1560
ttgagttaaa cgaacgtact tgcagatgtg acaagccgag gcggtgagcc gggcaggagg    1620
aaggagcctc cctcagggtt tcgggaacca gatctctcac caggaaagac tgatacagaa    1680
cgatcgatac agaaaccacg ctgccgccac cacaccatca ccatcgacag aacagtcctt    1740
aatccagaaa cctgaaatga aggaagagga gactctgcgc agagcacttt gggtccggag    1800
ggcgagactc cggcggaagc attcccgggc gggtgaccca gcacggtccc tcttggaatt    1860
ggattcgcca ttttatttt cttgctgcta aatcaccgag cccggaagat tagagagttt    1920
tatttctggg attcctgtag acacacccac ccacatacat acatttatat atatatatat    1980
tatatatata taaaaataaa tatctctatt ttatatatat aaaatatata tattcttttt    2040
ttaaattaac agtgctaatg ttattggtgt cttcactgga tgtatttgac tgctgtggac    2100
ttgagttggg aggggaatgt tcccactcag atcctgacag ggaagaggag gagatgagag    2160
actctggcat gatctttttt ttgtcccact tggtggggcc agggtcctct cccctgccca    2220
ggaatgtgca aggccagggc atgggggcaa atatgcccca gttttgggaa caccgacaaa    2280
cccagccctg gcgctgagcc tctctacccc aggtcagacg gacagaaaga cagatcacag    2340
gtacagggat gaggacaccg gctctgacca ggagtttggg gagcttcagg acattgctgt    2400
gctttgggga ttccctccac atgctgcacg cgcatctcgc cccagggggc actgcctgga    2460
agattcagga gcctggcggg ccttcgctta ctctcacctg cttctgagtt gcccaggaga    2520
ccactggcag atgtcccggc gaagagaaga gacacattgt tggaagaagc agcccatgac    2580
agctcccctt cctgggactc gccctcatcc tcttcctgct cccctcctg gggtgcagcc     2640 taaaaggacc tatgtcctca caccattgaa accactagtt ctgtcccccc aggagacctg    2700
```

```
gttgtgtgtg tgtgagtggt tgaccttcct ccatcccctg gtccttccct tcccttcccg    2760
aggcacagag agacagggca ggatccacgt gcccattgtg gaggcagaga aaagagaaag    2820
tgttttatat acggtactta tttaatatcc cttttaatt agaaattaaa acagttaatt    2880
taattaaaga gtagggtttt ttttcagtat tcttggttaa tatttaattt caactattta    2940
tgagatgtat cttttgctct ctcttgctct cttatttgta ccggttttg tatataaaat    3000 tcatgtttcc aatctctctc tccctgatcg gtgacagtca ctagcttatc ttgaacagat    3060
atttaatttt gctaacactc agctctgccc tccccgatcc cctggctccc cagcacacat    3120 tccttttgaaa taaggtttca atatacatct acatactata tatatatttg gcaacttgta    3180
tttgtgtgta tatatatata tatatgttta tgtatatatg tgattctgat aaaatagaca    3240
ttgctattct gttttttata tgtaaaaaca aacaagaaa aaatagagaa ttctacatac    3300
taaatctctc tccttttta attttaatat ttgttatcat ttatttattg gtgctactgt    3360
ttatccgtaa taattgtggg gaaaagatat taacatcacg tctttgtctc tagtgcagtt    3420
tttcgagata ttccgtagta catatttatt tttaaacaac gacaaagaaa tacagatata    3480
tcttaaaaaa aaaaaagcat tttgtattaa agaatttaat tctgatctca aaaaaaaaaa    3540
aa                                                                   3542

<210> SEQ ID NO 39
<211> LENGTH: 3507
<212> TYPE: DNA
<213> ORGANISM: Homo sapiens

<400> SEQUENCE: 39
ggcttggggc agccgggtag ctcggaggtc gtggcgctgg gggctagcac cagcgctctg      60
tcgggaggcg cagcggttag gtggaccggt cagcggactc accggccagg gcgctcggtg     120
ctggaatttg atattcattg atccgggttt tatccctctt cttttttctt aaacattttt     180
ttttaaaact gtattgtttc tcgttttaat ttatttttgc ttgccattcc ccacttgaat     240
cgggccgacg gcttgggag attgctctac ttccccaaat cactgtggat tttggaaacc     300
agcagaaaga ggaaagaggt agcaagagct ccagagagaa gtcgaggaag agagagacgg     360
ggtcagagag agcgcgcggg cgtgcgagca gcgaaagcga caggggcaaa gtgagtgacc     420
tgcttttggg ggtgaccgcc ggagcgcggc gtgagccctc cccttggga tcccgcagct     480 gaccagtcgc gctgacggac agacagacag acaccgcccc cagccccagc taccacctcc     540
tccccggccg gcgcggaca gtggacgcgg cggcgagccg cgggcagggg ccggagcccg     600
cgcccggagg cggggtggag ggggtcgggg ctcgcggcgt cgcactgaaa cttttcgtcc     660
aacttctggg ctgttctcgc ttcggaggag ccgtggtccg cgcggggaa gccgagccga     720 gcggagccgc gagaagtgct agctcgggcc gggaggagcc gcagccggag gaggggagg     780 aggaagaaga gaaggaagag gagagggggc cgcagtggcg actcggcgct cggaagccgg     840
gctcatggac gggtgaggcg gcggtgtgcg cagacagtgc tccagccgcg cgcgctcccc     900
aggccctggc ccgggcctcg ggccggggag gaagagtagc tcgccgaggc gccgaggaga     960
gcgggccgcc ccacagcccg agccggagag ggagcgcgag ccgcgccggc cccggtcggg    1020
cctccgaaac catgaacttt ctgctgtctt gggtgcattg gagccttgcc ttgctgctct    1080
acctccacca tgccaagtgg tcccaggctg cacccatggc agaaggagga gggcagaatc    1140
atcacgaagt ggtgaagttc atggatgtct atcagcgcag ctactgccat ccaatcgaga    1200
ccctggtgga catcttccag gagtaccctg atgagatcga gtacatcttc aagccatcct    1260
```

```
gtgtgcccct gatgcgatgc gggggctgct gcaatgacga gggcctggag tgtgtgccca    1320
ctgaggagtc caacatcacc atgcagatta tgcggatcaa acctcaccaa ggccagcaca    1380
taggagagat gagcttccta cagcacaaca aatgtgaatg cagaccaaag aaagatagag    1440
caagacaaga aaatccctgt gggccttgct cagagcggag aaagcatttg tttgtacaag    1500
atccgcagac gtgtaaatgt tcctgcaaaa acacagactc gcgttgcaag atgtgacaag    1560
ccgaggcggt gagccgggca ggaggaagga gcctccctca gggtttcggg aaccagatct    1620
ctcaccagga aagactgata cagaacgatc gatacagaaa ccacgctgcc gccaccacac    1680
catcaccatc gacagaacag tccttaatcc agaaacctga atgaaggaa gaggagactc    1740 tgcgcagagc actttgggtc cggagggcga gactccggcg aagcattcc cgggcgggtg    1800 acccagcacg gtccctcttg gaattggatt cgccatttta ttttttcttgc tgctaaatca    1860 ccgagcccgg aagattagag agttttattt ctgggattcc tgtagacaca cccacccaca    1920
tacatacatt tatatatata tatattatat atatataaaa ataaatatct ctattttata    1980
tatataaaat atatatattc ttttttttaaa ttaacagtgc taatgttatt ggtgtcttca    2040
ctggatgtat ttgactgctg tggacttgag ttgggagggg aatgttccca ctcagatcct    2100
gacagggaag aggaggagat gagagactct ggcatgatct ttttttttgtc ccacttggtg    2160 gggccagggt cctctcccct gcccaggaat gtgcaaggcc agggcatggg ggcaaatatg    2220
acccagtttt gggaacaccg acaaacccag ccctggcgct gagcctctct accccaggtc    2280
agacggacag aaagacagat cacaggtaca gggatgagga caccggctct gaccaggagt    2340
ttggggagct tcaggacatt gctgtgcttt ggggattccc tccacatgct gcacgcgcat    2400
ctcgccccca gggcactgc ctggaagatt caggagcctg gcggccttc gcttactctc    2460 acctgcttct gagttgccca ggagaccact ggcagatgtc ccggcgaaga gaagagacac    2520
attgttggaa gaagcagccc atgacagctc cccttcctgg gactcgccct catcctcttc    2580
ctgctcccct tcctggggtg cagcctaaaa ggacctatgt cctcacacca ttgaaaccac    2640
tagttctgtc cccccaggag acctggttgt gtgtgtgtga gtggttgacc ttcctccatc    2700
ccctggtcct tcccttccct tcccgaggca cagagagaca gggcaggatc cacgtgccca    2760
ttgtggaggc agagaaaaga gaaagtgttt tatatacggt acttatttaa tatcccttt    2820 taattagaaa ttaaaacagt taatttaatt aaagagtagg gttttttttc agtattcttg    2880 gttaatatt aatttcaact atttatgaga tgtatctttt gctctctctt gctctcttat    2940
ttgtaccggt tttttgtatat aaaattcatg tttccaatct ctctctccct gatcggtgac    3000
agtcactagc ttatcttgaa cagatattta atttttgctaa cactcagctc tgccctcccc    3060 gatccctgg ctccccagca cacattcctt tgaaataagg tttcaatata catctacata    3120
ctatatatat atttggcaac ttgtatttgt gtgtatatat atatatatat gtttatgtat    3180
atatgtgatt ctgataaaat agacattgct attctgtttt ttatatgtaa aaacaaaaca    3240
agaaaaaata gagaattcta catactaaat ctctctcctt ttttaatttt aatatttgtt    3300
atcatttatt tattggtgct actgtttatc cgtaataatt gtggggaaaa gatattaaca    3360
tcacgtcttt gtctctagtg cagttttttcg agatattccg tagtacatat ttatttttaa    3420
acaacgacaa agaaatacag atatatctta aaaaaaaaaa agcattttgt attaaagaat    3480
ttaattctga tctcaaaaaa aaaaaaa                                         3507

<210> SEQ ID NO 40
<211> LENGTH: 3410
<212> TYPE: DNA
```

<213> ORGANISM: Homo sapiens

<400> SEQUENCE: 40

```
ggcttggggc agccgggtag ctcggaggtc gtggcgctgg gggctagcac cagcgctctg      60
tcggaggcg cagcggttag gtggaccggt cagcggactc accggccagg cgctcggtg      120
ctggaatttg atattcattg atccgggttt tatccctctt ctttttttctt aaacattttt    180
ttttaaaact gtattgtttc tcgttttaat ttattttttgc ttgccattcc ccacttgaat    240
cgggccgacg gcttgggag attgctctac ttccccaaat cactgtggat tttggaaacc     300
agcagaaaga ggaaagaggt agcaagagct ccagagagaa gtcgaggaag agagagacgg    360
ggtcagagag agcgcgcggg cgtgcgagca gcgaaagcga caggggcaaa gtgagtgacc    420
tgcttttggg ggtgaccgcc ggagcgcggc gtgagccctc ccccttggga tcccgcagct    480
gaccagtcgc gctgacggac agacagacag acaccgcccc cagccccagc taccacctcc    540
tccccggccg gcggcggaca gtggacgcgg cggcgagccg cgggcagggg ccggagcccg    600
cgcccggagg cggggtggag ggggtcgggg ctcgcggcgt cgcactgaaa ctttttcgtcc    660
aacttctggg ctgttctcgc ttcggaggag ccgtggtccg cgcggggggaa gccgagccga    720
gcggagccgc gagaagtgct agctcgggcc gggaggagcc gcagccggag gagggggagg    780
aggaagaaga gaaggaagag gagaggggggc cgcagtggcg actcggcgct cggaagccgg    840
gctcatggac gggtgaggcg gcggtgtgcg cagacagtgc tccagccgcg cgcgctcccc    900
aggccctggc ccgggcctcg ggccggggag gaagagtagc tcgccgaggc gccgaggaga    960
gcgggccgcc ccacagcccg agccggagag ggagcgcgag ccgcgccggc cccggtcggg   1020
cctccgaaac catgaacttt ctgctgtctt gggtgcattg gagccttgcc ttgctgctct   1080
acctccacca tgccaagtgg tcccaggctg cacccatggc agaaggagga gggcagaatc   1140
atcacgaagt ggtgaagttc atggatgtct atcagcgcag ctactgccat ccaatcgaga   1200
ccctggtgga catcttccag gagtaccctg atgagatcga gtacatcttc aagccatcct   1260
gtgtgcccct gatgcgatgc ggggggctgct gcaatgacga gggcctggag tgtgtgccca   1320
ctgaggagtc caacatcacc atgcagatta tgcggatcaa acctcaccaa ggccagcaca   1380
taggagagat gagcttccta cagcacaaca atgtgaatg cagaccaaag aaagatagag   1440
caagacaaga aaatgtgac aagccgaggc ggtgagccgg caggaggaa ggagcctccc    1500
tcagggtttc gggaaccaga tctctcacca ggaaagactg atacagaacg atcgatacag   1560
aaaccacgct gccgccacca caccatcacc atcgacagaa cagtccttaa tccagaaacc   1620
tgaaatgaag gaagaggaga ctctgcgcag agcactttgg gtccggaggg cgagactccg   1680
gcggaagcat tccgggcgg gtgacccagc acggtccctc ttggaattgg attcgccatt    1740
ttatttttct tgctgctaaa tcaccgagcc cggaagatta gagagtttta tttctgggat   1800
tcctgtagac acacccaccc acatacatac atttatatat atatatatta tatatatata   1860
aaaataaata tctctatttt atatatataa aatatatata ttcttttttt aaattaacag   1920
tgctaatgtt attggtgtct tcactggatg tatttgactg ctgtggactt gagttgggag   1980
gggaatgttc ccactcagat cctgacaggg aagaggagga gatgagagac tctggcatga   2040
tcttttttttt gtcccacttg gtggggccag ggtcctctcc cctgcccagg aatgtgcaag   2100
gccagggcat gggggcaaat atgacccagt tttgggaaca ccgacaaacc cagccctggc   2160
gctgagcctc tctaccccag gtcagacgga cagaaagaca gatcacaggt acagggatga   2220
ggacaccggc tctgaccagg agtttgggga gcttcaggac attgctgtgc tttggggatt   2280
```

| | |
|---|---|
| ccctccacat gctgcacgcg catctcgccc cagggggcac tgcctggaag attcaggagc | 2340 |
| ctgggcggcc ttcgcttact ctcacctgct tctgagttgc ccaggagacc actggcagat | 2400 |
| gtcccggcga agagaagaga cacattgttg gaagaagcag cccatgacag ctccccttcc | 2460 |
| tgggactcgc cctcatcctc ttcctgctcc ccttcctggg gtgcagccta aaaggaccta | 2520 |
| tgtcctcaca ccattgaaac cactagttct gtccccccag gagacctggt tgtgtgtgtg | 2580 |
| tgagtggttg accttcctcc atccctggt ccttcccttc ccttcccgag cacagagag | 2640 |
| acagggcagg atccacgtgc ccattgtgga ggcagagaaa agagaaagtg ttttatatac | 2700 |
| ggtacttatt taatatccct tttaattag aaattaaaac agttaattta attaaagagt | 2760 |
| agggttttt ttcagtattc ttggttaata tttaatttca actatttatg agatgtatct | 2820 |
| tttgctctct cttgctctct tatttgtacc ggttttgta tataaaattc atgtttccaa | 2880 |
| tctctctctc cctgatcggt gacagtcact agcttatctt gaacagatat ttaattttgc | 2940 |
| taacactcag ctctgccctc cccgatcccc tggctcccca gcacacattc ctttgaaata | 3000 |
| aggtttcaat atacatctac atactatata tatatttggc aacttgtatt tgtgtgtata | 3060 |
| tatatatata tatgttttatg tatatatgtg attctgataa aatagacatt gctattctgt | 3120 |
| ttttatatg taaaaacaaa acaagaaaaa atagagaatt ctacatacta aatctctctc | 3180 |
| cttttttaat tttaatattt gttatcattt atttattggt gctactgttt atccgtaata | 3240 |
| attgtgggga aaagatatta acatcacgtc tttgtctcta gtgcagtttt tcgagatatt | 3300 |
| ccgtagtaca tatttatttt taaacaacga caaagaaata cagatatatc ttaaaaaaaa | 3360 |
| aaaagcattt tgtattaaag aatttaattc tgatctcaaa aaaaaaaaaa | 3410 |

<210> SEQ ID NO 41
<211> LENGTH: 3476
<212> TYPE: DNA
<213> ORGANISM: Homo sapiens

<400> SEQUENCE: 41

| | |
|---|---|
| ggcttggggc agccgggtag ctcggaggtc gtggcgctgg gggctagcac cagcgctctg | 60 |
| tcgggaggcg cagcggttag gtggaccggt cagcggactc accggccagg gcgctcggtg | 120 |
| ctggaatttg atattcattg atccgggttt tatccctctt cttttttctt aaacattttt | 180 |
| ttttaaaact gtattgtttc tcgttttaat ttattttgc ttgccattcc ccacttgaat | 240 |
| cgggccgacg gcttggggag attgctctac ttccccaaat cactgtggat tttggaaacc | 300 |
| agcagaaaga ggaaagaggt agcaagagct ccagagagaa gtcgaggaag agagagacgg | 360 |
| ggtcagagag agcgcgcggg cgtgcgagca gcgaaagcga caggggcaaa gtgagtgacc | 420 |
| tgcttttggg ggtgaccgcc ggagcgcggc gtgagccctc cccttggga tcccgcagct | 480 |
| gaccagtcgc gctgacggac agacagacag acaccgcccc cagcccagc taccacctcc | 540 |
| tcccccggccg gcgcggaca gtggacgcgg cggcgagccg cgggcagggg ccggagcccg | 600 |
| cgcccggagg cggggtggag ggggtcgggg ctcgcggcgt cgcactgaaa cttttcgtcc | 660 |
| aacttctggg ctgttctcgc ttcggaggag ccgtggtccg cgcggggaa gccgagccga | 720 |
| gcggagccgc gagaagtgct agctcgggcc ggaggagcc gcagccggag gagggggagg | 780 |
| aggaagaaga gaaggaagag gagagggggc cgcagtggcg actcggcgct cggaagccgg | 840 |
| gctcatggac gggtgaggcg gcggtgtgcg cagacagtgc tccagccgcg cgcgctcccc | 900 |
| aggccctggc ccgggcctcg ggccgggag gaagagtagc tcgccgaggc gccgaggaga | 960 |
| gcgggccgcc ccacagcccg agccggagag ggagcgcgag ccgcgccggc cccggtcggg | 1020 |

```
cctccgaaac catgaacttt ctgctgtctt gggtgcattg gagccttgcc ttgctgctct    1080
acctccacca tgccaagtgg tcccaggctg cacccatggc agaaggagga gggcagaatc    1140
atcacgaagt ggtgaagttc atggatgtct atcagcgcag ctactgccat ccaatcgaga    1200
ccctggtgga catcttccag gagtaccctg atgagatcga gtacatcttc aagccatcct    1260
gtgtgcccct gatgcgatgc gggggctgct gcaatgacga gggcctggag tgtgtgccca    1320
ctgaggagtc caacatcacc atgcagatta tgcggatcaa acctcaccaa ggccagcaca    1380
taggagagat gagcttccta cagcacaaca aatgtgaatg cagaccaaag aaagatagag    1440
caagacaaga aaatccctgt gggccttgct cagagcggag aaagcatttg tttgtacaag    1500
atccgcagac gtgtaaatgt tcctgcaaaa acacagactc gcgttgcaag gcgaggcagc    1560
ttgagttaaa cgaacgtact tgcagatctc tcaccaggaa agactgatac agaacgatcg    1620
atacagaaac cacgctgccg ccaccacacc atcaccatcg acagaacagt ccttaatcca    1680
gaaacctgaa atgaaggaag aggagactct gcgcagagca ctttgggtcc ggagggcgag    1740
actccggcgg aagcattccc gggcgggtga cccagcacgg tccctcttgg aattggattc    1800 gccatttat ttttcttgct gctaaatcac cgagcccgga agattagaga gttttatttc    1860
tgggattcct gtagacacac ccacccacat acatacattt atatatatat atattatata    1920
tatataaaaa taaatatctc tattttatat atataaaata tatatattct tttttaaat    1980 taacagtgct aatgttattg gtgtcttcac tggatgtatt tgactgctgt ggacttgagt    2040
tgggagggga atgttcccac tcagatcctg acagggaaga ggaggagatg agagactctg    2100
gcatgatctt tttttgtcc cacttggtgg ggccagggtc ctctcccctg cccaggaatg    2160
tgcaaggcca gggcatgggg gcaaatatga cccagttttg ggaacaccga caaacccagc    2220
cctggcgctg agcctctcta ccccaggtca gacggacaga aagacagatc acaggtacag    2280
ggatgaggac accggctctg accaggagtt tggggagctt caggacattg ctgtgctttg    2340
gggattccct ccacatgctg cacgcgcatc tcgcccccag gggcactgcc tggaagattc    2400
aggagcctgg gcggccttcg cttactctca cctgcttctg agttgcccag gagaccactg    2460
gcagatgtcc cggcgaagag aagagacaca ttgttggaag aagcagccca tgacagctcc    2520
ccttcctggg actcgccctc atcctcttcc tgctccccctt cctggggtgc agcctaaaag    2580
gacctatgtc ctcacaccat tgaaaccact agttctgtcc ccccaggaga cctggttgtg    2640
tgtgtgtgag tggttgacct tcctccatcc cctggtcctt cccttccctt cccgaggcac    2700
agagagacag ggcaggatcc acgtgccat tgtggaggca gagaaaagag aaagtgtttt    2760
atatacggta cttatttaat atcccttttt aattagaaat taaaacagtt aatttaatta    2820
aagagtaggg ttttttttca gtattcttgg ttaatattta atttcaacta tttatgagat    2880
gtatcttttg ctctctcttg ctctcttatt tgtaccggtt tttgtatata aaattcatgt    2940
ttccaatctc tctctccctg atcggtgaca gtcactagct tatcttgaac agatatttaa    3000
ttttgctaac actcagctct gccctccccg atccctggc tccccagcac acattccttt    3060
gaaataaggt ttcaatatac atctacatac tatatatata tttggcaact tgtatttgtg    3120
tgtatatata tatatatatg tttatgtata tatgtgattc tgataaaata gacattgcta    3180
ttctgttttt tatatgtaaa aacaaaacaa gaaaaaatag agaattctac atactaaatc    3240
tctctccttt tttaattta atatttgtta tcatttattt attggtgcta ctgtttatcc    3300
gtaataattg tggggaaaag atattaacat cacgtctttg tctctagtgc agttttcga    3360 gatattccgt agtacatatt tattttaaa caacgacaaa gaaatacaga tatatcttaa    3420
```

-continued aaaaaaaaaa gcattttgta ttaaagaatt taattctgat ctcaaaaaaa aaaaaa        3476

<210> SEQ ID NO 42
<211> LENGTH: 21
<212> TYPE: DNA
<213> ORGANISM: Homo sapiens
<220> FEATURE:
<221> NAME/KEY: misc_feature
<222> LOCATION: (0803)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 0803. The two 5' nucleotides AA are optional in MB0803.

<400> SEQUENCE: 42
aagggtgtgt atgtgcccta c                                              21

<210> SEQ ID NO 43
<211> LENGTH: 21
<212> TYPE: DNA
<213> ORGANISM: Homo sapiens
<220> FEATURE:
<221> NAME/KEY: misc_feature
<222> LOCATION: (1663)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1663. The two 5' nucleotides AA are optional in MB1663.

<400> SEQUENCE: 43
aattggcttt gctgtcagcg c                                              21

<210> SEQ ID NO 44
<211> LENGTH: 21
<212> TYPE: DNA
<213> ORGANISM: Homo sapiens
<220> FEATURE:
<221> NAME/KEY: misc_feature
<222> LOCATION: (1749)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 1749. The two 5' nucleotides AA are optional in MB1749.

<400> SEQUENCE: 44
aagactgtgg ctacaacatt c                                              21

<210> SEQ ID NO 45
<211> LENGTH: 21
<212> TYPE: DNA
<213> ORGANISM: Homo sapiens
<220> FEATURE:
<221> NAME/KEY: misc_feature
<222> LOCATION: (3249)..()
<223> OTHER INFORMATION: Starting position within mouse BACE1 cDNA
      (Genbank Accession NM_011792) and corresponding human sequences.
      DNA sequence corresponding to the therapeutic siRNA starting at
      base 3249. The two 5' nucleotides AA are optional in MB3249.

<400> SEQUENCE: 45
aaggctgcct ggagaaagga t                                              21

<210> SEQ ID NO 46
<211> LENGTH: 21
<212> TYPE: DNA
<213> ORGANISM: Homo sapiens
<220> FEATURE:
<221> NAME/KEY: misc_feature
<222> LOCATION: (0916)..()
<223> OTHER INFORMATION: Starting position within mouse BACE1 cDNA
      (Genbank Accession NM_011792) and corresponding human sequences.

```
                DNA sequence corresponding to the therapeutic siRNA starting at
                base 0916. The two 5' nucleotides CA are optional in DhMB0918.

<400> SEQUENCE: 46
cactgaatcg gacaagttct t                                              21

<210> SEQ ID NO 47
<211> LENGTH: 21
<212> TYPE: DNA
<213> ORGANISM: Homo sapiens
<220> FEATURE:
<221> NAME/KEY: misc_feature
<222> LOCATION: (1129)..()
<223> OTHER INFORMATION: Starting position within mouse BACE1 cDNA
                (Genbank Accession NM_011792) and corresponding human sequences.
                DNA sequence corresponding to the therapeutic siRNA starting at
                base 1129. The two 5' nucleotides CA are optional in DhMB1131.

<400> SEQUENCE: 47
catgatcatt ggtggtatcg a                                              21

<210> SEQ ID NO 48
<211> LENGTH: 21
<212> TYPE: DNA
<213> ORGANISM: Homo sapiens
<220> FEATURE:
<221> NAME/KEY: misc_feature
<222> LOCATION: (1231)..()
<223> OTHER INFORMATION: Starting position within mouse BACE1 cDNA
                (Genbank Accession NM_011792) and corresponding human sequences.
                DNA sequence corresponding to the therapeutic siRNA starting at
                base 1231. The two 5' nucleotides AA are optional in DhMB1233.

<400> SEQUENCE: 48
catccttcct cagcaatacc t                                              21

<210> SEQ ID NO 49
<211> LENGTH: 21
<212> TYPE: DNA
<213> ORGANISM: Homo sapiens
<220> FEATURE:
<221> NAME/KEY: misc_feature
<222> LOCATION: (0683)..()
<223> OTHER INFORMATION: Starting position within mouse BACE1 cDNA
                (Genbank Accession NM_011792) and corresponding human sequences.
                DNA sequence corresponding to the therapeutic siRNA starting at
                base 0683. The two 5' nucleotides CA are optional in SEC0683.

<400> SEQUENCE: 49
cagacgctca acatcctggt g                                              21

<210> SEQ ID NO 50
<211> LENGTH: 19
<212> TYPE: DNA
<213> ORGANISM: Homo sapiens

<400> SEQUENCE: 50
ctacgaacct gaagcctaa                                                 19

<210> SEQ ID NO 51
<211> LENGTH: 19
<212> TYPE: DNA
<213> ORGANISM: Homo sapiens

<400> SEQUENCE: 51
tcaagactac gaacctgaa                                                 19

<210> SEQ ID NO 52
```

-continued

```
<211> LENGTH: 19
<212> TYPE: DNA
<213> ORGANISM: Homo sapiens

<400> SEQUENCE: 52
cattagccat ggatgtatt                                                   19

<210> SEQ ID NO 53
<211> LENGTH: 19
<212> TYPE: DNA
<213> ORGANISM: Homo sapiens

<400> SEQUENCE: 53
acgaacctga agcctaaga                                                   19

<210> SEQ ID NO 54
<211> LENGTH: 19
<212> TYPE: DNA
<213> ORGANISM: Homo sapiens

<400> SEQUENCE: 54
gtacaagtgc tcagttcca                                                   19

<210> SEQ ID NO 55
<211> LENGTH: 19
<212> TYPE: DNA
<213> ORGANISM: Homo sapiens

<400> SEQUENCE: 55
gcttcaatct acgatgtta                                                   19

<210> SEQ ID NO 56
<211> LENGTH: 19
<212> TYPE: DNA
<213> ORGANISM: Homo sapiens

<400> SEQUENCE: 56
ctaagtgact accacttat                                                   19

<210> SEQ ID NO 57
<211> LENGTH: 19
<212> TYPE: DNA
<213> ORGANISM: Homo sapiens

<400> SEQUENCE: 57
gttcagaagt tgttagtga                                                   19

<210> SEQ ID NO 58
<211> LENGTH: 19
<212> TYPE: DNA
<213> ORGANISM: Homo sapiens

<400> SEQUENCE: 58
agttgttagt gatttgcta                                                   19

<210> SEQ ID NO 59
<211> LENGTH: 19
<212> TYPE: DNA
<213> ORGANISM: Homo sapiens

<400> SEQUENCE: 59
gacgtattgt gaaatttgt                                                   19

<210> SEQ ID NO 60
```

```
<211> LENGTH: 19
<212> TYPE: DNA
<213> ORGANISM: Homo sapiens

<400> SEQUENCE: 60
tcatcaattt cgagcagaa                                                      19

<210> SEQ ID NO 61
<211> LENGTH: 19
<212> TYPE: DNA
<213> ORGANISM: Homo sapiens

<400> SEQUENCE: 61
tgagtttgga gataataca                                                      19

<210> SEQ ID NO 62
<211> LENGTH: 19
<212> TYPE: DNA
<213> ORGANISM: Homo sapiens

<400> SEQUENCE: 62
tggccgatgt gtctattga                                                      19

<210> SEQ ID NO 63
<211> LENGTH: 19
<212> TYPE: DNA
<213> ORGANISM: Homo sapiens

<400> SEQUENCE: 63
cgatgtgtct attgaagat                                                      19

<210> SEQ ID NO 64
<211> LENGTH: 19
<212> TYPE: DNA
<213> ORGANISM: Homo sapiens

<400> SEQUENCE: 64
gcattaaagg actgactga                                                      19

<210> SEQ ID NO 65
<211> LENGTH: 19
<212> TYPE: DNA
<213> ORGANISM: Homo sapiens

<400> SEQUENCE: 65
tcgtttggct tgtggtgta                                                      19

<210> SEQ ID NO 66
<211> LENGTH: 21
<212> TYPE: DNA
<213> ORGANISM: Homo sapiens

<400> SEQUENCE: 66
aatttcgagc agaaggaaag t                                                   21

<210> SEQ ID NO 67
<211> LENGTH: 21
<212> TYPE: DNA
<213> ORGANISM: Homo sapiens

<400> SEQUENCE: 67
aagcattaaa ggactgactg a                                                   21

<210> SEQ ID NO 68
```

```
<211> LENGTH: 21
<212> TYPE: DNA
<213> ORGANISM: Homo sapiens

<400> SEQUENCE: 68
aatgtgactg ctgacaaaga t                                              21

<210> SEQ ID NO 69
<211> LENGTH: 21
<212> TYPE: DNA
<213> ORGANISM: Homo sapiens

<400> SEQUENCE: 69
aagattctgt gatctcactc t                                              21

<210> SEQ ID NO 70
<211> LENGTH: 33
<212> TYPE: DNA
<213> ORGANISM: Artificial Sequence
<220> FEATURE:
<223> OTHER INFORMATION: loxP sequence

<400> SEQUENCE: 70
ctacttcgta tagcatacat tatacgaagt tat                                 33

<210> SEQ ID NO 71
<211> LENGTH: 34
<212> TYPE: DNA
<213> ORGANISM: Artificial Sequence
<220> FEATURE:
<223> OTHER INFORMATION: loxP sequence

<400> SEQUENCE: 71
ataacttcgt atagcataca ttatacgaag ttat                                34
```

THERAPEUTING COMPOSITIONS COMPRISING AN RNAI AGENT AND A NEUROTROPHIC FACTOR AND METHODS OF USE THEREOF

RELATED APPLICATIONS

The present application is Continuation-in-Part application of U.S. application Ser. No. 12/522,153, now pending, filed on Jul. 3, 2009 as a 35 U.S.C. §371 National Phase application of International Application Serial No. PCT/US2008/50089 filed Jan. 3, 2008, which claims priority under 35 U.S.C. §119 to a U.S. Provisional application 60/878,371 filed on Jan. 3, 2007. The disclosures of the parent applications are incorporated herein by reference in their entirety.

FIELD OF THE INVENTION

The instant invention is most closely related to using RNA inhibition for treatment of neurodegenerative diseases.

BACKGROUND

Neurodegenerative disorders (NDs) are a group of related human maladies that share a common pathophysiological feature, the progressive degeneration of selective neuronal populations over the course of time. Despite significant progress in elucidating the genetic causes underlying these disparate disorders, relatively little is known about the biochemical mechanisms that cause the selective neuronal degeneration common to all of them.

One of these diseases, Huntington's Disease (HD), leads to lots of striatal neurons, resulting in both physical and mental disabilities. Symptoms usually appear between the ages of 30 and 50 but can begin as early as 2 and as old as 80. People with Huntington's Disease require care from health professionals of many stripes, including general practitioners, neurologists, social workers, home health aides, psychologists, physical therapists, and speech/language pathologists.

Huntington's Disease Society of America estimates that approximately a quarter of a million Americans have Huntington's Disease or are at risk of inheriting the HD mutation. The cost of caring for patients with neurodegenerative diseases is enormous. For example, combined with the expense of long-term care and the impact of lost productivity, the cost of Huntington's Disease and related disorders is estimated at 2.5 billion dollars.

With the number of individuals affected with neurodegenerative disorders and the costs associated with caring for these individuals, there is a dire need for novel therapies that prevent and treat these conditions.

SUMMARY OF INVENTION

This invention addresses this need by providing, in a first aspect, a first nucleic acid sequence comprising: a second nucleic acid sequence encoding BDNF or a functional fragment thereof; and a third nucleic acid sequence encoding an RNAi agent capable of inhibiting expression of huntingtin, said RNAi agent comprising a double-stranded structure having a first strand and a second strand, said first and second strands each being between 19 and 30 nucleotides long, wherein the first strand is encoded by a sequence comprising any one of SEQ ID NO: 1-15. In this aspect, the first nucleic acid sequence is preferably included within a vector, which in one embodiment may be a viral vector, such as an AAV vector.

In yet another set of embodiments, the first sequence may comprise the first or the second promoters, which regulate the expression of the second nucleic acid sequence and the third nucleic acid sequence, respectively.

In additional aspect, the invention provides a cell and comprising the first nucleic acid sequence as described above.

In a further aspect, the invention provides a non-human mammal comprising the first nucleic acid sequence as described above. In different embodiments of the invention, the non-human mammal is a mouse or a primate.

In another aspect, the invention provides a method of treating Huntington's disease in a patient comprising administering to said patient: an RNAi agent capable of inhibiting expression of a gene involved in a neurodegenerative disease, said RNAi agent comprising a double-stranded structure having a first strand and a second strand, said first and second strands each being between 19 and 30 nucleotides long, wherein the first strand is encoded by a sequence comprising any one of SEQ ID NO: 1-15; and BDNF or a functional fragment thereof or a nucleic acid sequence encoding BDNF or the functional fragment thereof.

In one embodiment of this method, the RNAi agent is a vectorless molecule, which may optionally comprise a chemical modification that, preferably, reduces alteration of said RNAi agent by endonucleases or exonucleases.

In one embodiment of the method, the nucleic acid sequence encoding said BDNF or said functional fragment thereof is included within a vector. The vector may or may not include the RNAi agent. The vector may be a viral vector such as, for example an AAV vector.

In one embodiment, the RNAi agent and said BDNF or the functional fragment thereof, or a nucleic acid sequence encoding said BDNF or the functional fragment thereof are administered by intracranial injection.

Preferably, the treatment as described above results in improvement of the patient's locomotor activity and/or diminishment of the patient's anxiety.

DETAILED DESCRIPTION OF PREFERRED EMBODIMENTS

Figure 1:
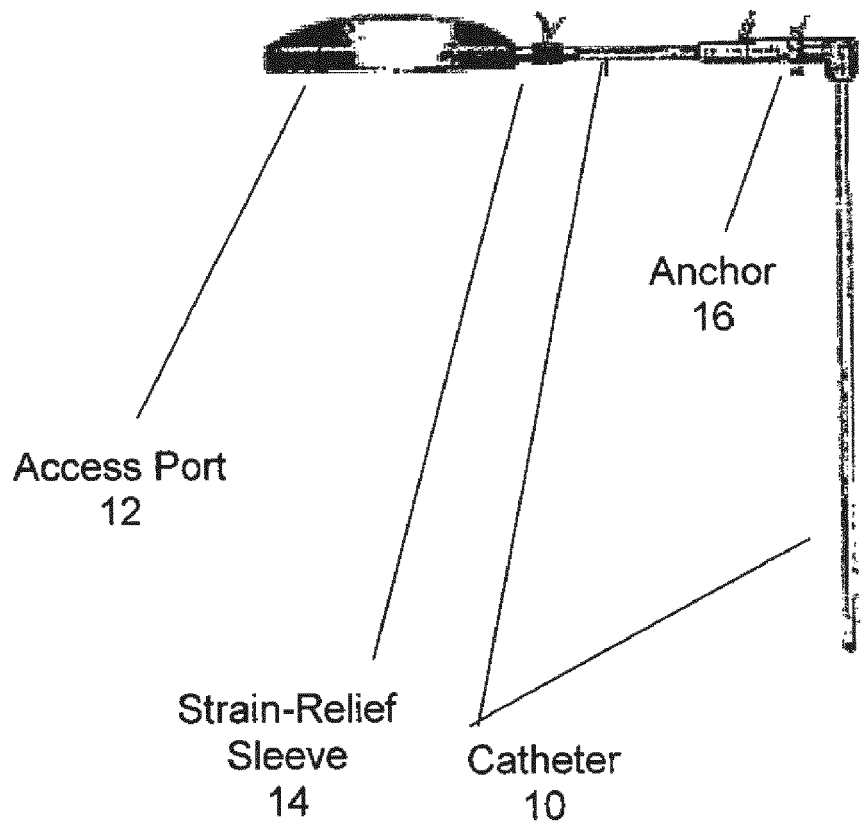
FIG. 1 and FIG. 2 both provide a schematic illustration of the Model 8506 investigational device suitable for different embodiments of the system of the instant invention.

In general, this invention is drawn to novel compositions, methods and systems for treating neurodegenerative disorders which combine RNAi therapy and neurotrophic factor supplementation.

The methods of the present invention utilize routine techniques in the field Of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

DEFINITIONS

In order to better describe the instant invention, the following non-limiting definitions are provided:

The term "RNA interference agent" or "RNAi agent" refers to ribonucleic acid sequences, modified ribonucleic acid sequences, or DNA sequences encoding said ribonucleic acid sequences, which cause RNA interference and thus decrease expression of the target gene. In different embodiments, the RNAi agent includes, without limitations, shRNAs, siRNAs, miRNAs, and DNA-RNA hybrids. In certain embodiments, the RNAi agent may be modified as described in detail below.

The term "small interfering RNA" or "siRNA" refers to a double-stranded RNA molecule wherein each strand is between about 15 and about 30 bases of ribonucleic acid in length, and the two strands have a region of complementarity such that the two strands hybridize or "base pair" together through the annealing of complementary bases (Adenine to Uracil, and Guanine to Cytosine). For some siRNA molecules, the two strands hybridize together in a manner such that there is an overhang of non-annealed bases at the 5' or 3' ends of the strand. For other siRNA molecules, the two strands hybridize together such that each base of one strand is paired with a base of the other strand. For some siRNA molecules, the two strands may not be 100% complementary but may have some bases that do not hybridize due to a mismatch. For some siRNA molecules, the RNA bases may be chemically modified or additional chemical moieties may be conjugated to one or more ends of one or more of the strands.

The term "shRNA" refers to a "short, hairpin" RNA molecule comprised of a single strand of RNA bases that self-hybridizes in a hairpin structure. The RNA molecule is comprised of a stem region of RNA bases that hybridize together to form a double-stranded region, and a loop region of RNA bases that form the bend of the hairpin. The term "shRNA" also refers to a DNA molecule from which a short, hairpin RNA molecule may be transcribed in vitro or in vivo.

The term "functional fragment" of a protein refers to a fragment of that protein which at least partially retains the protein's function of interest. Thus, in different embodiments, the functional fragments of GDNF, BDNF, NGF, IGF-1, and VEGF at least partially retain neuroprotective properties of the respective proteins.

The term "involved in" as applied to genes involved in neurodegenerative diseases refers to genes which are responsible for the neurodegenerative diseases (e.g., IT15 and HD) or involved in a process or cellular pathway that contributes to a neurodegenerative disease process (e.g., BACE1 and AD).

The term "treating" or "treatment" refers to executing a protocol, which may include administering one or more drugs to a patient (human or otherwise), in an effort to alleviate signs or symptoms of a neurodegenerative disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The terms "patient" and "subject" refer to a biological system to which a treatment can be administered. A biological system can include, for, example, an organ, a tissue, or a multi-cellular organism. The terms "patient" and "subject" are used interchangeably throughout this disclosure and include, without limitations, humans.

The term "practitioner" refers to a person or persons who practice the methods and systems of the instant invention on the patient. The term includes, without limitations, doctors, nurses, and scientists.

The term "promoter element" or "promoter" or "regulatory region" refers to a DNA sequence capable of being bound by an RNA polymerase in a cell (e.g., directly or through other promoter-bound proteins or substances) and allowing for the initiation transcription of a coding or non-coding RNA sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The term "promoter" may further optionally include other expression control sequences, including enhancer and repressor sequences.

The term "in operable combination," "in operable order," or "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "penetration enhancer," "cell penetration enhancer," and "cellular uptake enhancer" include single compounds as well as compositions comprising a plurality of compounds, wherein the combination of those compounds improves targeted delivery and/or cellular uptake of, a cargo, such as a neurotrophic factor or an RNAi agent.

Expansions of CAG trinucleotide repeats (CAG repeats) in coding regions of human genes cause numerous disorders by generating proteins with elongated polyglutamine (polyQ) stretches. This group of disorders includes by way of example Dystrophia myotonica, Spinocerebellar ataxia type 1, Spinocerebellar ataxia type 2, Spinocerebellar ataxia type 3, Spinocerebellar ataxia type 6, Spinocerebellar ataxia type 7, Spinocerebellar ataxia type 8, Spinocerebellar ataxia type 17, Huntington disease-like 2, Spinal and bulbar muscular atrophy, Huntington disease, Dentatorubral-pallidoluysian atrophy, Oculopharyngeal dystrophy, Congenital central hypoventilation syndrome, Infantile spasms, Synpolydactyly, Cleidocranial dysplasia, Holoprosencephaly, Hand-foot-genital syndrome, Type II blepharophimosis, ptosis, and epicanthus inversus syndrome. (Wanker E. E. (2000) *Biol. Chem.*, 381:937-942; Gusella J. F. and MacDonald, M. E.

(2000) Nature Rev. Neurosci., 1:109-115; and Usdin K. and Grabczyk, E. (2000) Cell. Mol. Life Sci., 57:914-931).

A further problem of these neurodegenerative diseases is that their prevalence continues to increase, thus creating a serious public health problem.

Recent studies have pointed to alpha-synuclein (Parkinson's disease), beta-amyloid-cleaving enzyme 1 (BACE1 (including variants thereof, e.g. variants A, B, C, and D)) (Alzheimer's disease), huntingtin (Huntington's disease), and ataxin1 (Spinocerebellar Ataxia Type 1) as major factors in the pathogenesis of each of these diseases, respectively.

Additional non-limiting examples of the neurodegenerative diseases are shown in Table 1.

TABLE 1

Triplet Repeat Expansion Disorders

| Disease | Symptoms | Gene | Locus | Protein |
|---|---|---|---|---|
| Non-coding repeats | | | | |
| Dystrophia myotonica 1 | Weakness, Myotonia | DMPK | 19q13 | Dystrophia myotonica Protein kinase |
| Spinocerebellar ataxia 8 | Ataxia | Antisense to KLHL1 | 13q21 | Undetermined |
| Huntington disease-like2 | Chorea, dementia | JPH3 | 16q24.3 | Junctophilin 3 |
| Polyglutamine disorders | | | | |
| Spinal and bulbar muscular atrophy | Weakness | AR | Xq13-q21 | Androgen receptor |
| Huntington disease | Chorea, dementia | IT15 | 4P16.3 | Huntingtin |
| Dentatorubral-pallidoluysian atrophy | Ataxia, myoclonic epilepsy, dementia | DRPLA | 12p13.31 | Atrophin 1 |
| Spinocerebellar ataxia 1 | Ataxia | SCA1 | 6p23 | Ataxin 1 |
| Spinocerebellar ataxia 2 | Ataxia | SCA2 | 12q24.1 | Ataxin 2 |
| Spinocerebellar ataxia 3 | Ataxia | SCA3/MJD | 14q32.1 | Ataxin 3 |
| Spinocerebellar ataxia 6 | Ataxia | CACNA1A | 19p13 | $\alpha_{1A}$-voltage-dependent calcium channel subunit |
| Spinocerebellar ataxia 7 | Ataxia | SCA7 | 3p12-p13 | Ataxin 7 |
| Spinocerebellar ataxia 17 | Ataxia | TBP | 6q27 | TATA box binding protein |
| Polyalanine disorders* | | | | |
| Oculopharyngeal dystrophy | Weakness | PABPN1 | 14q11.2-q13 | Poly(A)-binding protein 2 |
| Congenital central hypoventilation syndrome | Respiratory difficulties | PHOX2B | 4p12 | Paired-like homeobox 2B |
| Infantile spasms | Mental retardation, epilepsy | ARX | Xp22.13 | Aristaless-related homeobox, X-linked |
| Synpolydactyly | Limb malformation | HOXD13 | 2q31-q32 | Homeobox D13 |

*Polyalanine expansions have also been reported among mutations in other genes, including RUNX2 (runt-related transcription factor 2) in cleidocranial dysplasia, ZIC2 (Zic family member 2) in holoprosencephaly HOXA13 (homeobox A13) in hand-foot-genital syndrome, and FOXL2 (forkhead box L2) in type II blepharophimosis, ptosis, and epicanthus inversus syndrome. Small aspartic acid repeat expansions have been reported among other mutations in the COMP (cartilage oligomeric mat4rix protein) gene in patients with multiple epiphyseal dysplasia.

For purposes of illustration only, Huntington's disease (HD) will be discussed herein. The gene responsible for HD contains an expanded and unstable CAG trinucleotide repeat (Huntington's Disease Collaborative Research Group, 1993 Cell 72:971-983). The HD gene (also referred to as "huntingtin gene" or "IT15 gene"), which encodes huntingtin, a 350-kDa protein whose functions have not been fully elucidated, is located on the human chromosome 4 and consists of 67 exons. The disease-causing mutation is a CAG repeat expansion located within exon 1 of the HD gene (HD exon1). The CAG repeat is translated into a polyQ stretch. The disease manifests itself when the polyQ stretch exceeds the critical length of 37 glutamines (pathological threshold), whereas 8-35 glutamine residues in huntingtin are tolerated by neuronal cells. Experimental evidence has been presented that huntingtin fragments with polyQ tracts in the pathological range (more than 37 glutamines) but not in the normal range (20-32 glutamines) form high molecular weight protein aggregates with a fibrillar morphology in vitro and in cell culture model systems (Scherzinger et al. (1999) Proc. Natl Acad. Sci. USA, 96:4604-4609; and Waelter et al., (2001) Mol. Biol. Cell, 12:1393-1407). In addition, inclusions with aggregated N-terminally truncated huntingtin protein were detected in HD transgenic mice carrying a CAG repeat expansion of 115-156 units and in HD patient brains (Davies et al., (1997) Cell, 9.0:537-548; and DiFiglia et al., (1997) Science, 277:1990-1993), suggesting that the process of aggregate formation may be important for the progression of HD. However, the mechanisms by which the elongated polyQ sequences in huntingtin cause dysfunction and neurodegeneration are not yet understood (Scherzinger et al., (1999); Tobin A. J. and Signer, E. R. (2000) Trends Cell Biol., 10:531-536; and Perutz M. F. (1999) Glutamine repeats and neurodegenerative diseases: molecular aspects. Trends Biochem. Sci., 24:58-63).

It is known that patients are able to survive and live healthy lives with only one functioning copy of the IT15 gene. Moreover, patients with expanded CAG repeats are born with no apparent defects while huntingtin-null mice exhibit embryonic lethality. These and other data suggest that huntingtin is neuroprotective in brain cells exposed to various apoptotic stimuli. Cattaneo et al., Nature. Reviews 6: 919-930 (2005).

Additional data link huntingtin to brain-derived neurotrophic factor (BDNF), which is especially important for the survival of striatal neurons. Id. It has been shown that wildtype huntingtin but not huntingtin with expanded number of glutamine repeats increases transcription of BDNF gene.

In addition to regulating transcription of the BDNF gene, it was found that wildtype huntingtin increases but mutant huntingtin represses axonal transport of BDNF. Id. Thus, one mechanism of Huntington's disease progression is due to decreased transcription and trafficking of BDNF.

Previous studies report that gene delivery of BDNF or GDNF (glial cell derived neurotrophic factor) is neuroprotective in a model of quinolinic acid model of Huntington's disease. Kells et al., Mol. Ther. 9(5): 682-688 (2004). However, the treatment with neurotrophic factor (e.g., BDNF) gene delivery may not be efficient since the mutant huntingtin would inhibit expression and appropriate trafficking of BDNF. In addition, mutant huntingtin has been shown to down-regulate expression of the receptor for BDNF, TrkB (Gines et al., 2006 European J Neurosci 23:649-658).

Thus, the inventors propose a therapy for Huntington's disease which comprises a treatment with a combination of RNAi agent and neurotrophic factor and systems, methods, and compositions associated therewith.

The compositions, methods, and systems of the invention according to any embodiment of any of the aspects of the invention may be used whether the RNAi agent is allele-specific or not allele-specific (i.e., whether it selectively reduces expression of a specific allele of the gene causing the neurodegenerative disease). However, since patients with only one functioning copy of the IT15 gene can live healthy lives, it appears that one functioning copy of the IT15 gene is sufficient to maintain a level and appropriate trafficking of BDNF which is effective for neuroprotection. Accordingly, in one embodiment, the RNAi agent is not allele-specific. However, the invention does not exclude the use of the methods, compositions, and systems for treatment of the neurodegenerative diseases, wherein the RNAi agent is allele-specific.

In one aspect, the invention provides a first nucleic acid sequence comprising: a second nucleic acid sequence encoding a neurotrophic factor or a functional fragment thereof; and a third nucleic acid sequence encoding an RNAi agent capable of inhibiting expression of a gene involved in a neurodegenerative disease.

The second nucleic acid sequence comprises in one embodiment a cDNA encoding a neurotrophic factor or a functional fragment thereof. Among suitable neurotrophic factors are, without limitations, BDNF, GDNF, NGF, VEGF, and IGF-1.

As mentioned above, the first nucleic acid sequence further includes a third nucleic acid sequence which comprises an RNAi agent capable of inhibiting expression of a gene responsible for a neurodegenerative disease. In preferred embodiments, the RNAi agents comprise sequences which are a sufficient length and/or stably interact with their complementary substrate sequences. In this and other embodiments of the invention, a wide variety of genes may be selected for preparing the RNAi agent for the third nucleic acid sequence. The suitable examples include, without limitation, IT15, DRPLA, SCA1, SCA2, SCA3/MJD, CACNA1A, SCAT, TBP, PABPN1, PHOX2B, ARX, HOXD13, BACE1, SOD-1, and APP.

In one embodiment, the gene involved in the neurodegenerative disease is the IT15 gene and the RNAi agent comprises a sequence selected from the sequences shown in Table 2.

TABLE 2

Non-limiting examples of sequences suitable for RNAi agents which can be used for IT15, BACE1, α-synuclein, or SOD1 inhibition.

| SEQ ID NO | Target Gene | siRNA Sequence | Accession # | Position within Accession # |
|---|---|---|---|---|
| 1 | IT15 | TGACAGCAGTGTTGATAAA | NM_002111 | 2071-2089 |
| 2 | IT15 | AAGAACGAGTGCTCAATAA | NM_002111 | 2862-2880 |
| 3 | IT15 | TTTATGAACTGACGTTACA | NM_002111 | 1221-1239 |
| 4 | IT15 | GGAGTATTGTGGAACTTAT | NM_002111 | 1404-1422 |
| 5 | IT15 | GAGTATTGTGGAACTTATA | NM_002111 | 1405-1423 |
| 6 | IT15 | AGACCGTGTGAATCATTGT | NM_002111 | 442-460 |
| 7 | IT15 | GGTTACAGCTCGAGCTCTA | NM_002111 | 645-663 |
| 8 | IT15 | GGTTTTGTTAAAGGCCTTC | NM_002111 | 898-916 |
| 9 | IT15 | TGACAGCAGTGTTGATAAATTTGTGTT | NM_002111 | 2071-2097 |
| 10 | IT15 | AAGAACGAGTGCTCAATAATGTTGTCA | NM_002111 | 2862-2888 |
| 11 | IT15 | TTTATGAACTGACGTTACATCATACAC | NM_002111 | 1221-1247 |
| 12 | IT15 | GGAGTATTGTGGAACTTATAGCTGGAG | NM_002111 | 1404-1430 |
| 13 | IT15 | GAGTATTGTGGAACTTATAGCTGGAGG | NM_002111 | 1405-1431 |
| 14 | IT15 | AGACCGTGTGAATCATTGTCTGACAAT | NM_002111 | 442-468 |
| 15 | IT15 | GGTTTTGTTAAAGGCCTTCATAGCGAA | NM_002111 | 898-924 |
| 42 | BACE1 | AAGGGTGTGTATGTGCCCTAC | NM_012104 | 837-857 |
| 43 | BACE1 | AATTGGCTTTGCTGTCAGCGC | NM_012104 | 1697-1717 |
| 44 | BACE1 | AAGACTGTGGCTACAACATTC | NM_012104 | 1783-1803 |
| 45 | BACE1 | AAGGCTGCCTGGAGAAAGGAT | NM_012104 | 3308-3328 |
| 46 | BACE1 | CACTGAATCGGACAAGTTCTT | NM_012104 | 950-970 |
| 47 | BACE1 | CATGATCATTGGTGGTATCGA | NM_012104 | 1163-1183 |
| 48 | BACE1 | CATCCTTCCTCAGCAATACCT | NM_012104 | 1541-1561 |
| 49 | BACE1 | CAGACGCTCAACATCCTGGTG | NM_012104 | 717-737 |

TABLE 2-continued

Non-limiting examples of sequences suitable for RNAi agents which can be used for IT15, BACE1, α-synuclein, or SOD1 inhibition.

| SEQ ID NO: | Target Gene | siRNA Sequence | Accession # | Position within Accession # |
|---|---|---|---|---|
| 50 | α-synuclein | CTACGAACCTGAAGCCTAA | NM_007308 | 334-352 |
| 51 | α-synuclein | TCAAGACTACGAACCTGAA | NM_007308 | 811-829 |
| 52 | α-synuclein | CATTAGCCATGGATGTATT | NM_007308 | 6-24 |
| 53 | α-synuclein | ACGAACCTGAAGCCTAAGA | NM_007308 | 336-354 |
| 54 | α-synuclein | GTACAAGTGCTCAGTTCCA | NM_007308 | 405-423 |
| 55 | α-synuclein | GCTTCAATCTACGATGTTA | NM_007308 | 589-607 |
| 56 | α-synuclein | CTAAGTGACTACCACTTAT | NM_007308 | 625-643 |
| 57 | α-synuclein | GTTCAGAAGTTGTTAGTGA | NM_007308 | 676-694 |
| 58 | α-synuclein | AGTTGTTAGTGATTTGCTA | NM_007308 | 683-701 |
| 59 | α-synuclein | GACGTATTGTGAAATTTGT | NM_007308 | 755-773 |
| 60 | SOD1 | TCATCAATTTCGAGCAGAA | NM_000454 | 201-219 |
| 61 | SOD1 | TGAGTTTGGAGATAATACA | NM_000454 | 295-313 |
| 62 | SOD1 | TGGCCGATGTGTCTATTGA | NM_000454 | 432-450 |
| 63 | SOD1 | CGATGTGTCTATTGAAGAT | NM_000454 | 436-454 |
| 64 | SOD1 | GCATTAAAGGACTGACTGA | NM_000454 | 252-270 |
| 65 | SOD1 | TCGTTTGGCTTGTGGTGTA | NM_000454 | 577-595 |
| 66 | SOD1 | AATTTCGAGCAGAAGGAAAGT | NM_000454 | 206-226 |
| 67 | SOD1 | AAGCATTAAAGGACTGACTGA | NM_000454 | 250-270 |
| 68 | SOD1 | AATGTGACTGCTGACAAAGAT | NM_000454 | 407-427 |
| 69 | SOD1 | AAGATTCTGTGATCTCACTCT | NM_000454 | 450-470 |

In another embodiment, the gene involved in the neurodegenerative disease is the BACE1 gene. In another embodiment, the gene involved in the neurodegenerative disease is the alpha-synuclein gene. In yet another embodiment, the gene involved in the neurodegenerative disease is SOD1 gene. RNAi agents for these genes are particularly preferred for combinations with NGF, GDNF, and IGF-1 or VEGF, respectively, but other combinations are also possible, such as an RNAi agent capable of inhibiting expression of the IT15 gene and GDNF.

A person of the ordinary skill in the art will appreciate that the invention is not limited to the RNAi agents comprising any one of SEQ. IDs NO. 1-15 and that other RNAi agents are also suitable for the compositions, systems, and methods of the instant invention.

In one embodiment, the RNAi agent is in a form of an siRNA molecule. The siRNA molecules targeted to desired sequence can be designed based on criteria well known in the art (see e.g., Elbashir et al., EMBO J. 20:6877 (2001)). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; the siRNA molecule preferably should comprise two nucleotide overhangs (preferably TT) at each 3' terminus; the target segment preferably should be in the ORF region of the target mRNA and preferably should be at least 75 bp after the initiation ATG and at least 75 bp before the stop codon; and the target segment preferably should not contain more than 16-17 contiguous base pairs of homology to other coding sequences. The length of one strand of siRNA should be between 16 and 30 bases. Thus in different embodiment, the length of one strand of siRNA is 17, 18, 19, 20, 21, 22, 23, 24, 25, 26, 27, 28, or 29 nucleotides long.

Based on some or all of these criteria, siRNA molecules targeted to desired sequences can be designed by one of skill in the art using the aforementioned criteria or other known criteria (e.g., Gilmore et al., *J. Drug Targeting* 12:315 (2004); Reynolds et al., *Nature Biotechnol.* 22:326 (2004); Ui-Tei et al., *Nucleic Acids Res.* 32:936 (2004)). Such criteria are available in various web-based program formats useful for designing and optimizing siRNA molecules (e.g., siDESIGN Center at Dharmacon; BLOCK-iT RNAi Designer at Invitrogen; siRNA Selector at Wistar Insitute; siRNA Selection Program at Whitehead Institute; siRNA Design at Integrated DNA Technologies; siRNA Target Finder at Ambion; and siRNA Target Finder at Genscript).

Short hairpin RNA (shRNA) molecules fold back on themselves to produce the requisite double-stranded portion (Yu et al., *Proc. Natl. Acad. Sci. USA* 99:6047 (2002)). Such single-stranded RNA molecules can be produced using DNA templates (e.g., Yu et al., *Proc. Natl. Acad. Sci. USA* 99:6047 (2002)). In view of the length criteria for the siRNA, the length of the shRNA should be adjusted accordingly.

It is not necessary that the second and the third nucleic acid sequences be joined immediately adjacent each other. In different embodiments of the invention, spacers may be used between the second and the third nucleic acid sequences. The spacers may be as short as 1 nucleotide, as long as 3,000 nucleotides, or any length between these two numbers. In one embodiment, the second and the third nucleic acid sequences are separated by 200 to 1000 nucleotides.

Further, the order of the second and the third sequences is not important. Thus, in one set of the embodiments, the second nucleic acid sequence is upstream of the third nucleic acid sequence. In another set of embodiments, the second nucleic acid sequence is downstream of the third nucleic acid sequence.

A person of the ordinary skill in the art will appreciate that in any of the embodiments disclosed above or below, the first nucleic acid sequence may further optionally comprise one or more promoters. For example, the first nucleic acid sequence may include a first promoter which is operably linked to the second nucleic acid sequence. In another embodiment, the first nucleic acid sequence may also comprise a second promoter which is operably linked to the third nucleic acid sequence. It would be understood by a person of the ordinary skill in the art that the first nucleic acid sequence may comprise only the first promoter, or only the second promoter, or both the first and the second promoters in different embodiments of the invention.

Suitable examples of the first and the second promoters may independently include promoters which may be constitutively active or tissue-specific. Promoters for eukaryotic RNA polymerase I (pol I), RNA polymerase II (pol II), or RNA polymerase III (pol III) may be used to direct transcription of the second and third nucleic acid sequences as is known and appreciated in the art. Several investigators have demonstrated that RNA molecules can be expressed from such promoters can function in mammalian cells (e.g. Kashani-Sabet et al., 1992, Antisense Res. Dev., 2, 3-15; Ojwang et al., 1992, Proc. NatL Acad Sci. USA, 89, 10802-6; Chen et al., 1992, Nucleic Acids Res., 20, 4581-9; Yu et al., 1993, Proc. Natl. Acad Sci. USA, 90, 6340-4; L'Huillier et al., 1992, EMBO J, 11, 4411-8; Lisziewicz et al., 1993, Proc. Natl. Acad. Sci. U.S.A, 90, 8000-4; Thompson et al., 1995, Nucleic Acids Res., 23, 2259; Sullenger & Cech, 1993, Science, 262, 1566). In one embodiment, the suitable promoters include constitutive RNA polymerase II promoters (e.g., cytomegalovirus (CMV) promoter, the SV40 early promoter region, the promoter contained in the 3' long terminal repeat of Rous sarcoma virus (RSV), the herpes thymidine kinase (TK) promoter, and the chicken beta-actin promoter), cardiac-tissue-specific RNA polymerase II promoters (e.g., the ventricular myosin light chain 2 (MLC-2v) promoter, and the sodium-calcium exchanger gene H1 promoter (NCX1H1)), and RNA polymerase III promoters (e.g., U6, H1, 7SK and 7SL). A non-limiting example of a tissue-specific promoter is neuron-specific enolase promoter. It has been shown that 1.8 kb rat neuron-specific enolase promoter in combination with woodchuck posttranscriptional regulatory element is sufficient for expression of gene-delivered BDNF in rat brain. Kells et al., 2005).

In another embodiment, transcription units may be used. More specifically, transcription units such as the ones derived from genes encoding U6 small nuclear (snRNA), transfer RNA (tRNA), and adenovirus VA RNA are useful in generating high concentrations of desired RNA molecules such as small interfering RNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman at al., International PCT Publication No. WO 96118736; all of these publications are incorporated by reference herein). The above small interfering RNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

The first nucleic acid sequence may further comprise additional functional sequences, such as an internal ribosomal entry site (IRES) and sequences that terminate transcription.

The first nucleic acid sequence according to any of the embodiments of the instant aspect of the invention may be delivered as a naked sequence or, preferably, included within a vector, which may be either a plasmid vector or a viral vector. It is also possible that non-viral vectors, such as plasmid DNA delivered alone or complexed with liposomal compounds or polyethyleneamine, may be used to deliver the first nucleic acid sequence to neurons in the brain.

Although numerous expression vectors can be used to express siRNA molecules and the neurotrophic factor molecules in cells (Dorsett and Tuschl, *Nat. Rev. Drug Discov.* 3:318 (2004)), viral expression vectors are preferred, particularly those that efficiently transduce brain cells (e.g., alphaviral, lentiviral, retroviral, adenoviral, adeno-associated viral (AAV)) (Williams and Koch, *Annu. Rev. Physiol.* 66:49 (2004); del Monte and Hajjar, *J. Physiol.* 546.1:49 (2003). Both adenoviral and AAV vectors have been shown to be effective at delivering transgenes (including transgenes directed to diseases) into brain. See, e.g., Kells (2005), Machida et al., *Biochem. Biophys. Res. Commun.*, 343(1): 190-7 (2006).

The method of constructing the first nucleic acid sequence and the appropriate vector constructs are well known in the art. These methods include, without limitation, any combinations of PCR and/or RT-PCR, endonuclease restriction, ligation, and subcloning. Further, mRNA, cDNA, and, if needed, amino acid sequences of any and all full molecules (e.g., IT15 gene (SEQ. ID. NO. 16), BACE1 gene (SEQ. ID. NOs. 17-20 for transcript variants A, B, C, and D, respectively), alpha synuclein gene (SEQ. ID. NOs. 21 and 22 for transcript variants NACP140 and NACP112, respectively), SOD-1 gene (SEQ. ID. NO. 23), BDNF (SEQ. ID. NOs. 24-29 for transcript variants 1-6, respectively), GDNF (SEQ. ID. NOs. 30-32 for transcript variants 1-3, respectively), NGF (SEQ. ID. NO. 33), IGF-1 (SEQ. ID. NO. 34), VEGF (SEQ. ID. NOs. 35-41 for transcript variants 1-7, respectively), etc.) are well known in the art and available from GenBank. Exemplary sequences are also provided in the "Sequence Listing" section accompanying the instant disclosure.

Shorter nucleic acid sequences, e.g., the third nucleic acid sequence may be produced by multiple methods. There are currently five methods for producing siRNA: chemical synthesis, in vitro transcription, preparation of siRNA population by digestion, in vivo expression of hairpin siRNA from an expression vector, and in vivo expression of siRNA from a PCR-derived expression cassette. All these methods may be used for the instant invention.

Examples of additional sequences suitable for the RNAi agents are shown in Table 2 above. SEQ. ID. NOs. 42, 43, 44, 45, 46, 47, 48, and 49 relate to suppressing BACE1 mRNA;

SEQ. ID. NOs. 50, 51, 52, 53, 54, 55, 56, 57, 58 and 59 relate to suppressing α-synuclein mRNA; and SEQ. ID NOs. 60, 61, 62, 63, 64, 65, 66, 67, 68, and 69 relate to suppressing SOD1 mRNA.

Accordingly, a person of the ordinary skill in the art will not be burdened with undue experimentation while producing nucleic acid sequences and proteins or fragments thereof which are claimed or disclosed in the instant invention.

When the appropriate constructs are prepared (including, without limitation, vectors containing the first nucleic acid sequence, vectors containing only RNAi agent, or vectors containing nucleic acid sequence of the neurotrophic factor or the functional fragment thereof), these components can be produced at a large scale.

For example, the vectors containing the RNAi agent (including the vectors containing the first nucleic acid sequence) can be produced in large quantities by using packaging cell strains such as those described in J. M. Coffin, S. H. Hughes & H. E. Varmus (eds.), Retroviruses, Cold Spring Harbor Laboratory Press. Other methods for producing retroviruses and for infecting cells in vitro or in vivo are described in Current Protocols in Molecular Biology, Ausubel, F. M. et al. (eds.) Greene Publishing Associates, (1989), Sections 9.10-9.14.

Further, if it is a protein which is used for the therapy according to any of the methods of the instant invention (e.g., for using the neurotrophic factor or the functional fragment thereof in a form of protein), expression systems may be used. In that method, the vector containing the nucleic acid sequence encoding the protein of interest or the functional fragment thereof is later introduced to host cells. The choice of the host cell system depends largely on the type of the vector and the type of the promoter. In general, the host cells include, without limitations, prokaryotic, yeast, insect, and mammal cells.

Further, depending on the type of the host cell, the codons of the nucleic acid sequences encoding the amino acid sequences of the instant invention can be selected for optimal expression in prokaryotic or eukaryotic systems. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); and insect cell systems infected with virus (e.g., baculovirus). The expression elements of these vectors vary in their strength and specificities. Depending upon the host-vector system utilized, any one of a number of suitable transcription and translation elements can be used.

In another set of embodiments, the invention provides a variety of formulations which can be used in combination with the compositions, methods and systems of the instant invention as described both above and below.

For example, in one embodiment of the present invention, the composition comprising the RNAi agent or precursors or derivatives thereof is formulated in accordance with standard procedure as a pharmaceutical formulation adapted for delivered administration to human beings and other mammals. Typically, formulations for intravenous administration are solutions in sterile isotonic aqueous buffer.

Where necessary, the formulation may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the formulation is to be administered by infusion, it can be dispensed with an infusion bottle containing sterile pharmaceutical grade water or saline. Where the formulation is administered by injection, an ampule of sterile water for injection or saline can be provided so that the ingredients may be mixed prior to administration.

In cases other than intravenous administration, the formulation can contain minor amounts of wetting or emulsifying agents or pH-buffering agents. The formulation can be a liquid solution, suspension, emulsion, gel, polymer, or sustained-release formulation. The formulation can further include traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules, and the like. Thus, in one embodiment, the RNAi agents of the invention are added directly, or can be complexed with cationic lipids, packaged within liposomes, packaged within viral vectors, or otherwise delivered to target cells or tissues.

In a second aspect, the invention provides a method of treating a patient affected with a neurodegenerative disease comprising: administering to said patient an RNAi agent capable of inhibiting expression of a gene responsible for a neurodegenerative disease and at least one of a neurotrophic factor or a functional fragment thereof.

According to different embodiments of this aspect of the invention, the RNAi agent, including RNAi agents comprising any one of SEQ. ID. NOs. 1-15 and 42-69, may be delivered within a vector or as a vectorless, or naked, nucleic acid, including DNA-RNA hybrids. If the RNAi agent is administered in a naked form, it may be chemically modified (e.g., the RNAi agent may include one or more modified nucleotides) for improving its stability and increasing its penetration into the neurons. The RNAi agent suitable for this aspect of the invention can comprise modified nucleotides at various locations, whether in base-paired position or non-base-paired position, including the loop, if the RNAi agent is an shRNA, or the overhang positions. The modified nucleotides may be located either on the sense or the antisense part of the RNAi agent.

For example, in one embodiment, the pyrimidine nucleotides in the sense region of the RNAi agent are 2'-O-methylpyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides.

Additional non-limiting examples of chemical modification of the nucleotides in the RNAi agent include 2'-O-trifluoromethyl nucleotides, 2'-O-ethyl-trifluoromethoxy nucleotides, or 2'-O-difluoromethoxy-ethoxy nucleotides. The RNAi agent can also comprise at least one modified internucleotidic linkage, such as a phosphorothioate linkage. In one embodiment, the 2'-deoxy-2'-fluoronucleotides are present at specifically selected locations in the RNAi agent that are sensitive to cleavage by ribonucleases, such as locations having pyrimidine nucleotides.

In a further set of embodiments, the RNAi agent may be chemically modified on a 3' end, a 5' end, or both the 3' end and the 5' end. These terminal modifications protect the nucleic acid molecule from exonuclease degradation and may help in delivery and/or localization within a cell. Examples of moieties suitable for the modification of the 5' end of the RNAi agent include, without limitations, glyceryl, inverted deoxy abasic residue (moiety); 4',5'-methylene nucleotide; 1-(beta-D-erythrofuranosyl)nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the moieties suitable for modification of the 3'-end of the RNAi agent include glyceryl, inverted deoxy abasic residue (moiety), 4',5'-methylene nucleotide; 1-(beta-D-erythrofuranosyl)nucleotide; 4'-thio nucleotide, carbocyclic nucleotide; 5'-amino-alkyl phosphate; 1,3-diamino-2-propyl phosphate; 3-aminopropyl phosphate; 6-aminohexyl, phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties.

Yet additional suitable modifications of the RNAi agent are described in details in U.S. patent application Ser. No. 11/450,856, filed on Jun. 9, 2006 (McSwiggen), which is incorporated herein by reference to the extent it is not inconsistent with the instant disclosure.

The RNAi agent, whether in the naked form or included within the first nucleic acid sequence according to any embodiment of the first aspect of the invention, may be delivered by intravenous, intranasal, intraocular, intraperitoneal, intracranial, or intrathecal injection. Preferably, the RNAi agent is in a formulation, which is preferably composed according to any of the embodiments described above.

The neurotrophic factor or the functional fragment thereof may be delivered to the patient in the form of another nucleic acid construct (e.g., another vector, using plasmid and viral vectors suitable for the first nucleic acid, as described above) or in the form of a protein. In a preferred embodiment, the neurotrophic factor or the fragment thereof is delivered in the form of protein. Again, the protein may be in the form of a formulation, which is preferably composed according to any of the embodiments described above.

Thus, at least four combinations are possible in this aspect of the invention. These combinations include: (a) delivery of the RNAi agent within a vector and delivery of the neurotrophic factor or a functional fragment thereof within the same or a different vector; (b) delivery of the RNAi agent within a vector and delivery of the neurotrophic factor or a functional fragment thereof in a form of protein; (c) delivery of the RNAi agent (whether chemically modified or unmodified) in a vectorless form and delivery of the neurotrophic factor or a functional fragment thereof within a vector; and (d) delivery of the RNAi agent (whether chemically modified or unmodified) in a vectorless form and delivery of the neurotrophic factor or a functional fragment thereof in a form of protein.

A person of the ordinary skill in the art will appreciate that the neurotrophic factor or the functional fragment thereof and the RNAi agent may be delivered to the patient simultaneously or independently of each other, by the same or by a different delivery route.

The third aspect of the invention provides a method of treating a patient with a neurodegenerative disease comprising: administering to said patient a first nucleic acid sequence of any one of the embodiments of the first aspect, as disclosed above.

In general, the amount of the therapeutic agent(s) according to any embodiment of the methods the present invention which will be effective in the treatment of a particular disorder will depend on the nature of the disorder, and can be determined by standard clinical techniques, well established in the administration of therapeutics. The precise dose to be employed in the formulation will also depend on the route of administration, and the seriousness of the disease, and should be decided according to the judgment of the practitioner and the patient's needs.

In a set of embodiments, where the RNAi agent is included within a viral vector (including the vectors comprising the first nucleic acid sequence), suitable dose ranges for intracranial administration are generally about $10^3$ to $10^{15}$ infectious units of viral vector per microliter delivered in 1 to 3000 microliters of single injection volume. Additional amounts of infectious units of vector per micro liter would generally contain about $10^4$, $10^5$, $10^6$, $10^7$, $10^8$, $10^9$, $10^{10}$, $10^{11}$, $10^{12}$, $10^{13}$, $10^{14}$ infectious units of viral vector delivered in about 10, 50, 100, 200, 500, 1000, or 2000 microliters. Effective doses may be extrapolated from dose-responsive curves derived from in vitro or in vivo test systems.

The practitioner may also chemically modify the neurotrophic factors in the form of protein. Such modifications may be helpful for such properties as the ability of the therapy (either in the form of nucleic acid sequence or in the form of protein) to get through the blood-brain barrier (BBB) or to get through the cell membrane.

A suitable non-limiting example of a penetration enhancer is polyethylene glycol, or PEG. A receptor-specific monoclonal antibody (mAb) directed at a BBB receptor, such as the insulin receptor or transferrin receptor (TfR), may be attached to PEG strands and thus transport PEG through the BBB.

Similarly to the nucleic acid sequences, the proteins of the instant invention (e.g., the neurotrophic factor or the fragment thereof, including, without limitation, BDNF, GDNF, NGF, IGF-1, and VEGF) may be delivered as a formulation according to the guidelines known in the art. Exemplary components of suitable formulations have been described in connection with the nucleic acid sequence formulations. The same components would be suitable for the protein formulations.

A person of the ordinary skill in the art will understand and appreciate that the methods of the second and the third aspect of the invention may be combined: thus the patient will receive the neurotrophic factor or the functional fragment thereof in the form of a protein, the RNAi agent (either in a naked form or in a vector), and a vector comprising the first nucleic acid sequence. Any combination of these two compounds may be delivered simultaneously, or these compounds may be delivered at different times. A person of the ordinary skill in the art will also appreciate that these compounds may be delivered by different routes which may be independently selected from intracranial, intravenous, intranasal, intraocular, and intrathecal delivery routes. In one embodiment, the RNAi agents or combinations of the RNAi agents and neurotrophic factors can be locally administered to relevant tissues ex vivo, or in vivo through injection, infusion pump or stent, with or without their incorporation in biopolymers.

In a fourth aspect, the invention provides a system which is suitable for practicing the methods according to the second and the third aspects of the invention, where at least one compound is delivered intracranially. Generally, the system comprises: a) a means for mapping the location of a neuron within the brain of the live patient; b) an intracranial access device providing fluid access to the neuron; and c) the therapy.

A person of the ordinary skill in the art will appreciate that in one set of embodiments, the therapy comprises the first nucleic acid sequence according to any of the embodiments described above. In another set of embodiments, the therapy comprises the RNAi agent and/or the neurotrophic factor.

A person of the ordinary skill in the art will further appreciate that multiple stents or catheters, preferably catheters having access ports, can be implanted in a given patient for a complete therapy. In a preferred embodiment, there is at least one port and catheter system per cerebral or cerebellar hemisphere and perhaps several. Once the implantations are performed by a practitioner, the practitioner (who may be the same or different from the practitioner who implanted the catheters) can perform a course of therapy according to the methods described in the second and the third aspects of the invention over a period of weeks to months, along with monitoring for therapeutic effect over time. The devices can remain implanted for several months or years for a full course of therapy. After confirmation of therapeutic efficacy, the access ports might optionally be explanted, and the catheters can be sealed and abandoned or explanted as well. The device material should not interfere with magnetic resonance imaging, and, of course, the access port and catheter materials and any surface coatings must be compatible with the compounds which are delivered through these devices, including, in different embodiments, the nucleic acid sequences, including the naked RNAi agent, the vector comprising the RNA agent, and/or the proteins including the neurotrophic factors or the functional fragments thereof.

In one preferred embodiment, the delivery is through the use of implanted, indwelling, intraparenchymal catheters that provide a means for directly injecting small volumes of fluid containing AAV or other vectors into local brain tissue. The proximal end of these catheters may be connected to an implanted, intracerebral access port surgically affixed to the patient's cranium or to an implanted drug pump located in the patient's torso.

Figure 2:
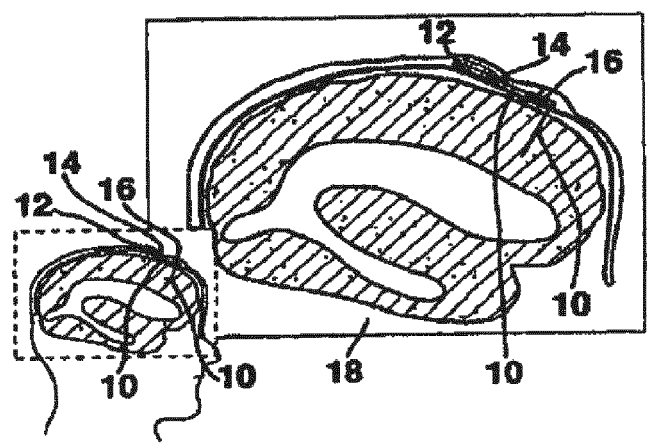

Examples of the delivery devices within the scope of the present invention include the Model 8506 investigational device (by Medtronic, Inc. of Minneapolis, Minn.), which can be implanted subcutaneously on the cranium and provides an access port through which therapeutic agents may be delivered to the brain. Delivery occurs through a stereotactically implanted polyurethane catheter. The Model 8506 is schematically depicted in FIGS. 1 and 2. Two models of catheters that can function with the Model 8506 access port include the Model 8770 ventricular catheter by Medtronic, Inc., for delivery to the intracerebral ventricles, which is disclosed in U.S. Pat. No. 6,093,180, incorporated herein by reference, and the IPA1 catheter by Medtronic, Inc., for delivery to the brain tissue itself (i.e., intraparenchymal delivery), disclosed in U.S. Ser. Nos. 09/540,444 and 09/625,751, which are incorporated herein by reference. The latter catheter has multiple outlets on its distal end to deliver the therapeutic agent to multiple sites along the catheter path.

In addition to the aforementioned device, the delivery of the components of the therapies described above (including, without limitations, the RNAi agent, the first nucleic acid sequence, whether naked or within the vector, the neurotrophic factor or the functional fragment thereof) according to the embodiments described previously in accordance with the present invention can be accomplished with a wide variety of devices, including but not limited to U.S. Pat. Nos. 5,735,814, 5,814,014, and 6,042,579, all of which are incorporated herein by reference. Using the teachings of the present invention those of skill in the art will recognize that these and other devices and systems may be suitable for delivery of the therapies according to any of the embodiments of the first, the second, and the third aspects of the invention for the treatment of neurodegenerative diseases in accordance with the present invention.

In an additional set of embodiments suitable for practicing the methods according to any of the embodiments of the instant invention, the system further comprises a pump, which may be worn on a patient's clothing (e.g., on a belt or in a pocket) or implanted outside the brain. The pump is preferably coupled to a proximal end of the catheter, and operating the pump delivers the predetermined dosage of the therapeutic (e.g., the RNAi agent, the first nucleic acid sequence, whether naked or within the vector, the neurotrophic factor) through the discharge portion of the catheter.

In another set of embodiments for delivering the compositions of any of the embodiments disclosed above according to the methods of any embodiment of the invention disclosed above, the intracranial access device is a guide cannula. The cannula is preferably attached to the intracranial access port and preferably sealed on the distal end (the end outside of the patient's skull) or both the distal end and the proximal end. The cannula may be manufactured from a tissue-compatible material (e.g., a material which is not toxic at physiological conditions and degradation of which at physiological conditions does not result in toxic residues), and, in one embodiment, a proximate end of the cannula is formed with tissue-compatible material having antibacterial properties.

When the practitioner desires to administer the treatment, he may insert the catheter into the cannula, as disclosed above, and deliver the therapy, such as a therapy according to any one of the embodiments described above.

In yet another embodiment, the cannula is functionally connected with a syringe, such as a microsyringe, comprising a catheter for insertion into the guide tube; a flow regulator through which the biologic, chemical, or pharmaceutical agent is released at a predetermined rate; a delivery chamber containing a predetermined amount of fluid volume and biologic, chemical, or pharmaceutical agent to be injected into the brain tissue; and a second chamber (separate from the first chamber) containing a septum that acts as a piston or plunger to deliver the material through the catheter. The second chamber may be filled with hydraulic fluid, oil, gas, air, or any other suitable substance capable of providing controlled pressures for releasing the biologic, chemical, or pharmaceutical agent into the brain tissue. A non-limiting example of a suitable microsyringe has been disclosed in a co-pending application, Ser. No. 11/562,282, (Kaemmerer), filed Nov. 21, 2006.

Generally, neurons affected with Huntington's disease reside in striatum, neurons affected with Alzheimer's disease reside in nucleus basalis of Meynart and the cerebral cortex, and neurons affected with Parkinson's disease reside in the substantia nigra. Thus, in different embodiments depending on the disease, the catheter or other intracranial access device delivers the therapies according to the methods of the instant invention to nucleus basalis of Meynart and the cerebral cortex, striatum, and/or the substantia nigra.

The location of a neuron or neurons affected with a neurodegenerative disease (e.g., Huntington's, Alzheimer's, Parkinson's) may be mapped by many methods. For example, for some applications, it can be mapped by stereotactical or gross anatomical atlases. In other embodiments, when the precise location of the targeted area is crucial, other mapping means may be used in addition to stereotactical or gross anatomical atlases. Such mapping means include, without limitation, Positron Emission Tomography and Single Photon Emission Computed Tomography 1PET and SPECT, respectively), pharmacological Magnetic Resonance Imaging (phMRI), functional MRI (fMRI), and contrast-enhanced computerized tomography (CT) scan.

In another embodiment, computer-aided atlas-based functional neurosurgery methodology can be used to accurately and precisely inject the deoxyribonucleic acid of the present invention. Such methodologies permit three-dimensional display and real-time manipulation of cerebral structures. Neurosurgical planning with mutually preregistered multiple brain atlases in all three orthogonal orientations is therefore possible and permits increased accuracy of target definition for treatment injection or implantation, reduced time of the surgical procedure by decreasing the number of tracts, and facilitates planning of more sophisticated trajectories. See, e.g., Nowinski, W. L. et al., Computer-Aided Stereotactic Functional Neurosurgery Enhanced by the Use of the Multiple Brain Atlas Database, IEEE Trans Med Imaging 19(1); 62-69:2000.

Further, in 2001, Medtronic, Inc. introduced a "mapping means" device, termed the Medtronic NT StealthStation® Treon™, into the marketplace. This medical system further refines the computerized technologies of multi-dimensional imaging and navigation to enable neurosurgeons to precisely plan, re-plan, and visualize a procedure as it proceeds deep within the brain for treating neurological disorders in a living human patient.

Certain embodiments of the invention will now be discussed in the following non-limiting prophetic example.

Prophetic Example 1

Overview:

Combined RNAi and neurotrophic factor-based therapies have potential to treat a number of neurodegenerative diseases. This co-therapy can be achieved using a variety of strategies ranging from a single injection of virus encoding both therapeutic agents to life long infusions of the RNAi agent and the neurotrophic factor. Various combinations of acute and chronic methods of nucleic acid and/or protein factor delivery can be utilized.

Description of Transgenic Mice:

A number of transgenic animal models of HD have been developed that express full length or truncated portions of the HD gene containing expanded CAG repeat tracts. Many of these models demonstrate progressive motor deficits and/or neuropathologic alterations of reminiscent of HD (Bates and Gonitel, *Mol. Biotech.* 2006, 32:147, Wang and Qin, *Acta Pharmacologica Sinica.* 2006, 27(10):1287). Evaluation of combined RNAi and neurotrophic factor-based therapies can be performed in models that express mutant forms of the human HD gene as long as the sequences targeted by the siRNA of interest are present in the mutant transgene. For example, the BAC-HD mice developed by William Yang express the full length mutant HD protein (Htt) from the endogenous human Htt locus contained on a bacterial artificial chromosome (BAC) transferred to the mice (Gray et al. *Soc. Neurosci. Conf.* 2007, 765.10). The BAC-HD transgenic animals display many of the phenotypic features seen in adult-onset HD, including progressive and robust motor deficits, late onset hyperactivity, selective neuropathology restricted to the cortex and striatum, and a characteristic pattern of mhtt aggregation.

Experimental Protocol:

Study aim: To determine the behavioral and patho-histological alterations following delivery of an anti-HD RNAi and BDNF combination therapy to the striatum of BAC-HD mice.

A non-limiting example of the experimental design for accessing the effect of the combination treatment of the instant invention is illustrated in Table 3.

TABLE 3

Experimental groups: (n = 12, same sex ratio across treatment groups)

| Mice | Treatment | Comments |
|---|---|---|
| Wildtype FVB | Surgery and PBS injection | Wildtype FVB control |
| BAC-HD (FVB) | Surgery and PBS injection | BAC-HD FVB control |
| BAC-HD (FVB) | AAV-shRNA#5 (SEQ. ID. NO. 4) | Efficacy of anti-HD shRNA |
| BAC-HD (FVB) | AAV-shRNA#1 (SEQ. ID. NO. 1) | Efficacy of anti-HD shRNA |
| BAC-HD (FVB) | AAV-control shRNA | Control for shRNA |
| BAC-HD (FVB) | AAV-BDNF-GFP | Benefit from BDNF only |
| BAC-HD (FVB) | AAV-BDNF-GFP + AAV-shRNA#5 | Combined benefit of BDNF and anti-HD shRNA |

Surgery: The test or control articles are administered by acute bilateral striatal infusion to animals of ~3 month's age. Note: All AAV injections contain viral titers of $10^6$ to $10^9$ viral genomes.

Behavioral Measures: To be conducted at ~2, 5 and 8 months of age. Some or all of the following behavioral tests may be administered
  Rotarod for motor coordination
  Open field for exploratory and locomotor behavior
  Grip strength/stretch test, balanced beam test
  Y maze alternation for memory
These tests are well known in behavioral biology and are within the abilities of persons of ordinary skill in the art.

Body Weight Measures: The body weight of the animals is monitored weekly starting at 2 months of age.

Molecular and Histological Analyses: The molecular and histological analyses are conducted when animals are about 8 months of age (5 months post-surgery).

Some of the experiments are performed on fresh frozen tissue (dissection of striata, cortex, cerebellum): (n=8 per treatment group) by the methods known to those skilled in the art and not limited to the methods disclosed below:
  Forebrain and cerebellar weight (n=8)
  Mutant and endogenous htt, BDNF, and GAPDH mRNA expression (qRT-PCR) (n=4)
  Mutant and endogenous Htt, BDNF, and housekeeping (tubulin or other) protein expression (western immunoblotting) (n=4)
  Additional experiments are performed using 4% paraformaldehyde or alternate-perfuse-fixed tissue: (n=4 per treatment group)
  Stereological striatal volume (NeuN-positive cell counting);

Immunohistochemical staining for neuropil aggregates (EM48), and degenerating neurons (amino cupric silver or toluidine blue);

Viral volume of distribution: fluorescence (GFP) imaging or immunohistochemistry (GFP and BDNF).

Working Example 1

Transgenic Mice Model

The inventors used the BAC transgenic mouse model of HD (BAC-HD) that expresses the full-length human mutant htt, with loxP sites (SEQ ID NO 70: 5'-ctacttcgta tagcatacat tatacgaagt tat-3', SEQ ID NO 71: 5'-ataacttcgt atagcataca ttatacgaag ttat-3') flanking the exon 1 of mutant htt sequence encoding 97 CAG. This BAC transgenic mouse model exhibits progressive behavioral and neuropathological impairments (Gray et al., 2008, J. Neurosci., 28:6182-95).

Working Example 2

Treatments

Two-month-old wildtype (Wt) and transgenic (Tg) BAC-HD mice were stereotaxically injected in groups of 18 (9 males, females) with 5 µl of pre-validated AAV2/1 constructs (expressing Cre) ($10^9$ virus expressing genomes) into the striatum of both hemispheres at a rate of 0.5 µl/min.

CRE delivered in the striatum of BAC-HD mice as a prelude to deciphering the potential therapeutic benefit of RNAi-mediated knockdown of mutant htt in HD. The coordinates for injection were +0.5 mm (anterior-posterior); +1.8 mm (medial-lateral), and −3.6 mm (dorsal-ventral), relative to Bregma.

In addition, the inventors investigated the therapeutic potential of supplementing brain-derived neurotrophic factor (BDNF) protein the striatal reduction of which is also implicated in the pathogenesis of HD. BDNF was administered intrastriatally as a nucleic acid sequence within AAV in the amount of $10^9$ genomes.

Thus, the treatment groups were as follows: Inert (AAV expressing a control sequence); Cre (AAV expressing Cre); Cre+BDNF.

All behaviors were assessed blind, 1 week prior to treatment and intermittently until 12 months of age (ongoing).

All statistical analyses were performed using 2-way repeated measures Anova followed by Tukey's post-hoc test.

Working Example 3

Treatment with Cre Alone and with a Combination of CRE and BDNF Reverses Motor Deficit in Tg BAC-HD Mice Mice were first trained to traverse a circular beam (2.5 cm diameter, 40 cm length) from one end that was lit by a 60 W bulb to another end that terminated into a dark box.

Immediately after completion of training (5 successful trials on the training beam), mice were tested on four beams that presented an increasing challenge to traverse (1.2 cm through 0.3 cm diameter). The number of footslips, total distance traveled, and total time taken to traverse all beams were scored blind; data are represented as mean+SEM values for each group. A fall was scored with cut-off values of 4 for the number of footslips and 20 sec for the time to traverse per beam.

Figure 3:
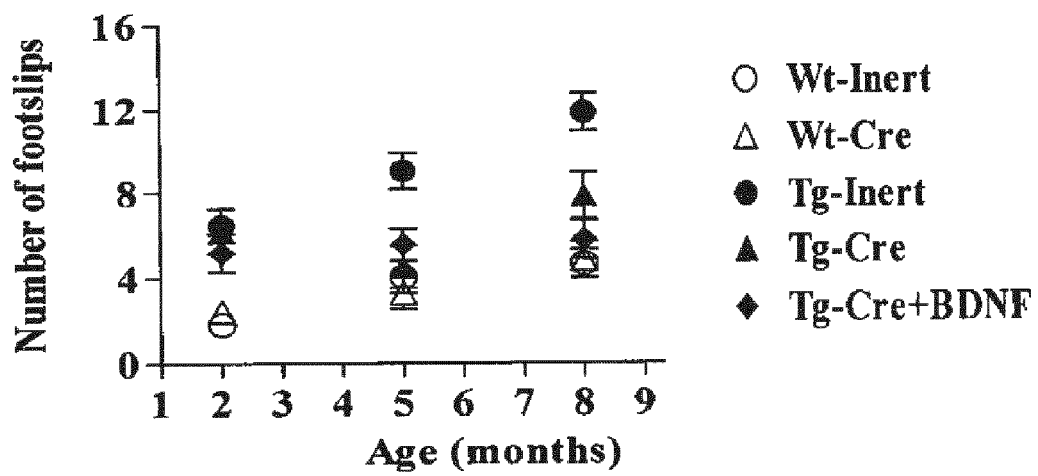
FIG. 3 illustrates improvement in the number footslips committed at five and eight months of age by transgenic (BAC-HD) mice treated at 2 months of age (1 week after behavior testing at 2 months age) with Cre or Cre+BDNF, and trained to traverse a circular beam.

As demonstrated in FIG. 3, control Tg BAC-HD mice exhibited a higher number of footslips compared to wt animals at all three time points (2 months, 5 months, and 8 months). Treatments with Cre or Cre+BDNF significantly reduced the number of footslips in five ($p<0.001$, Tg-Cre vs. Tg-inert; $p<0.05$, Tg-Cre+BDNF vs. Tg-inert) and eight-month old Tg BAC-HD mice ($p<0.01$, Tg-Cre vs. Tg-inert; $p<0.001$, Tg-Cre+BDNF vs. Tg-inert). When compared to the wt mice, the number of footslips in five and eight month-old Tg BAC-HD mice treated with Cre or Cre+BDNF was not significantly different from that of the control wt mice or wt mice treated with Cre (Tg-Cre or Cre+BDNF vs. Wt. Cre or inert; all non-significant at 5 or 8 month time point).

Figure 4:
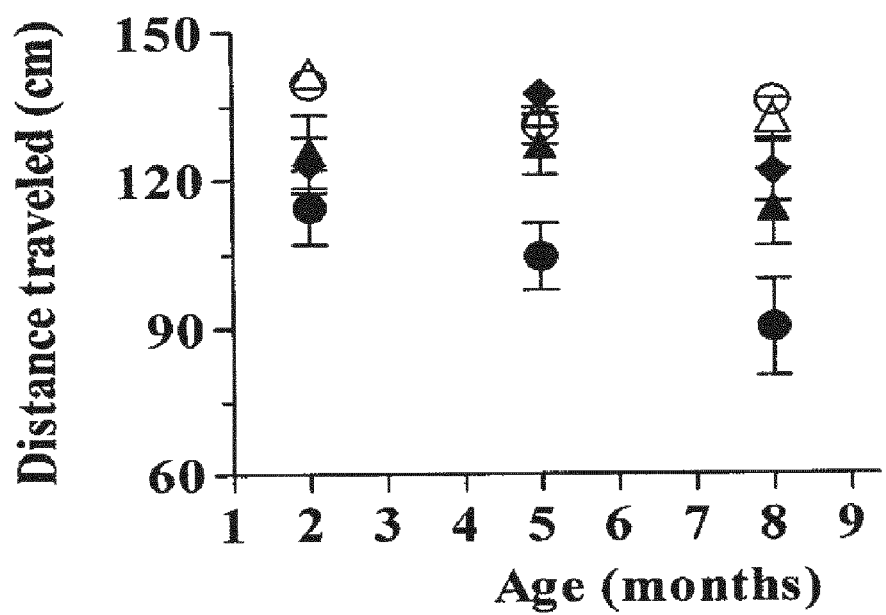
FIG. 4 illustrates the increase of distance traveled at five and eight months of age by transgenic (Tg BAC-HD) mice treated with Cre or Cre+BDNF at 2 months of age, and trained to traverse a circular beam.

The distance traveled by the animals in this experimental set-up is summarized in FIG. 4. Control Tg BAC-HD mice traveled a shorter distance than the wt animals, and the difference between the Tg BAC-HD and wt mice increased at five and eight months. Treatments with Cre or Cre+BDNF significantly increased the distance traveled in five ($p<0.05$, Tg-Cre vs. Tg-inert; $p=0.001$, Tg-Cre+BDNF vs. Tg-inert) and or eight-month old Tg BAC-HD mice ($p<0.05$, Tg-Cre vs. Tg-inert; $p<0.001$, Tg-Cre+BDNF vs. Tg-inert) compared to the control transgenic animals. When compared to the wt mice, five and eight month-old Tg BAC-HD mice treated with Cre or Cre+BDNF traveled about the same distance as the control wt mice or wt mice treated with Cre (Tg-Cre or Cre+BDNF vs. Wt. Cre or inert; all non-significant at 5 and 8 month time point).

Figure 5:
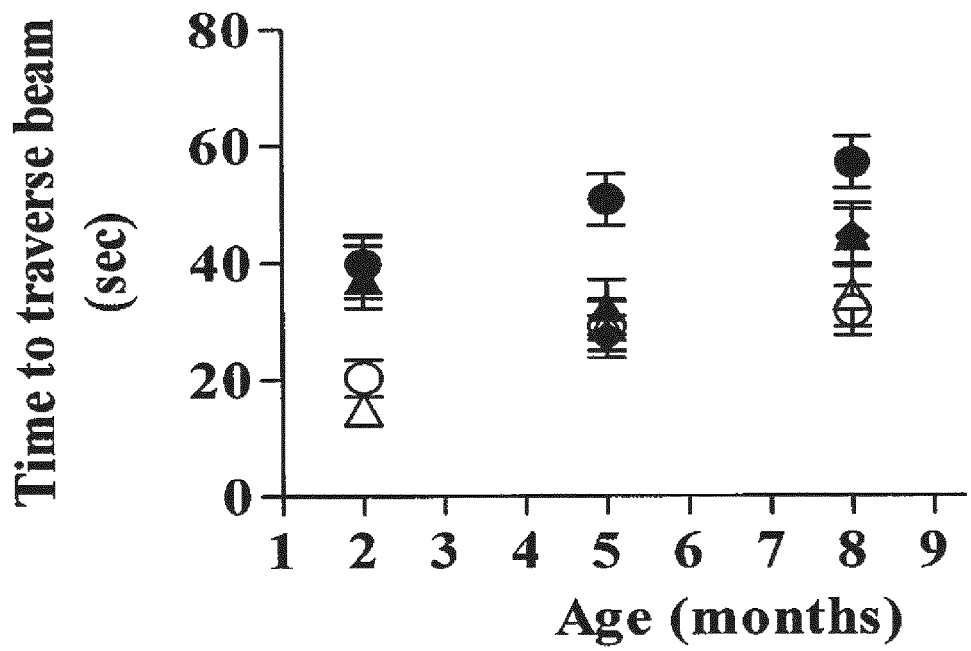
FIG. 5 illustrates decrease in the time to traverse the beam at five and eight months of age by transgenic (Tg BAC-HD) mice treated with Cre or Cre+BDNF at 2 months of age.

FIG. 5 illustrates the time taken by the animals to traverse the beam. While differences between wt and transgenic mice were observed in two-month old animals, treatment with Cre or Cre+BDNF at two months age attenuated or eliminated these differences at five ($p<0.01$, Tg-inert vs. Wt-inert or Wt-Cre or Tg-Cre+BDNF; $p<0.05$, Tg-inert vs. Tg-Cre) and eight months of age ($p<0.001$, Tg-inert vs. Wt-inert; $p<0.01$, Tg-inert vs. Wt-Cre).

Working Example 4

Figure 6:
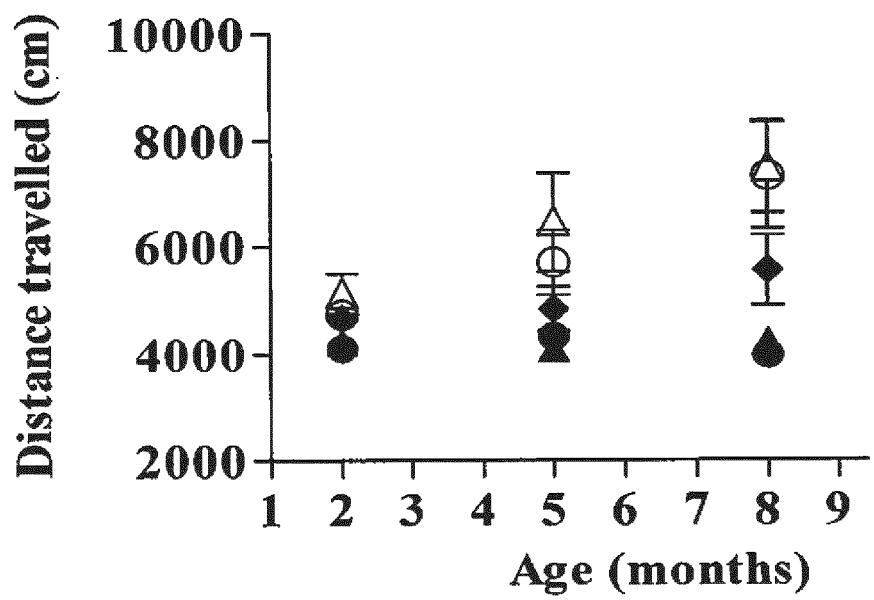
FIG. 6 illustrates an improvement of locomotor activity in Tg BAC-HD mice upon treatment with AAV-Cre+AAV-BDNF.

Tg BAC-HD Mice Reveal Improved Locomotor Activity Upon Treatment with AAV-Cre+AAV-BDNF, While Their Deficit in the Accelerating Rotarod Test Remains Unaltered Mice were placed in an open field chamber (40 cm×40 cm), and the distance traveled was scored by the ANY-maze software (Stoelting, Wood Dale, Ill.). Data are presented in FIG. 6 as mean±SEM values for each group. Briefly, the distance traveled increased with age in wt animals. In two month old Tg BAC-HD mice, the distance traveled was about the same as in wt animals. However, as the transgenic mice aged, the distance did not change. In eight month old control transgenic animals, the distance traveled was significantly less than the distance traveled by age-matched wt counterparts ($p<0.001$, Tg-inert or Cre vs. Wt-inert or Cre). Treatment with Cre+BDNF, but not Cre alone, somewhat increased the distance traveled, albeit no statistically significant differences were observed.

Figure 7:
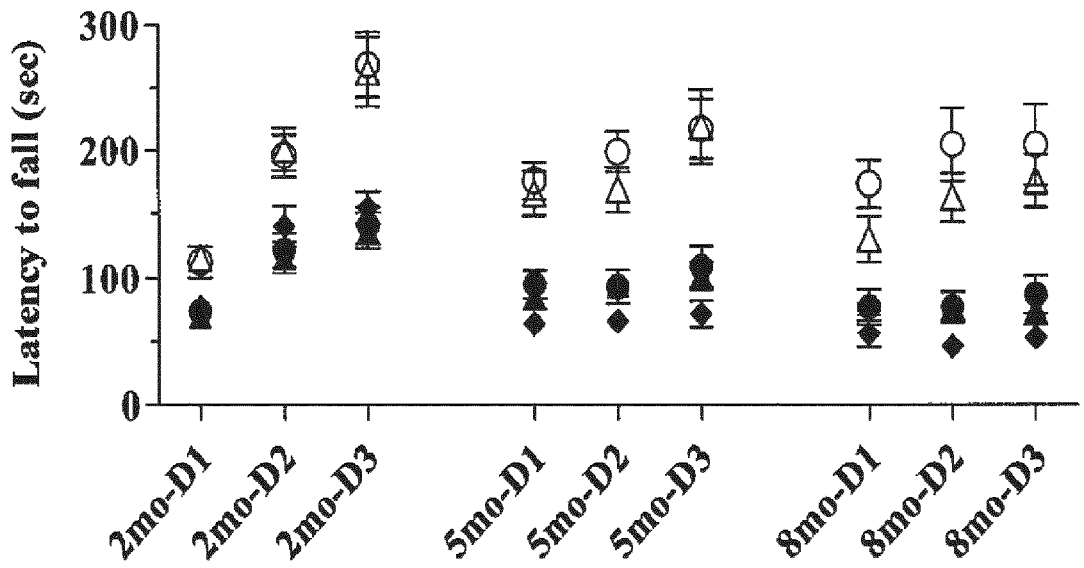
FIG. 7 demonstrates that treatment of Tg BAC-HD mice with AAV-Cre+AAV-BDNF does not affect performance in the accelerating rotarod test.

In another test, mice were subjected to an accelerating rotarod test (acceleration from 4-40 rpm for 5 min, followed by 40 rpm for 5 min) for 3 days, involving 3 trials (separated by an hr) per day. The latency to fall per day has been depicted in FIG. 7 as mean±SEM values for each group. In this test, treatments with Cre or Cre+BDNF did not improve the deficit exhibited by transgenic mice compared to wt animals.

Working Example 5

Figure 8:
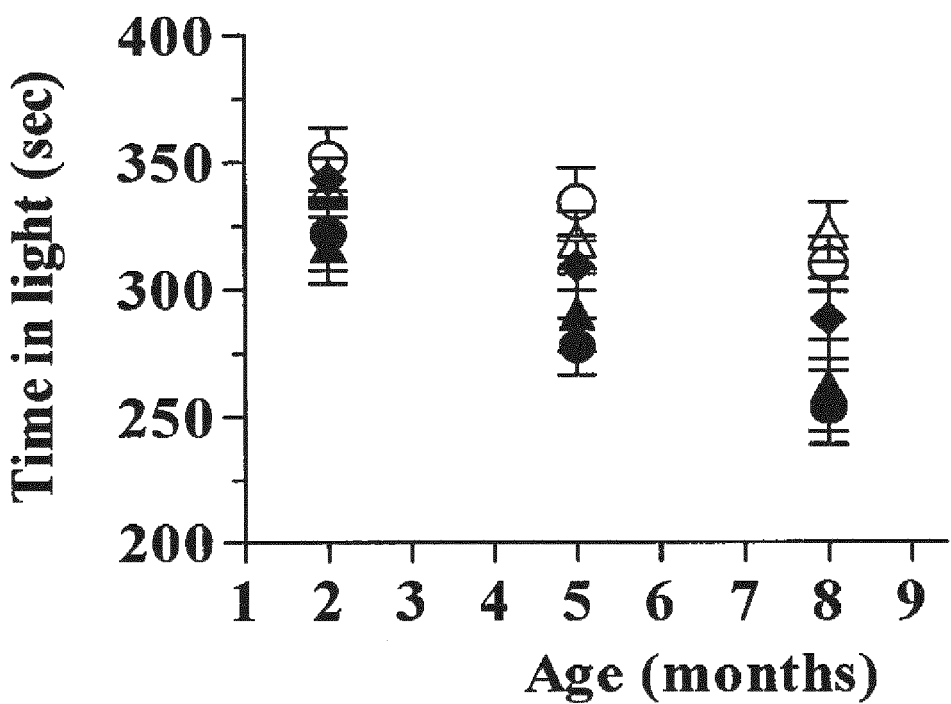
FIG. 8 demonstrates that Tg BAC-HD mice treated with Cre+BDNF tend to demonstrate a reduced anxiety.

Ongoing Testing Indicates Possibly Reduced Anxiety in the Tg BAC-HD Mice Upon Treatment with Cre+BDNF Mice were placed in the center of the light compartment facing away from the dark compartment in the light-dark box, and the number of transitions across the two compartments, total time spent in the light compartment, and the latency to first enter the dark compartment were scored blind. These data are illustrated in FIG. 8. ($p<0.05$, Tg-inert or Cre vs. Wt-inert or Cre at 8 months age). The mean±SEM values are presented for the time spent in light by each group; no group differences were observed for the number of transitions and latency to enter the dark compartment at any age.

Working Example 6

Figure 9:
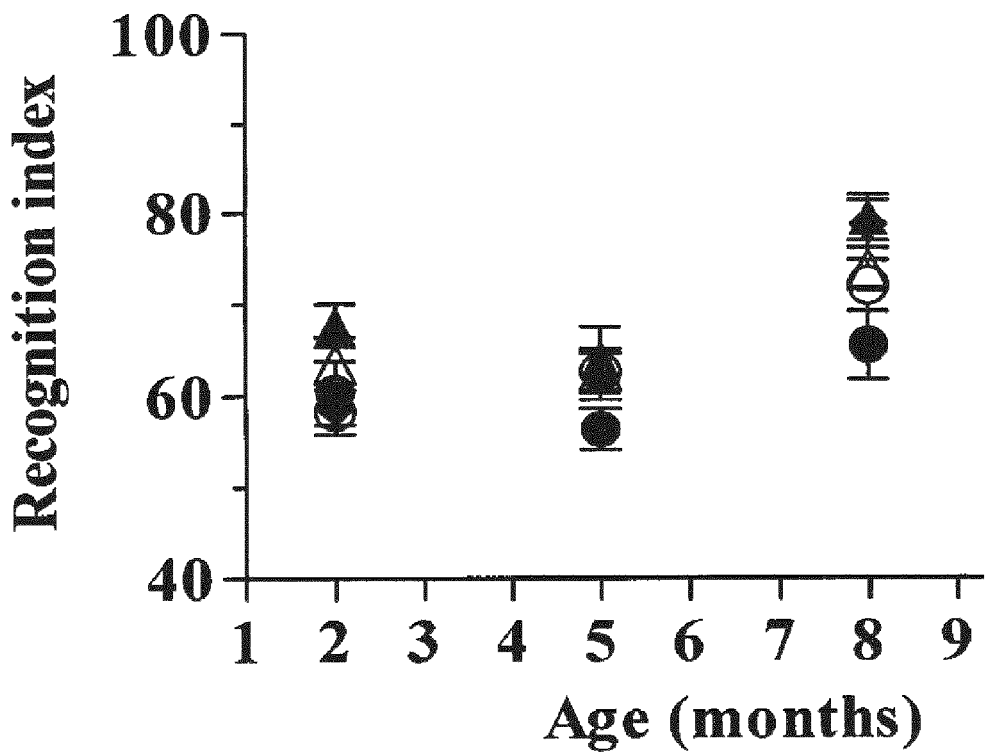
FIG. 9 demonstrates that treatment with Cre with or without BDNF tends to improve the performance of Tg BAC-HD mice in the novel object recognition test.
Figure 10:
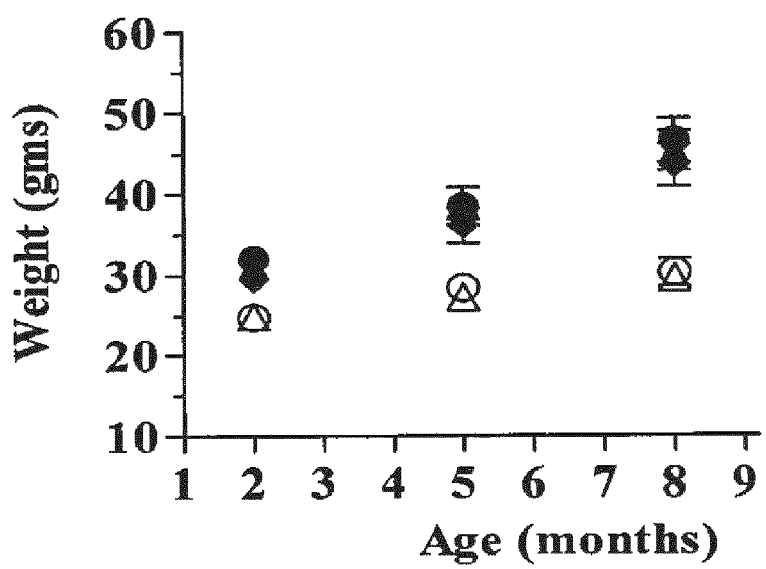
FIG. 10 demonstrates that Tg BAC-HD mice progressively gain weight as compared to wt animals.

Cre±BDNF Tends to Improve the Performance of Tg BAC-HD Mice in the Novel Object Recognition Test The novel object recognition test was continued on mice following the locomotion task in the open-field chamber. Mice were first allowed to explore 2 different objects, placed diagonally opposite in the field, for 10 min. In the subsequent 10-min trial, one of the objects was replaced with a novel object, and the recognition index was calculated as described (Dodart et al., 2002, *Nat. Neurosci.*, 5:452-7) using the ANY-maze software (Stoelting). Data are presented in FIG. 9 as mean±SEM values for each group. ($p<0.01$, Tg-inert vs. Tg-Cre or Cre+BDNF at 8 months age).

Every patent and non-patent publication cited in the instant disclosure is incorporated into the disclosure by reference to the same effect as if every publication is individually incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised Without departing from the spirit and scope of the present invention as defined by the following claims.

---

The invention claimed is:

1. A first nucleic acid sequence comprising:
   a second nucleic acid sequence encoding brain-derived neurotrophic factor (BDNF) or a functional fragment thereof; and
   a third nucleic acid sequence encoding an RNAi agent capable of inhibiting expression of huntingtin, said RNAi agent comprising a double-stranded structure having a first strand and a second strand, said first strand and said second strand each being between 19 and 30 nucleotides long, wherein the first strand is encoded by a sequence comprising any one of SEQ ID NO: 1-15.

2. The first nucleic acid sequence of claim 1, wherein the first nucleic acid sequence is included within a vector.

3. The first nucleic acid sequence of claim 2, wherein the vector is a viral vector.

4. The first nucleic acid sequence of claim 3, wherein the viral vector is an AAV viral vector.

5. The first nucleic acid sequence of claim 1, further comprising a first promoter capable of regulating expression of at least a part of the second nucleic acid sequence.

6. The first nucleic acid sequence of claim 1, further comprising a second promoter capable of regulating expression of at least a part of the third nucleic acid sequence.

7. A cell comprising the first nucleic acid sequence of claim 1.

8. A pharmaceutical composition comprising the first nucleic acid sequence of claim 1.

9. A method of treating Huntington's disease in a patient comprising administering to said patient:
   an RNAi agent capable of inhibiting expression of a gene involved in a neurodegenerative disease, said RNAi agent comprising a double-stranded structure having a first strand and a second strand, said first and second strands each being between 19 and 30 nucleotides long, wherein the first strand is encoded by a sequence comprising any one of SEQ ID NO: 1-15; and
   BDNF (brain-derived neurotrophic factor) or a functional fragment thereof or a nucleic acid sequence encoding BDNF or the functional fragment thereof.

10. The method of claim 9, wherein the RNAi agent is a vectorless molecule.

11. The method of claim 10, wherein the RNAi agent comprises a chemical modification.

12. The method of claim 11, wherein the chemical modification reduces alteration of said RNAi agent by endonucleases or exonucleases.

13. The method of claim 9, wherein the nucleic acid sequence encoding said BDNF or said functional fragment thereof is included within a vector.

14. The method of claim 13, wherein said vector does not include the RNAi agent.

15. The nucleic acid sequence of claim 13, wherein the vector is a viral vector.

16. The nucleic acid sequence of claim 13, wherein the viral vector is an AAV viral vector.

17. The method of claim 9, wherein said RNAi agent and said BDNF or the functional fragment thereof, or a nucleic acid sequence encoding said BDNF or the functional fragment thereof are administered by intracranial injection.

18. The method of claim 9, whereby said patient's locomotor activity is improved.

19. The method of claim 9, whereby said patient's anxiety is diminished.

* * * * *